(12) United States Patent
Pauza

(10) Patent No.: US 11,980,663 B2
(45) Date of Patent: May 14, 2024

(54) HIV PRE-IMMUNIZATION AND IMMUNOTHERAPY

(71) Applicant: American Gene Technologies International, Inc., Rockville, MD (US)

(72) Inventor: Charles David Pauza, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 0 days.

(21) Appl. No.: 15/736,284

(22) PCT Filed: Jul. 8, 2016

(86) PCT No.: PCT/US2016/041456
§ 371 (c)(1),
(2) Date: Dec. 13, 2017

(87) PCT Pub. No.: WO2017/007994
PCT Pub. Date: Jan. 12, 2017

(65) Prior Publication Data
US 2018/0177866 A1 Jun. 28, 2018

Related U.S. Application Data

(60) Provisional application No. 62/190,139, filed on Jul. 8, 2015.

(51) Int. Cl.
A61K 39/00 (2006.01)
A61K 35/17 (2015.01)
(Continued)

(52) U.S. Cl.
CPC .............. *A61K 39/21* (2013.01); *A61K 35/17* (2013.01); *A61K 39/12* (2013.01); *A61P 31/18* (2018.01);
(Continued)

(58) Field of Classification Search
None
See application file for complete search history.

(56) References Cited

U.S. PATENT DOCUMENTS 5,668,255 A 9/1997 Murphy
5,674,703 A 10/1997 Woo et al.
(Continued)

FOREIGN PATENT DOCUMENTS

BR 2515 3/2019
CN 101516365 8/2009
(Continued)

OTHER PUBLICATIONS

Mason et al., "Inactivated Simian Immunodeficiency Virus-Pulsed Autologous Fresh Blood Cells as an Immunotherapy Strategy," Journal of Virology, vol. 83, No. 3: 1501-1510 (Year: 2009).*
(Continued)

*Primary Examiner* — M Franco G Salvoza
(74) *Attorney, Agent, or Firm* — DLA Piper LLP (US)

(57) ABSTRACT

The present invention relates generally to immunization and immunotherapy for the treatment or prevention of HIV. In particular, the methods relate to in vivo and ex vivo enrichment of HIV-specific CD4 T cells. In certain embodiments, the disclosed compositions and methods can incorporate therapy in order to further enhance the HIV-specific CD4 T cells.

18 Claims, 20 Drawing Sheets

Specification includes a Sequence Listing.

(51) Int. Cl.
  *A61K 39/12* (2006.01)
  *A61K 39/21* (2006.01)
  *A61P 31/18* (2006.01)
  *C12N 15/113* (2010.01)
  *C12N 15/86* (2006.01)
  *C12Q 1/06* (2006.01)
  *A61K 48/00* (2006.01)

(52) U.S. Cl.
  CPC .......... *C12N 15/1138* (2013.01); *C12N 15/86* (2013.01); *C12Q 1/06* (2013.01); *A61K 2039/5156* (2013.01); *A61K 2039/5158* (2013.01); *A61K 2039/57* (2013.01); *A61K 48/00* (2013.01); *C12N 2310/14* (2013.01); *C12N 2740/15041* (2013.01); *C12N 2740/15043* (2013.01); *C12N 2740/16034* (2013.01); *C12N 2740/16041* (2013.01)

(56) References Cited

U.S. PATENT DOCUMENTS

| | | | |
|---|---|---|---|
| 6,156,514 | A | 12/2000 | Acevedo et al. |
| 6,399,383 | B1 | 6/2002 | Apt et al. |
| 6,635,472 | B1 | 10/2003 | Lauermann |
| 7,371,542 | B2 | 5/2008 | Ivanova et al. |
| 8,124,752 | B2 | 2/2012 | Bumcrot et al. |
| 8,287,857 | B2 | 10/2012 | Dudley et al. |
| 8,993,532 | B2 | 3/2015 | Hannon et al. |
| 9,522,176 | B2 | 12/2016 | DeRosa et al. |
| 9,527,904 | B2 | 12/2016 | Balazs |
| 9,834,790 | B1 | 12/2017 | Pauza et al. |
| 9,834,791 | B2 | 12/2017 | Zhang |
| 9,914,938 | B2 | 3/2018 | Pauza et al. |
| 10,023,880 | B2 | 7/2018 | Pauza et al. |
| 10,036,038 | B2 | 7/2018 | Pauza et al. |
| 10,036,040 | B2 | 7/2018 | Pauza et al. |
| 10,137,144 | B2 | 11/2018 | Pauza et al. |
| 10,208,295 | B2 | 2/2019 | Derosa et al. |
| 10,233,464 | B2 | 3/2019 | Pauza et al. |
| 2002/0168345 | A1 | 11/2002 | Dong et al. |
| 2003/0013196 | A1 | 1/2003 | Engelman et al. |
| 2003/0096787 | A1 | 5/2003 | Perricaudet et al. |
| 2003/0119770 | A1 | 6/2003 | Lai |
| 2003/0138444 | A1* | 7/2003 | Zavitz ................ C07K 14/005 424/188.1 |
| 2004/0142416 | A1 | 7/2004 | Laipis et al. |
| 2004/0161412 | A1 | 8/2004 | Penn et al. |
| 2004/0192629 | A1 | 9/2004 | Xu et al. |
| 2004/0214158 | A1 | 10/2004 | Sethi et al. |
| 2004/0248296 | A1 | 12/2004 | Beresford et al. |
| 2005/0019927 | A1 | 1/2005 | Markus et al. |
| 2005/0138677 | A1 | 6/2005 | Pfister et al. |
| 2006/0057553 | A1 | 3/2006 | Aguilar-Cordova |
| 2006/0183230 | A1 | 8/2006 | Silla et al. |
| 2006/0246520 | A1 | 11/2006 | Champagne et al. |
| 2007/0026521 | A1 | 2/2007 | Colosi |
| 2007/0141679 | A1 | 6/2007 | Sodroski |
| 2007/0203333 | A1 | 8/2007 | McSwiggen et al. |
| 2008/0003225 | A1 | 1/2008 | Vie et al. |
| 2008/0003682 | A1* | 1/2008 | Lois-Caballe .......... A61P 31/14 435/456 |
| 2008/0039413 | A1 | 2/2008 | Morris et al. |
| 2008/0131940 | A1 | 6/2008 | Chiu |
| 2008/0153737 | A1 | 6/2008 | Lieberman et al. |
| 2008/0199961 | A1 | 8/2008 | Rasko et al. |
| 2008/0227736 | A1 | 9/2008 | Chen et al. |
| 2008/0293142 | A1 | 11/2008 | Liu et al. |
| 2009/0148936 | A1 | 6/2009 | Stout et al. |
| 2009/0304688 | A1 | 12/2009 | Fournie et al. |
| 2010/0017911 | A1 | 1/2010 | Dawson et al. |
| 2010/0069372 | A1 | 3/2010 | Kazantsev |
| 2010/0119511 | A1 | 5/2010 | Wang et al. |
| 2010/0120155 | A1 | 5/2010 | Brennan et al. |
| 2010/0286166 | A1 | 11/2010 | Rodriguez et al. |
| 2010/0316676 | A1 | 12/2010 | Sanders |
| 2011/0008803 | A1 | 1/2011 | Stockwell et al. |
| 2011/0177155 | A1 | 7/2011 | Peer et al. |
| 2011/0207226 | A1 | 8/2011 | Ni et al. |
| 2012/0053223 | A1 | 1/2012 | Benkirane et al. |
| 2012/0027725 | A1 | 2/2012 | Galvin |
| 2012/0114607 | A1 | 5/2012 | Zhennan et al. |
| 2012/0034197 | A1 | 8/2012 | Young et al. |
| 2012/0201794 | A1* | 8/2012 | Chen ................ A01K 67/0271 424/93.21 |
| 2013/0078276 | A1 | 3/2013 | Robinson et al. |
| 2013/0090371 | A1 | 4/2013 | Lu et al. |
| 2013/0142766 | A1 | 6/2013 | Dodo et al. |
| 2013/0211380 | A1 | 8/2013 | Cabrera Aquino et al. |
| 2014/0155468 | A1 | 6/2014 | Gregory et al. |
| 2014/0162894 | A1 | 6/2014 | Hatchwell et al. |
| 2014/0178340 | A1 | 6/2014 | Robbins et al. |
| 2014/0234958 | A1 | 8/2014 | Kasahara et al. |
| 2014/0248277 | A1 | 9/2014 | Hoffman et al. |
| 2014/0336245 | A1 | 11/2014 | Mingozzi et al. |
| 2015/0010578 | A1 | 1/2015 | Balazs et al. |
| 2015/0018539 | A1 | 1/2015 | Fellmann |
| 2015/0126580 | A1 | 5/2015 | DePinho et al. |
| 2015/0132255 | A1* | 5/2015 | Sorensen ............... A61K 39/42 424/85.2 |
| 2015/0176006 | A1 | 6/2015 | Krause et al. |
| 2016/0060707 | A1 | 3/2016 | Goldenberg et al. |
| 2016/0243169 | A1 | 8/2016 | Chen et al. |
| 2016/0289681 | A1 | 10/2016 | Rossi |
| 2017/0015976 | A1 | 1/2017 | Nelson |
| 2017/0028036 | A1 | 2/2017 | Mingozzi et al. |
| 2017/0037369 | A1 | 2/2017 | Ramsborg et al. |
| 2017/0240899 | A1* | 8/2017 | Wu .................... C12N 15/1138 |
| 2017/0335344 | A1 | 11/2017 | Pauza et al. |
| 2018/0010147 | A1 | 1/2018 | Pauza |
| 2018/0142257 | A1 | 5/2018 | Pauza |
| 2018/0142258 | A1 | 5/2018 | Pauza |
| 2018/0161455 | A1 | 6/2018 | Pauza |
| 2018/0195046 | A1 | 7/2018 | Deng |
| 2018/0195050 | A1 | 7/2018 | Szalay |
| 2018/0256624 | A1 | 9/2018 | Pauza |
| 2018/0305716 | A1 | 10/2018 | Pauza |
| 2018/0355032 | A1 | 12/2018 | Roberts |
| 2019/0046633 | A1 | 2/2019 | Pauza |
| 2019/0062786 | A1 | 2/2019 | Pauza et al. |
| 2019/0078096 | A1 | 3/2019 | Lahusen et al. |
| 2019/0083523 | A1 | 3/2019 | Pauza |
| 2019/0388456 | A1 | 12/2019 | Pauza et al. |
| 2020/0063161 | A1 | 2/2020 | Pauza |
| 2020/0087682 | A1 | 3/2020 | Lahusen et al. |
| 2020/0109417 | A1 | 4/2020 | Pauza et al. |
| 2020/0155590 | A1 | 5/2020 | Zhennan |
| 2020/0181645 | A1 | 6/2020 | Pauza |
| 2020/0318081 | A1 | 10/2020 | Lahusen et al. |
| 2021/0047644 | A1 | 2/2021 | Lahusen |
| 2021/0121561 | A1 | 4/2021 | Pauza |

FOREIGN PATENT DOCUMENTS

| | | |
|---|---|---|
| CN | 101679466 | 3/2010 |
| CN | 101805750 | 8/2010 |
| CN | 103184224 | 7/2013 |
| CN | 105112370 | 12/2015 |
| CN | 108883100 | 11/2018 |
| EP | 1647595 | 4/2006 |
| EP | 3402483 | 11/2018 |
| EP | 3413926 | 12/2018 |
| EP | 3426777 | 1/2019 |
| EP | 3468617 | 4/2019 |
| EP | 3468618 | 4/2019 |
| EP | 3481418 | 5/2019 |
| EP | 3481435 | 5/2019 |
| IN | 201947000153 | 2/2019 |
| JP | 2002506652 | 3/2002 |
| JP | 2007-527240 | 9/2007 |
| JP | 2008518591 | 6/2008 |
| JP | 2008-538174 | 10/2008 |
| JP | 2010-520757 | 6/2010 |
| JP | 2011-517409 | 6/2011 |

(56) References Cited

FOREIGN PATENT DOCUMENTS

| | | |
|---|---|---|
| JP | 2012508591 | 4/2012 |
| JP | 2012533299 | 12/2012 |
| JP | 2013-507107 | 3/2013 |
| JP | 2013-5300152 | 7/2013 |
| JP | 2015-518838 | 7/2015 |
| JP | 2016-502404 | 1/2016 |
| JP | 2018-541270 | 4/2019 |
| WO | 199947691 | 9/1999 |
| WO | 2002020554 | 3/2002 |
| WO | 2003093436 | 11/2003 |
| WO | 2004053137 | 6/2004 |
| WO | 2005028634 | 3/2005 |
| WO | 2005033282 | 4/2005 |
| WO | 2006039721 | 4/2006 |
| WO | 2006048215 | 5/2006 |
| WO | 2007000668 | 1/2007 |
| WO | 2007015122 | 2/2007 |
| WO | 2007132292 | 11/2007 |
| WO | 2007133674 | 11/2007 |
| WO | 2008025025 | 2/2008 |
| WO | 2008090185 | 7/2008 |
| WO | WO 2008/109837 | 9/2008 |
| WO | 2009100928 | 8/2009 |
| WO | WO-2009100955 A1 * 8/2009 ......... C12N 15/1138 |
| WO | 2009147445 | 12/2009 |
| WO | 2010051521 | 5/2010 |
| WO | 2010117974 | 10/2010 |
| WO | 2010127166 | 11/2010 |
| WO | 2011008348 | 1/2011 |
| WO | 2011071476 | 6/2011 |
| WO | 2011119942 | 9/2011 |
| WO | 2012048303 | 4/2012 |
| WO | 2012061075 | 5/2012 |
| WO | 2012145624 | 10/2012 |
| WO | 2013096455 | 6/2013 |
| WO | 2014016817 | 1/2014 |
| WO | WO-2014016817 A2 * 1/2014 ........... C12N 15/111 |
| WO | 2014117050 | 7/2014 |
| WO | 2014187881 | 11/2014 |
| WO | 2015017755 | 2/2015 |
| WO | 2015042308 | 3/2015 |
| WO | 2015061491 | 4/2015 |
| WO | 2015078999 | 6/2015 |
| WO | 2015086854 | 8/2015 |
| WO | WO2015164759 | 10/2015 |
| WO | 2016046234 | 3/2016 |
| WO | 2016054654 | 4/2016 |
| WO | 2016061232 | 4/2016 |
| WO | 2019070674 | 4/2016 |
| WO | 2016069518 | 5/2016 |
| WO | 2016069716 | 5/2016 |
| WO | 2016200997 | 7/2016 |
| WO | WO 2016/186708 A1 | 11/2016 |
| WO | 2016189159 | 12/2016 |
| WO | 2017007994 | 1/2017 |
| WO | 20170068077 | 4/2017 |
| WO | 2017100551 | 6/2017 |
| WO | 2017123918 | 7/2017 |
| WO | 2017139065 | 8/2017 |
| WO | 2017156311 | 9/2017 |
| WO | 20170173453 | 10/2017 |
| WO | 2017213697 | 12/2017 |
| WO | 2017214327 | 12/2017 |
| WO | 2018009246 | 1/2018 |
| WO | 2018009847 | 1/2018 |
| WO | 2018017882 | 1/2018 |
| WO | 2018126112 | 7/2018 |
| WO | 2018129540 | 7/2018 |
| WO | 20180148443 | 8/2018 |
| WO | WO 2018/025923 | 8/2018 |
| WO | 2018187231 | 10/2018 |
| WO | 2018232359 | 12/2018 |
| WO | 2020097049 | 5/2020 |
| WO | 2020243717 | 12/2020 |

OTHER PUBLICATIONS

Blick et al., "Cyclophosphamide Enhances SB-728-T Engraftment to Levels Associated with HIV-RNA Control," Abstract 141, CROI Conference on Retroviruses and Opportunistic Infections, Boston, Massachusetts (Year: 2014).*

De Rose et al., "Safety, immunogenicity and efficacy of peptide-pulsed cellular immunotherapy in macaques," J Med Primatol., 27 (Suppl 2): 69-78 (Year: 2008).*

Smith et al., "Developments in HIV-1 immunotherapy and therapeutic vaccination," F1000Prime Reports 6:42 (Year: 2014).*

EPO English translation of He et al. (Cn 103184224A) (Year: 2020).*

Zhang et al.,, "Uracils at nucleotide position 9-11 are required for the rapid turnover of miR-29 family," Nucleic Acids Research, vol. 39, No. 10: 4387-4395 (Year: 2011).*

Hafid et al., "Phenylketonuria: A Review of Current and Future Treatments," Translational Pediatrics, vol. 4(4), pp. 304-317, (2015).

Blau et al., "Phenylketonuria," The Lancet, vol. 376(9750), pp. 1417-1427, (2010).

Chandler et al., "Vector Design Influences Hepatic Genotoxicity After Adeno-Associated Virus Gene Therapy," Journal of Clinical Investigation, vol. 125(2), pp. 870-880, (2015).

Christophersen et al., "A Technique of Transumbilical Portal Vein Catheterization in Adults," The Archives of Surgery, vol. 95(6), pp. 960-963, (1967). (Abstract Only).

Bartholome, "Genetics and Biochemistry of the Phenylketonuria-Present State," Human Genetics, vol. 51(3), pp. 241-245, (1979).

Donsante et al., "AAV Vector Integration Sites in Mouse Hepatocellular Carcinoma," Science, vol. 317, p. 477, (2007).

Eisensmith et al., "Multiple Origins for Phenylketonuria in Europe," American Journal of Human Genetics, vol. 51(6), pp. 1355-1365, (1992).

Fisher et al., "The Inhibition of Phenylalanine and Tyrosine Hydroxylases by High Oxygen Levels," Journal of Neurochemistry, vol. 19(5), pp. 1359-1365, (1972). (Abstract Only).

Grisch-Chan et al., "Low-Dose Gene Therapy for Murine PKU Using Episomal Naked DNA Vectors Expressing PAH from Its Endogenous Liver Promoter," Molecular Therapy Nucleic Acids, vol. 7, pp. 339-349, (2017).

Guldberg et al., "Aberrant Phenylalanine Metabolism in Phenylketonuria Heterozygotes," Journal of Inherited Metabolic Disease, vol. 21(4), pp. 365-372, (1998).

Kaufman et al., "A Model of Human Phenylalanine Metabolism in Normal Subjects and in Phenylketonuric Patients," Proceedings of the National Academy of Sciences USA, vol. 96(6), pp. 3160-3164, (1999).

Kaufman et al., "Phenylalanine Hydroxylase Activity in Liver Biopsies from Hyperphenylalaninemia Heterozygotes: Deviation from Proportionality with Gene Dosage," Pediatric Research, vol. 9(8), pp. 632-634, (1975).

Longo et al., "Single-Dose, Subcutaneous Recombinant Phenylalanine Ammonia Lyase Conjugated with Polyethylene Glycol in Adult Patients with Phenylketonuria: An Open-Label, Multicentre, Phase 1 Dose-Escalation Trial," The Lancet, vol. 384(9937), pp. 37-44, (2014).

Mochizuki et al., "Long-Term Correction of Hyperphenylalaninemia by AAV-Mediated Gene Transfer Leads to Behavioral Recovery in Phenylketonuria Mice," Gene Therapy, vol. 11(13), pp. 1081-1086, (2004).

Nault et al., "Adeno-Associated Virus Type 2 as an Oncogenic Virus in Human Hepatocellular Carcinoma," Molecular & Cellular Oncology, vol. 3(2), p. e1095271, 3 pages, (2016).

Oh et al., "Reversal of Gene Expression Profile in the Phenylketonuria Mouse Model After Adeno-Associated Virus Vector-Mediated Gene Therapy," Molecular Genetics and Metabolism, vol. 86(Supp. 1), pp. S124-S132, (2005).

Oh et al., "Long-Term Enzymatic and Phenotypic Correction in the Phenylketonuria Mouse Model by Adeno-Associated Virus Vector-Mediated Gene Transfer," Pediatric Research, vol. 56(2), pp. 278-284, (2004).

(56) References Cited

OTHER PUBLICATIONS

Pan et al., "Biodistribution and Toxicity Studies of VSVG-Pseudotyped Lentiviral Vector After Intravenous Administration in Mice with the Observation of in Vivo Transduction of Bone Marrow," Molecular Therapy, vol. 6(1), pp. 19-29, (2002).
Shedlovsky et al., "Mouse Models of Human Phenylketonuria," Genetics, vol. 134(4), pp. 1205-1210, (1993).
Yagi et al., "Complete Restoration of Phenylalanine Oxidation in Phenylketonuria Mouse by a Self-Complementary Adeno-Associated Virus Vector," Journal of Gene Medicine, vol. 13(2), pp. 114-122, (2011).
Yano et al., "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, vol. 11(8), p. e0160892, 14 pages, (2016).
USPTO; Non-Final Office Action dated Sep. 19, 2018 in U.S. Appl. No. 16/011,550.
USPTO; Invitation to Pay Additional Fees and, where Applicable, Protest Fee dated Sep. 11, 2018 in Application No. PCT/US2018/37924.
PCT: International Search Report dated May 29, 2018 in Application No. PCT/US2018/012998.
PCT: Written Opinion dated May 29, 2018 in Application No. PCT/US2018/012998.
USPTO; Notice of Allowance dated Apr. 23, 2018 in U.S. Appl. No. 15/850,937.
USPTO; Notice Allowance dated Apr. 26, 2018 in U.S. Appl. No. 15/849,062.
Capietto, A. H. et al., "Stimulated gammadelta T cells increase the in vivo efficacy of trastuzumab in HER-2+ breast cancer," J Immunol 187(2): 1031-1038, (2011).
Chen, Z. and M. S. Freedman, "CD16+ gammadelta T cells mediate antibody dependent cellular cytotoxicity: potential mechanism in the pathogenesis of multiple sclerosis," Clin Immunol 128(2): 219-227, (2008).
Couzi, L. et al., "Antibody-dependent anti-cytomegalovirus activity of human gammadelta T cells expressing CD16 (FcgammaRIIIa)," Blood 119(6): 1418-1427, (2012).
Fisher, J. P. et al., "Effective combination treatment of GD2-expressing neuroblastoma and Ewing's sarcoma using anti-GD2 ch14.18/CHO antibody with Vgamma9Vdelta2+ gammadeltaT cells," Oncoimmunology 5(1): e1025194, (2016).
Gertner-Dardenne, J. et al., "Bromohydrin pyrophosphate enhances antibody-dependent cell-mediated cytotoxicity induced by therapeutic antibodies," Blood 113(20): 4875-4884, (2009).
Poonia, B. and C. D. Pauza, "Gamma delta T cells from HIV+ donors can be expanded in vitro by zoledronate/interleukin-2 to become cytotoxic effectors for antibody-dependent cellular cytotoxicity," Cytotherapy 14(2): 173-181, (2012).
Schiller, C. B. et al., "CD19-specific triplebody SPM-1 engages NK and gammadelta T cells for rapid and efficient lysis of malignant B-lymphoid cells," Oncotarget 7(50): 83392-83408, (2016).
Tokuyama, H. et al., "V gamma 9 V delta 2 T cell cytotoxicity against tumor cells is enhanced by monoclonal antibody drugs—rituximab and trastuzumab," Int J Cancer 122(11): 2526-2534, (2008).
Zufferey et al., "Self-Inactivating Lentivirus Vector for Safe and Efficient In Vivo Gene Delivery," Journal of Virology, vol. 72(12), pp. 9873-9880, (1998).
USPTO; Non-Final Office Action dated Feb. 22, 2018 in U.S. Appl. No. 15/850,937.
USPTO; Non-Final Office Action dated Feb. 22, 2018 in U.S. Appl. No. 15/849,062.
USPTO; Non-Final Office Action dated Feb. 22, 2018 in U.S. Appl. No. 13/333,882.
Vargas, J. Jr et al., "Conditionally replicating lentiviral-hybrid episomal vectors for suicide gene therapy," Antiviral Res., vol. 80 No. 3, pp. 288-294, (Dec. 2008).
Thompson et al., "Alkylamines cause Vγ9V82 T-cell activation and proliferation by inhibiting the mevalonate pathway," Blood, vol. 107, pp. 651-654, (Jan. 2006).
Gober et al., "Human T Cell Receptor γδ Cells Recognize Endogenous Mevalonate Metabolites in Tumor Cells," J. of Experimental Med., vol. 197, pp. 163-168, (Jan. 2003).
Goepfert, et al., "Specificity and 6-Month Durability of Immune Responses Induced by DNA and Recombinant Modified Vaccinia Ankara Vaccines Expressing HIV-2 Virus-Like Particles," J. Infectious Diseases, vol. 210, pp. 99-110, (Jul. 2014).
Human papillomavirus type 16 (HPV16), complete genome; GenBank: K02718.1; Publication [online], https://www.ncbi.nlm.nih.gov/nucleotide/333031?report=genbank&log$=nucltop&blast_rank=22&RID=H3E1THFU014; pp. 1-4, (Mar. 1994).
{Long control region} [Human papillomavirus, type 16, Genomic, 860 nt]; Accession S60559. Publication [online], https://www.ncbi.nlm.nih.gov/nucleotide/237343?report=genbank&log$=nucltop&blast_rank=1&RID=H3FCKA00014; pp. 1, (May 1993).
Tebas, P. et al., "Antiviral effects of autologous CD4 T cells genetically modified with a conditionally replicating lentiviral vector expressing long antisense to HIV," Blood, vol. 121, No. 9, pp. 1524-1533, (2013).
Tebas, p et al., "Gene Editing of CCR5 in Autologous CD4 T Cells of Persons Infected with HIV," The New England Journal of Medicine, vol. 370 (10), pp. 901-910, (Mar. 2014).
Li et al., "Reduced Expression of the Mevalonate Pathway Enzyme Farnesyl Pyrophosphate Synthase Unveils Recognition of Tumor Cells by Vγ9V82 T Cells," J. of Immunology, vol. 182, pp. 8118-8124, (2009).
Wang et al., "Indirect Stimulation of Human Vγ9V82 T Cells through Alterations in Isoprenoid Metabolism," J. of Immunology, vol. 187 pp. 5099-5113, (2011).
Stunkel et al., "The Chromatin Structure of the Long Control Region of Human Papillomavirus Type 16 Repress Viral Oncoprotein Expression," Journal Of Virology, vol. 73, No. 3, pp. 1918-1930, (Mar. 1999).
Lu et al., "Anti-sense-Mediated Inhibition of Human Immunodeficiency Virus (HIV) Replication by Use of an HIV Type 1-Based Vector Results in Severely Attenuated Mutants Incapable of Developing Resistance," Journal of Virology, vol. 79, No. 13, pp. 7079-7088, (Jul. 2004).
Dieli et al., ""Targeting Human γδ T Cells with Zoledronate and Interleukin-2 for Immunotherapy of Hormone-Refractory Prostate Cancer,"" Europe PMC Funders Group, Cancer Res. vol. 67(15), pp. 7450-1451, (Aug. 2007).
GenBank Accession No. S60559 "(long control region) [human papillomavirus, type 16, Genomic, 860 nt]," [located online Nov. 21, 2017 at https://ncbi.nlm.nih.gov/nuccore/S60559] entire DNA sequence, (May 1993).
GenBank Accession No. JG619773, MNESCING-T3-001_L15_6FEB2009_054 Mnescing cell culture from Mahonia nervosa Berberis nervosa cDNA, mRNA sequence, (online). [Retrieved on Dec. 5, 2017]. Retrieved from the internet :< URL: https://www.ncbi.nlm.nih.gov/nucest/JG619773 > entire document, (Feb. 2014).
Moser et al., "γd T cells: novel initiators of adaptive immunity," Immunological Reviews, vol. 215, pp. 89-102, (Feb. 2007).
PCT: International Search Report dated Nov. 7, 2016 in Application No. PCT/US2016/036519.
PCT: Written Opinion dated Nov. 7, 2016 in Application No. PCT/US2016/036519.
PCT: International Search Report dated Oct. 19, 2016 in Application No. PCT/US2016/041456.
PCT: Written Opinion dated Oct. 19, 2016 in Application No. PCT/US2016/041456.
PCT: International Search Report dated Jul. 20, 2017 in Application No. PCT/US2017/043157.
PCT: Written Opinion dated Jul. 20, 2017 in application No. PCT/US2017/043157.
PCT: International Search Report dated Jun. 9, 2017 in Application No. PCT/US2016/066185.
PCT: Written Opinion dated Jun. 9, 2017 in Application No. PCT/US2016/066185.

(56) References Cited

OTHER PUBLICATIONS

PCT: International Search Report dated Jul. 17, 2017 in Application No. PCT/US2017/013019.
PCT: Written Opinion dated Jul. 17, 2017 in Application No. PCT/US2017/013019.
PCT: International Search Report dated May 26, 2017 in Application No. PCT/US2017/013399.
PCT: Written Opinion dated May 26, 2017 in Application No. PCT/US2017/013399.
PCT: International Search report dated Aug. 25, 2017 in Application No. PCT/US2017/021639.
PCT: Written Opinion dated Aug. 25, 2017 Application No. PCT/US2017/021639.
PCT: International Search Report dated Nov. 8, 2017 Application No. PCT/US2017/041168.
PCT: Written Opinion dated Nov. 8, 2017 in Application No. PCT/US2017/041168.
PCT: International Search Report dated Dec. 15, 2017 in Application No. PCT/US2017/36433.
PCT: Written Opinion dated Dec. 15, 2017 in Application No. PCT/US2017/36433.
PCT: International Search Report date Jul. 14, 2017 in Application No. PCT/US2017/013024.
PCT: Written Opinion dated Jul. 14, 2017 in application No. PCT/US2017/013024.
USPTO; Notice of Allowance dated Oct. 13, 2017 in U.S. Appl. No. 14/706,481.
USPTO; Requirement for Restriction dated Oct. 23, 2017 in U.S. Appl. No. 15/668,223.
USPTO; Notice of Allowance dated Nov. 2, 2017 in U.S. Appl. No. 15/652,080.
Fusetti, et al., "Structure of Tetrameric Human Phenylalanine Hydroxylase and Its Implications for Phenylketonuria," J. Bio. Chem., vol. 273, No. 27, pp. 16962-16958 (1998).
USPTO; Invitation to Pay Additional Fees And, Where Applicable, Protest Fee dated Jul. 17, 2018 in Application No. PCT/US2018/25733.
USPTO; Requirement for Restriction dated Aug. 3, 2018 in U.S. Appl. No. 16/011,550.
USPTO; Notice of Allowance dated Aug. 10, 2018 in U.S. Appl. No. 15/904,131.
USPTO; Final Office Action dated Aug. 27, 2018 in U.S. Appl. No. 13/333,882.
USPTO; Notice of Allowance dated Mar. 26, 2018 in U.S. Appl. No. 15/668,223.
Ostertag et al., Brain Tumor Eradication and Prolonged Survival from Intratumoral Conversion of 5-Fluorocytosine to 5-fluorouracil Using a Nonlytic Retroviral Replicating Vector, Neoro-Oncology 14(2), pp. 145-159, Feb. 2012.
Twitty et al., Retroviral Replicating Vectors Deliver Cytosine Deaminase Leading to Targeted 5-Fluorouracil-Mediated Cytotoxicity in Multiple Human Cancer Types, Human Gene Therapy Methods, 27(1), pp. 17-31, Feb. 1, 2016.
Charron et al., "Dominant-Negative Interference in the $Pah_{enu2}$ Mouse Model of PKU: Effectiveness of Vectors Expressing Either Modified Forms of Phenylalanine Hydroxylase (PAH) or Ribozymes Plus a Hardened PAH mRNA," Molecular Therapy, vol. 11: pp. S163-S164, (2005).
USPTO; Non-Final Office Action dated Jun. 15, 2018 in U.S. Appl. No. 15/904,131.
PCT; Invitation to Pay Additional Fees in Application No. PCT/US2018/053919 dated Feb. 22, 2019.
Charron, "Gene Therapy for Phenylketonuria: Dominant-Negative Interference in a Recessive Disease," Dissertation, University of Florida 2005, http://etd.fcla.edu/UF/UFE0011392/charron_c.pdf>, (retrieved Jul. 26, 2018) (2005).
Ding et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, vol. 13, pp. 583-587, (Dec. 1, 2005).
Nowacki et al., "The PAH Mutation Analysis Consortium Database: Update 1996," Nucleic Acid Research, vol. 25(1), pp. 139-142, (Jan. 1, 1997).
Condiotti et al., "Prolonged Liver-Specific Transgene Expression by a Non-Primate Lentiviral Vector," Biochemical and Biophysical Research Communications, vol. 320(3), pp. 998-1006, (Jul. 30, 2004).
PCT; International Search Report dated Sep. 24, 2018 in Application No. PCT/US2018/025733.
PCT; Written Opinion dated Sep. 24, 2018 in Application No. PCT/US2018/025733.
USPTO; Notice of Allowance dated Oct. 31, 2018 in U.S. Appl. No. 16/011,550.
Wang et al., "Butyrophilin 3A1 Plays an Essential Role in Prenyl Pyrophosphate Stimulation of Human Vg2Vd2 T Cells," Journal of Immunology, vol. 191(3), pp. 1029-1042, (Jul. 5, 2013).
Jiang et al., "A Novel EST-Derived RNAi Screen Reveals a Critical Role for Farnesyl Diphosphate Synthase in Beta2-Adrenergic Receptor Internalization and Down-Regulation," FASEB Journal, vol. 26(5), pp. 1-13, (Jan. 25, 2012).
Miettinen et al., "Mevalonate Pathway Regulates Cell Size Homeostasis and Proteostasis Through Autophagy," Cell Reports, vol. 13(11), pp. 2610-2620, (Dec. 2015).
Tolmachov, "Designing Lentiviral Gene Vectors," Viral Gene Therapy, Chapter 13, pp. 263-284, (2011).
Tracey, "Human DNA Sequence from Clone RP1-288M22 on Chromosome 6q 12-13," Complete Sequence, National Center for Biotechnology. GenBank Entry. Retrieved from the internet: <https://www.ncbi.nlm.nih.gov/nucleotide/AL035467.23?report=genbank&log$=nucltop&blast_rank=1&RID=UUD4GX2D014>; pp. 1-34, (Jan. 24, 2013).
PCT; International Search Report dated Nov. 9, 2018 in Application No. PCT/US2018/037924.
PCT; Written Opinion dated Nov. 9, 2018 in Application No. PCT/US2018/037924.
USPTO; Advisory Action dated Nov. 16, 2018 in U.S. Appl. No. 13/333,882.
Gorziglia et al., "Elimination of Both E1 and E2A from Adenovirus Vectors Further Improves Prospects for In Vivo Human gene Therapy," Journal of Virology, vol. 70(6), pp. 4173-4178, (1996).
Vargas et al., "Novel Integrase-Defective Lentiviral Episomal Vectors for Gene Transfer," Human Gene Therapy, vol. 15(4), pp. 361-372, (Apr. 2004).
Wendelburg et al., "An Enhanced EBNA1 Variant with reduced IR3 Domain for Long-Term Episomal Maintenance and Transgene Expression of ORIP-Based Plasmids in Human Cells," Gene Therapy, vol. 5, pp. 1389-1399, (Oct. 1998).
Westerhout et al., "A Conditionally Replicating HIV-Based Vector that Stably Expresses an Antiviral shRNA Against HIV-1 Replication," Molecular Therapy: The Journal of the American Society of Gene Therapy, vol. 14(2), pp. 268-275, (May 2006).
Lam et al., "T-Cell Therapies for HIV," Immunotherapy, Future Medicine, vol. 5(4), pp. 407-414, (Apr. 2013).
Munoz et al., "Ex Vivo Expansion and Lentiviral Transduction of *Macaca Nemestrina* CD4 + T Cells," Journal of Medical Primatology, vol. 38(6), pp. 438-443, (Dec. 2009).
Porichis et al., "HIV-Specific CD4 T Cells and Immune Control of Viral Replication," Current Opinion in HIV and Aids, vol. 6(3), pp. 174-180, (May 2011).
Kavanagh et al., "Expansion of HIV-Specific CD4+ and CD8+ T Cells by Dendritic Cells Transfected with mRNA Encoding Cytoplasm- or Lysosome-Targeted Nef," Blood, American Society of Hematology, vol. 107(5), pp. 1963-1969, (Mar. 2006).
Akinsheye et al., "Fetal Hemoglobin in Sickle Cell Anemia," Blood, vol. 118(1), pp. 19-27, (2011).
USPTO; Non-Final Office Action dated Dec. 31, 2018 in U.S. Appl. No. 16/182,443
EPO; Extended Search Report dated Dec. 12, 2018 in EP Application No. 16808223.8 .

(56) References Cited

OTHER PUBLICATIONS

EPO; Extended Search Report dated Dec. 11, 2018 in EP Application No. 16822021.8.
Quan Jun-Jie et al., "Parp3 interacts with FoxM1 to confer glioblastoma cell radio resistance", Tumor Biology, Karger, Basel, CH, vol. 36, No. 11, Jun. 4, 2015 (Jun. 4, 2015), pp. 8617-8624, XP036217799, ISSN: 1010-4283, DOI: 10.1007/813277-015-3554-4 [retrieved on Jun. 4, 2015] whole document.
Jakobsson J. and Lundberg C.: "Lentiviral 1, 2, 4-10 vectors for use in the central nervous system", Molecular Therapy: The Journal of the American Society of Gene Therapy, Cell Press, US, vol. 13, No. 3, Mar. 1, 2006 (Mar. 1, 2006), pp. 484-493, XP005326761, ISSN: 1525-0016, DOI: 10.1016/ J.Ymthe.2005.11.012 the whole document.
Yun Jong Lee et al., "Poly (ADP-ribose) in 1-15 the pathogenesis of Parkinson's disease", BMB Reports, vol. 47, No. 8, Aug. 31, 2014 (Aug. 31, 2014), pp. 424-432, XP55671927, KR, ISSN: 1976-6696, DOI: 10.5483/BMBRep.2014.47.8.119 the whole document.
Lang Yoo et Al., "Parp-1 regulates the expression of caspase-11", Biochemical and Biophysical Research Communications, vol. 408, No. 3, Apr. 22, 2011 (Apr. 22, 2011), pp. 489-493, XP028209824, ISSN: 0006-291X, DOI: 10.1016/ J. BBRC.2011.04.070 [retrieved on Apr. 22, 2011] whole document.
Tae-In Kam et al., "Poly (ADP-ribose) derived pathologic [alpha]—synuclein neurodegeneration in Parkinson's disease", Science, vol. 362, No. 6414, Nov. 1, 2018 (Nov. 1, 2018), p. eaat8407, XP55672116, US, ISSN: 00368075, DOI: 10.1126/science. aat8407 whole document.
Olsen A.L. and Feany M.B., "Parp Inhibitors and Parkinson's Disease", Jan. 1, 2019 (Jan. 1, 2019), XP55672111, retrieved from the Internet: URL: https://mfprac.com/web2019/07literature/literature/Neurology/ParkinsonPARPI_Olsen.pdf [retrieved on Feb. 27, 2020] the whole document.
Richard Lu et al., "Siman Virus 40-Based Replication of Catalytically Inactive Human Immunodeficiency Virus Type 1 Integrase Mutants in Nonpermissive T Cells and Monocyte-Derived Macrophages", Journal of Virology, Jan. 2004, p. 658-668. DOI: 10.1128/JVI.78.2658-668.2004.
FM Sverdrup et al., "Development of human papillomavirus plasmids capable of episomal replication in human cell lines", Gene Therapy, Mar. 26, 1999, p. 1317-1321, Retrieved from the Internet: URL: http://www.stockton-pressco.uk/gt.
Kathleen Van Craenenbroeck et al., "Episomal vectors for gene expression in mammalian cells", Eur J. Biochem, vol. 267, p. 5665-5678, Jul. 14, 2000.
USPTO; Non-Final Office Action dated Mar. 16, 2020 in the U.S. Appl. No. 16/083,384.
EPO; Extended European Supplemental Search Report dated Mar. 11, 2020 in the Application No. 17831904.2.
JP; Japanese Office Action in the Application No. 2017-564550 dated Mar. 18, 2020.
Hassan et al., "Isolation of umbilical cord mesenchymal stem cells using human blood derivative accompanied with explant method," Stem Cell Investigation, pp. 1-8, (2019).
Huang et al., "An Efficient protocol to generate placental chorionic plate-derived mesenchymal stem cells with superior proliferative and immunomodulatory properties," Stem Cell Research & Therapy, pp. 1-15, (2019).
USPTO; Restriction Requirement dated Oct. 22, 2019 in the U.S. Appl. No. 15/580,661.
USPTO; Restriction Requirement dated Nov. 4, 2019 in the U.S. Appl. No. 16/076,655.
USPTO; Notice of Allowance dated Oct. 29, 2019 in the U.S. Appl. No. 13/333,882.
USPTO; Restriction Requirement dated Nov. 7, 2019 in the U.S. Appl. No. 16/083,384.
Hee Yeon Kim., "Farnesyl diphosphate synthase is important for the maintenance of glioblastoma stemness," Experimental & Molecular Medicine, (2018).

Hong Wang., "Indirect Stimulation of Human V2V2 Cells Through Alterations in Isoprenoid Metabolism," The Journal of Immunology, (2011).
Z. Li, "Inhibition of farnesyl pyrophosphate synthase prevents angiotensin II-induced cardiac fibrosis in vitro," Clinical & Experimental Immunology, (2014).
Xiaofeng Jiang, "A novel EST-derived RNAi screen reveals a critical role for farnesyl diphosphate in B2-adrenergic receptor internalization and down-regulation," The FASEB Journal, vol. 26, pp. 1-13 (2012).
Jian Yang, "Lentiviral-Mediated Silencing of Farnesyl Pyrophosphate Synthase through RNA Interference in Mice, "Biomed Research International, vol. 2015, Article ID 914026, 6 pages (2015).
Yang Ye, "Knockdown of farnesyl pyrophosphate synthase prevents angiotensin II-medicated cardiac hypertrophy," The International Journal of Biochemistry & Cell Biology, vol. 42, pp. 2056-2064, (2010).
Jianqiang Li, "Reduced Expression of Mevalonate Pathway Enzyme Farnesyl Pyrophosphate Synthase Unveils Recognition of Tumor Cells by V9V2 Cells," The Journal of Immunology, pp. 8118-8124, (2019).
Daryl S. Schiller, "Parameters Influencing Measurement of the Gag Antigen-Specific T-Proliferative Response to HIV Type 1 Infection," AIDS Research and Human Retroviruses, vol. 16, No. 3, pp. 259-271, (2000).
PCT; International Search Report dated Jul. 22, 2019 in the Application No. PCT/US2019/24410.
PCT; Written Opinion of the International Search Report dated Jul. 22, 2019 in the Application No. PCT/US2019/24410.
PCT; International Preliminary Report on Patentability dated Jul. 9, 2019 in the Application No. PCT/US2018/012998.
USPTO; Notice of Allowance dated Jun. 18, 2019 in the U.S. Appl. No. 16/182,443.
USPTO; Notice of Allowance dated Aug. 14, 2019 in the U.S. Appl. No. 16/008,991.
USPTO; Notice of Allowance dated Sep. 25, 2019 in the U.S. Appl. No. 16/218,010.
USPTO; Final Office Action dated Jul. 1, 2019 in the U.S. Appl. No. 16/132,247.
USPTO; Notice of Allowance dated Jul. 19, 2019 in the U.S. Appl. No. 16/132,247.
EPO; European Search Report dated Aug. 12, 2019 in the EP Application No. 17764128.9.
EPO; Supplementary European Search Report dated Sep. 6, 2019 in the Application No. 17750547.6.
USPTO; Non-Final Office Action dated Jan. 13, 2020 in the U.S. Appl. No. 15/580,661
Brites, C., M. Abrahao, P. Bozza, E. M. Netto, A. Lyra and F. Bahia (2018). "Infection by HTLV-1 Is Associated with High Levels of Proinflammatory Cytokines in HIV-HCV-Coinfected Patients." J Acquir Immune Defic Syndr 77(2): 230-234.
Douek, D. C., J. M. Brenchley, M. R. Betts, D. R. Ambrozak, B. J. Hill, et al. (2002). "HIV preferentially infects HIV-specific CD4+ T cells." Nature 417(6884): 95-98.
Eguchi, K., N. Matsuoka, H. Ida, M. Nakashima, M. Sakai, et al. (1992). "Primary Sjogren's syndrome with antibodies to HTLV-I: clinical and laboratory features." Ann Rheum Dis 51(6): 769-776.
Futsch, N., R. Mahieux and H. Dutartre (2017). "HTLV-1, the Other Pathogenic Yet Neglected Human Retrovirus: From Transmission to Therapeutic Treatment." Viruses, 10, 1; doi: 10.3390/v10010001.
Gessain, A., F. Barin, J. C. Vernant, O. Gout, L. Maurs, A. Calender and G. de The (1985). "Antibodies to human T-lymphotropic virus type-I in patients with tropical spastic paraparesis." Lancet 2(8452): 407-410.
Gessain, A. and O. Cassar (2012). "Epidemiological Aspects and World Distribution of HTLV-1 Infection." Front Microbiol 3: 388.
Goncalves, D. U., F. A. Proietti, J. G. Ribas, M. G. Araujo, S. R. Pinheiro, A. C. Guedes and A. B. Carneiro-Proietti (2010). "Epidemiology, treatment, and prevention of human T-cell leukemia virus type 1-associated diseases." Clin Microbiol Rev 23(3): 577-589.
Kagdi, H., M. A. Demontis, J. C. Ramos and G. P. Taylor (2018). "Switching and loss of cellular cytokine producing capacity char-

(56) References Cited

OTHER PUBLICATIONS acterize in vivo viral infection and malignant transformation in human T-lymphotropic virus type 1 infection." PLoS Pathog 14(2): e1006861.
Kagdi, H. H., M. A. Demontis, P. A. Fields, J. C. Ramos, C. R. Bangham and G. P. Taylor (2017). "Risk stratification of adult T-cell leukemia/lymphoma using immunophenotyping." Cancer Med 6(1): 298-309.
Macnamara, A., A. Rowan, S. Hilburn, U. Kadolsky, H. Fujiwara, et al. (2010). "HLA class I binding of HBZ determines outcome in HTLV-1 infection." PLoS Pathog 6(9): e1001117.
Manel, N., F. J. Kim, S. Kinet, N. Taylor, M. Sitbon and J. L. Battini (2003). "The ubiquitous glucose transporter GLUT-1 is a receptor for HTLV." Cell 115(4): 449-459.
Martinez, M. P., J. Al-Saleem and P. L. Green (2019). "Comparative virology of HTLV-1 and HTLV-2." Retrovirology 16(1): 21.
Mochizuki, M., T. Watanabe, K. Yamaguchi, K. Takatsuki, K. Yoshimura, et al. (1992). "HTLV-I uveitis: a distinct clinical entity caused by HTLV-I." Jpn J Cancer Res 83(3): 236-239.
Mosley, A. J., B. Asquith and C. R. Bangham (2005). "Cell-mediated immune response to human T-lymphotropic virus type I." Viral Immunol 18(2): 293-305.
Nagai, M. and M. Osame (2003). "Human T-cell lymphotropic virus type I and neurological diseases." J Neurovirol 9(2): 228-235.
Yamano, Y. and T. Sato (2012). "Clinical pathophysiology of human T-lymphotropic virus-type 1-associated myelopathy/tropical spastic paraparesis." Front Microbiol 3: 389.
Nishioka, K., I. Maruyama, K. Sato, I. Kitajima, Y. Nakajima and M. Osame (1989). "Chronic inflammatory arthropathy associated with HTLV-I." Lancet 1(8635): 441.
Osame, M., K. Usuku, S. Izumo, N. Ijichi, H. Amitani, et al. (1986). "HTLV-I associated myelopathy, a new clinical entity." Lancet 1(8488): 1031-1032.
Poiesz, B. J., F. W. Ruscetti, A. F. Gazdar, P. A. Bunn, J. D. Minna and R. C. Gallo (1980). "Detection and isolation of type C retrovirus particles from fresh and cultured lymphocytes of a patient with cutaneous T-cell lymphoma." Proc Natl Acad Sci U S A 77(12): 7415-7419.
Poiesz, B. J., F. W. Ruscetti, J. W. Mier, A. M. Woods and R. C. Gallo (1980). "T-cell lines established from human T-lymphocytic neoplasias by direct response to T-cell growth factor." Proc Natl Acad Sci U S A 77(11): 6815-6819.
Roc, L., C. de Mendoza, M. Fernandez-Alonso, G. Reina, V. Soriano and H. N. Spanish (2019). "Rapid subacute myelopathy following kidney transplantation from HTLV-1 donors: role of immunosuppresors and failure of antiretrovirals." Ther Adv Infect Dis 6: 2049936119868028.
Soker, S., S. Takashima, H. Q. Miao, G. Neufeld and M. Klagsbrun (1998). "Neuropilin-1 is expressed by endothelial and tumor cells as an isoform-specific receptor for vascular endothelial growth factor." Cell 92(6): 735-745.
Uchiyama, T., J. Yodoi, K. Sagawa, K. Takatsuki and H. Uchino (1977). "Adult T-cell leukemia: clinical and hematologic features of 16 cases." Blood 50(3): 481-492.
Dickler, H. B., et al. (1973). "Lymphocyte binding of aggregated IgG and surface Ig staining in chronic lymphocytic leukaemia." Clin Exp Immunol 14(1): 97-106.
USPTO; Notice of Allowance dated May 18, 2020 in the U.S. Appl. No. 16/083,384.
USPTO; Final Office Action dated Jun. 2, 2020 in the U.S. Appl. No. 15/580,661
USPTO; Non-Final Office Action dated Jun. 1, 2020 in the U.S. Appl. No. 16/530,908.
CN; 1st Office Action in the CN Application No. 20170017712.6 dated May 8, 2020.
EPO; Office Action in the EPO Application No. 16808223.8 dated May 11, 2020.
Lee et al., "Lentiviral delivery of short hairpin RNAs protects CD4 cells from multiple clades and primary isolates of HIV." Blood, 2005, vol. 106(3):818-826. (Year: 2005).

Choi et al., "Multiplexing Seven miRNA-Based shRNAs to Suppress HIV Replication." Molecular Therapy, 2015, vol. 23(2):310-320. Supplementary materials.
Spartevello et al., Development of Lentiviral Vectors Simultaneously Expressing Multiple siRNAs Against CCR5, vif and tat/rev Genes for an HIV-1 Gene Therapy Approach, Molecular Therapy—Nucleic Acids, 2016, vol. 5:1-12.
USPTO; Restriction Requirement dated Jun. 15, 2020 in the U.S. Appl. No. 16/308,373.
USPTO; Restriction Requirement dated Jun. 26, 2020 in the U.S. Appl. No. 16/318,345.
USPTO; Office Action dated Jul. 6, 2020 in the U.S. Appl. No. 16/312,056.
JP; Japanese Office Action in the Application No. 2019-500475 dated Jun. 12, 2020.
Pallikkuth et al., "Human Immunodeficiency Virus (HIV) gag Anti-Specific T-Helper and Granule-Dependent CD8 T-Cell Activities in Exposed but Uninfected Heterosexual Partners of HIV Type 1-Infected Individuals in North India," Clinical and Vaccine Immunology, vol. 14(9) pp. 1196-1202, (2007).
USPTO; Non-Final Office Action dated Feb. 21, 2020 in the U.S. Appl. No. 16/076,655.
EPO; Extended European Supplementary Search Report dated Feb. 6, 2020 in the Application No. 17825011.4.
EPO; Extended European Supplementary Search Report dated Feb. 6, 2020 in the Application No. 17824652.6.
Oh et al. "Lentiviral Vector Design Using Alternative RNA Export Elements," Retrovirology, vol. 4:38, pp. 1-10, (2007).
PCT; International Preliminary Report on Patentability dated Oct. 8, 2019 in the Application No. PCT/US2018/025733.
PCT; International Search Report and Written Opinion of the International Search Report dated Jul. 22, 2019 in the Application No. PCT/US2019/024410.
USPTO; Notice of Allowance dated Nov. 27, 2019 in the U.S. Appl. No. 13/333,882.
Lin et al., "Up-Regulation of Bcl-2 is Required for the Progression of Prostate Cancer Cells from an Androgen-Dependent to an Androgen-Independent Growth Stage," Cell Research, vol. 17, pp. 531-536, (2007).
GenBank Sequence M65141.1 Retrieved from the Internet <URL: https://www.ncbi.ntm.nih.gov/nuccore/M65141.1. Especially Sequence, nt 301-420, (Retrieved Mar. 31, 2019).
PCT; International Search Report dated Apr. 12, 2019 in Application No. PCT/ US2018/053919.
PCT; Written Opinion dated Apr. 12, 2019 in Application No. PCT/US2018/053919.
USPTO; Non-Final Office Action dated Apr. 18, 2019 in U.S. Appl. No. 13/333,882.
USPTO; Restriction Requirement dated Jan. 29, 2020 in the U.S. Appl. No. 16/312,056.
EPO; Supplementary European Search Report dated Dec. 19, 2019 in the Application No. 16904834.5.
EPO; Supplementary European Search Report dated Dec. 19, 2019 in the Application No. 17810976.5.
USPTO; Notice of Allowance dated Jul. 10, 2020 in the U.S. Appl. No. 16/530,908.
USPTO; Final Office Action dated Jul. 27, 2020 in the U.S. Appl. No. 16/076,655.
JP; Japanese Office Action in the Application No. 2018-536892 dated Jun. 26, 2020.
Wang et al., "HIV Vaccine Research: The Challenge and the Way Forward," Journal of Immunology Research, vol. 2015, Article ID 503978, 5 pages.
Bourguigon et al., "Processing of blood samples influences PBMC viability and outcome of cell-mediated immune responses in antiretroviral therapy-naïve HIV-1-infected patients," Journal of Immunological Methods, vol. 414, p. 1-10 (2014).
Briz et al., "Validation of Generation 4 Phosphorus-Containing Polycationic Dendrimer for Gene Delivery Against HIV-1," Current Medical Chemistry, vol. 19, p. 5044-5051, (2012).

(56) References Cited

OTHER PUBLICATIONS

Anderson et al., "Preintegration HIV-1 Inhibition by a Combination Lentiviral Vector Containing a Chimeric TRIM5a Protein, a CCR5 shRNA, and TAR Decoy," Molecular Therapy, vol. 17, No. 12, p. 2103-2114, Dec. 2009.
JP; Japanese Office Action in the Application No. 2017-567175 dated Jun. 15, 2020.
EPO; Extended European Search Report in the Application No. 18736295.9 dated Aug. 20, 2020.
USPTO; Non-Final Office Action dated May 24, 2019 in U.S. Appl. No. 16/218,010.
USPTO; Notice of Allowance dated Jul. 3, 2019 in U.S. Appl. No. 16/182,443.
EPO; Extended Search Report dated Jun. 6, 2019 in EP Application No. 17739028.3.
PCT; International Search Report and Written Opinion in the PCT Application No. PCT/US2019/059828 dated Feb. 14, 2020.
USPTO; Final Office Action dated May 2, 2019 in U.S. Appl. No. 16/182,443.
USPTO; Non-Final Office Action dated May 7, 2019 in U.S. Appl. No. 16/008,991.
USPTO; Non-Final Office Action dated May 16, 2019 in U.S. Appl. No. 16/132,247.
Cronin et al., "Altering the Tropism of Lentiviral Vectors through Pseudotyping", Curr Gene Ther, Aug. 2005, vol. 5(4), pp. 687-398.
Cannon et al., "Pseudotype-dependent lentiviral transduction of astrocytes or neurons in the rat substantia nigra", Experimental Neurology, vol. 228, (Year: 2011), pp. 41-52, doi:10.1016/J.expneurol. 2010.10.016.
USPTO; Non-Final Office Action dated Nov. 18, 2020 in the U.S. Appl. No. 16/318,345.
USPTO; Restriction Requirement dated Nov. 19, 2020 in the U.S. Appl. No. 16/593,882.
USPTO; Non-Final Office Action dated Nov. 25, 2020 in the U.S. Appl. No. 16/943,800.
USPTO; Notice of Allowance dated Dec. 2, 2020 in the U.S. Appl. No. 16/076,655.
USPTO; Restriction Requirement dated Dec. 8, 2020 in the U.S. Appl. No. 16/563,738.
USPTO; Notice of Allowance dated Jan. 26, 2021 in the U.S. Appl. No. 16/593,882.
Nada et al., "Enhancing adoptive cancer immunotherapy with V$\gamma$2V$\delta$2 T cells through pulse zoledronate stimulation", Journal for Immunotherapy of Cancer, vol. 5, No. 1, (Feb. 21, 2017), pp. 1-23, (2017) DOI 10.1186/s40425-017-0209-6 the whole document.
Benyamine et al., "BTN3A molecules considerably improve V$\gamma$9V$\delta$2T cells-based immunotherapy in acute myeloid leukemia," Oncolmmunology, vol. 5, No. 10,10 pages, (Oct. 2, 2016), E1146843 the whole document.
Harly et al., "Key implication of CD277/butyrophilin-3 (BTN3A) in cellular stress sensing by a major human $\gamma\delta$ T-cell subset," American Society of Hematology, vol. 120, No. 11, (Sep. 13, 2012), pp. 2269-2279, XP055081172, ISSN: 0006-4971, DOI: 10.1182/blood-2012-05-430470 the whole document.
Wang et al., "Intravenous Delivery of SiRNA Targeting CD47 Effectively Inhibits Melanoma Tumor Growth and Lung Metastasis", Molecular Therapy, pp. 1919-1929, vol. 21, No. 10, Oct. 2013.
USPTO; Notice of Allowance dated Feb. 10, 2021 in the U.S. Appl. No. 16/943,800.
USPTO; Non-Final Office Action dated Feb. 19, 2021 in the U.S. Appl. No. 15/580,661.
USPTO; Final Office Action dated Feb. 26, 2021 in the U.S. Appl. No. 16/312,056.
USPTO; Corrected Notice of Allowance dated Mar. 3, 2021 in the U.S. Appl. No. 16/687,525.
USPTO; Non-Final Office Action dated Mar. 12, 2021 in the U.S. Appl. No. 16/563,738.
CN; 1st Office Action in the CN Application No. 202010396594.8 dated Jan. 15, 2021.
EP; Supplementary Search Report in the EP Application No. 18817253 dated Feb. 10, 2021.
JP; Office Action in the JP Application No. 2018-547354 dated Feb. 16, 2021.
JP; Office Action in the JP Application No. 2018-541270 dated Jan. 8, 2021.
Yang et al., "Construction of PARP-1 gene silencing cell lines by lentiviral-mediated RNA interference," School of Public Health, Guangdong Medical College, Abstract (2006).
Zhaobing Ding et al., "Liver-Directed, AAV-and Lentivirus-Mediated Gene Therapy in the Phenylketonuria Mouse Model Pah-enu2", Molecular Therapy, vol. 11, Supp. 1. (May 2005) XP055751452.
Ledley et al., "Retroviral-mediated gene transfer of human phenylalanine hydroxylase into NIH 3T3 and hepatoma cells", Proceedings of the National Academy of Sciences, vol. 83, No. 2. (Jan. 1, 1986), pp. 409-413, XP002583115.
Ledley et al., "Molecular biology of phenylalanine hydroxylase and phenylketonurina", Trends in Genetics, Elsevier Science Publishers B.V. Amsterdam, NL, vol. 1. (Jan. 1, 1985), pp. 309-313, XP025943064.
USPTO; Notice of Allowance dated Jan. 13, 2021 in the U.S. Appl. No. 16/687,525.
EP; Supplementary Search Report in the EP Application No. 187812888 dated Dec. 8, 2020.
JP; Final Office Action in the JP Application No. 2018-536892 dated Nov. 16, 2020.
Bergvall et al. "The E1 proteins", Virology 445; p. 35-56, (Year:2013).
McBride, A., "The Papillomavirus E2 proteins", Virology 445: p. 57-79, (Year: 2013).
Chiang C-m et al., "Viral E1 and E2 proteins support replication of homologous and heterologous papillomaviral origins." PNAS 89: p. 5799-5803, (Year: 1992).
Krajinovic et al., "Sequencing data on the long control region of human papillomavirus type 16." Journal of General Virology 72:2573-2576, (Year: 1991).
Seedorg et al., "Human Papillomavirus type 16 DNA sequence." Virology 145: p. 181-185, (Year: 1985).
Jaalouk, et al. "A Self-inactivating retrovector incorporating the IL-2 promoter for activation-induced transgene expression engineered t-cells," Virology Journal: p. 1-12, (Year: 2006).
USPTO; Non-Final Office Action dated Sep. 22, 2020 in the U.S. Appl. No. 16/308,373.
JP; Japanese Office Action in the JP Application No. 2018-563892 dated Oct. 14, 2020.
EP Search Report in European Application No. 19777212.2, dated Nov. 2, 2021, 8 pages.
JP Notice of Allowance in Japanese Application No. 2019-500475, dated Sep. 15, 2021, 6 pages (with English translation).
JP Office Action in Japanese Application No. 2019-536901, dated Nov. 19, 2021, 16 pages (with English translation).
Kaur et al., "Antigen stimulation induces HIV envelope gp120-specific CD4$^+$ T cells to secret CCR5 ligands and suppress HIV infection", Virology, Dec. 2007, 369(1): 214-225.
U.S. Non-Final Office Action in U.S. Appl. No. 16/312,056, dated Nov. 17, 2021, 26 pages.
Venturini et al., "Characterization of Human Immunodeficiency Virus Type 1 (HIV-1) Gag- and Gag Peptide-Specific CD4$^+$ T-Cell Clones from an HIX-a-Seronegative Donor following In Vitro Immunization", Journal of Virology, Jul. 2002, 76(14): 6987-6999.
EP Office Action in European Application No. 17750547.6, dated Apr. 29, 2022, 4 pages.
JP Office Action in Japanese Application No. 2019-500423, dated Apr. 27, 2022, 9 pages (with English translation).
JP; Office Action in the JP Application No. 2019-500475 dated Mar. 4, 2021.
JP; Office Action in the JP Application No. 2019-500423 dated Jun. 2, 2021.
EPO; Examination Report dated Oct. 7, 2021 in App. No. 16822021.8.
EP Office Action in European U.S. Appl. No. 16/822,021, dated Oct. 7, 2021, 4 pages.
JP Office Action in Japanese Application No. 2018-541270, dated Dec. 23, 2021, 19 pages (with English translation).

(56) References Cited

OTHER PUBLICATIONS

U.S. Non-Final Office Action in U.S. Appl. No. 16/312,056, dated Nov. 17, 2021, 32 pages.
Yokota, "Gene therapy of virus replication with RNAi", Virus, vol. 55, No. 1, pp. 1-8.
Anderson et al., Safety and Efficacy of a Lentiviral Vector Containing Three Anti-HIV Genes-CCR5 Ribozyme, Tat-Rev siRNA, and TAR Decoy-in SCID-hu Mouse-Derived T Cells, Mol. Ther., vol. 15, pp. 1182-1188, 2007.
EP Office Action in European U.S. Appl. No. 18/736,295, dated Jan. 25, 2023, 10 pages.
JP Notice of Allowance in Japanese Application No. 2019-536901, dated Mar. 3, 2023, 6 pages (with English translation).
JP Office Action in Japanese Application No. 2021-084813, dated Feb. 10, 2023, 10 pages (with English translation).
Kretova et al., Generation of Genetic Constructs that Simultaneously Express Several shRNAs, Biotechniques, vol. 52, 3 pages, 2012.
Spanevello et al., "Combinatorial RNA Interference as a Gene Therapy Strategy for HIV-1 Infection," Retrovirology, vol. 10, 2013.
U.S. Final Office Action in U.S. Appl. No. 16/312,056, dated Jan. 31, 2023, 36 pages.
IL Notice of Allowance in Israeli Application No. 284348, dated Oct. 23, 2022, 3 pages.
IN Office Action in Indian Application No. 201947000153, dated Oct. 28, 2022, 8 pages.
U.S. Final Office Action in U.S. Appl. No. 17/089,468, dated Nov. 1, 2022, 19 pages.
U.S. Notice of Allowance in U.S. Appl. No. 17/175,278, dated Nov. 9, 2022, 16 pages.
JP Notice of Allowance in Japanese Application No. 2018-541270, dated Aug. 31, 2022, 6 pages (with English translation).
[Online], "CD4+ T Cell Isolation Kit Human," Miltenyi Biotec, published online in 2015, 3 pages.
AU Office Action in Australian Application No. 2018205388, dated Mar. 3, 2023, 5 pages.
JP Office Action in Japanese Application No. 2020-551499, dated Mar. 10, 2023, 10 pages (with English translation).
JP Office Action in Application No. 2021-84813, dated Jun. 23, 2022, 6 pages.
Wolstein et al., "Preclinical Safety and Efficacy of an Anti-HIV-1 Lentiviral Vector Containing a Short Hairpin RNA to CCR5 and the C46 Fusion Inhibitor," Molecular Therapy—Methods & Clinical Development (2014).
Anderson et al., "HIV-1 Resistance Conferred by siRNA Cosuppression of CXCR4 and CCR5 Coreceptors by a Bispecific Lentiviral Vector," Aids Research and Therapy, 2:1, pp. 1-12, 2005.
Anderson et al., Specific Transduction of HIV-Susceptible Cells for CCR5 Knockdown and Resistance to HIV Infection: A Novel Method for Targeted Gene Therapy and Intracellular Immunization, J. Acquir, Immune. Defic. Syndr., vol. 52, No. 2 Oct. 1, 2009.
BR Office Action in App. No. BR112019014082-4, dated Jul. 26, 2022, 3 pages.
IL Office Action in App. No. 284348, dated Jun. 12, 2022, 3 pages.
JP Office Action in Japanese Application No. 2019-536901, dated Jul. 27, 2022, 12 pages.
CA; Office Action issued in Application No. 3048634 on Jan. 11, 2024.

* cited by examiner

SEQ ID NO: 1

Elongation Factor-1 alpha (EF1-alpha) promoter (ITALICS)

*ACCGGTGCCTAGAGAAGGTGGCGCGGGGTAAACTGGGAAAGTGATGTCGTGTACTGGCTCCGCCTTTTTCCCGAG*

*GGTGGGGGAGAACCGTATATAAGTGCAGTAGTCGCCGTGAACGTTCTTTTTCGCAACGGGTTTGCCGCCAGAACA*

*CAGGTAAGTGCCGTGTGTGGTTCCCGCGGGCCTGGCCTCTTTACGGGTTATGGCCCTTGCGTGCCTTGAATTACTT*

*CCACGCCCCTGGCTGCAGTACGTGATTCTTGATCCCGAGCTTCGGGTTGGAAGTGGGTGGGAGAGTTCGAGGCCT*

*TGCGCTTAAGGAGCCCCTTCGCCTCGTGCTTGAGTTGAGGCCTGGCCTGGGCGCTGGGGCCGCCGCGTGCGAATC*

*TGGTGGCACCTTCGCGCCTGTCTCGCTGCTTTCGATAAGTCTCTAGCCATTTAAAATTTTTGATGACCTGCTGCGAC*

*GCTTTTTTTCTGGCAAGATAGTCTTGTAAATGCGGGCCAAGATCGATCTGCACACTGGTATTTCGGTTTTTGGGGCC*

*GCGGGCGGCGACGGGGCCCGTGCGTCCCAGCGCACATGTTCGGCGAGGCGGGGCCTGCGAGCGCGGCCACCGA*

*GAATCGGACGGGGGTAGTCTCAAGCTGGCCGGCCTGCTCTGGTGCCTGGCCTCGCGCCGCCGTGTATCGCCCCGC*

*CCTGGGCGGCAAGGCTGGCCCGGTCGGCACCAGTTGCGTGAGCGGAAAGATGGCCGCTTCCCGGCCCTGCTGCA*

*GGGAGCTCAAAATGGAGGACGCGGCGCTCGGGAGAGCGGGCGGGTGAGTCACCCACACAAAGGAAAAGGGCCT*

*TTCCGTCCTCAGCCGTCGCTTCATGTGACTCCACGGAGTACGGGCGCCGTCCAGGCACCTCGATTAGTTCTCGAG*

*CTTTTGGAGTACGTCGTCTTTAGGTTGGGGGGAGGGGTTTTATGCGATGGAGTTTCCCCACACTGAGTGGGTGGA*

*GACTGAAGTTAGGCCAGCTTGGGCACTTGATGTAATTCTCCTTGGAATTTGCCCTTTTTGAGTTTGGATCTTGGTTC*

*ATTCTCAAGCCTCAGACAGTGGTTCAAAGTTTTTTTCTTCCATTTCAGGTGTCGTGAGGAATTGGCGAAGCTAATTC*

TGCAGATTCGACTGTACA<u>AGGTATATTGCTGTTGACAGTGAGCGACTGTAAACTGAGCTTGCT</u> <span style="font-size:smaller">miR30 CCR5 start</span>

<u>CTACTGTGAAGCCACAGATGGGTAGAGCAAGCACAGTTTACCGCTGCCTACTGCCTCGG</u>

<u>ACTTCAAGGGGCTT</u>cccggg<u>CATCTCCATGGCTGTACCACCTTGTCGGGGGATGTGTACTT</u> <span style="font-size:smaller">miR30 CCR5 end    miR21 Vif start</span>

<u>CTGAACTTGTGTTGAATCTCATGGAGTTCAGAAGAACACATCCGCACTGACATTTTGGTA</u>

<u>TCTTTCATCTGACCA</u>gctagc<u>GGGCCTGGCTCGAGCAGGGGGCGAGGGATTCCGCTTCTTC</u> <span style="font-size:smaller">miR21 Vif end    miR185 Tat start</span>

<u>CTGCCATAGCGTGGTCCCCTCCCTATGGCAGGCAGAAGCGGCACCTTCCCTCCCAATGA</u>

<u>CCGCGTCTTCGTC</u>gcggccgctcgagcatgcat <span style="font-size:smaller">miR185 Tat end</span>

Figure 4

SEQ ID NO: 2

TREX1 - human; open reading frame; three prime repair exonuclease 1

```
  1 atgcagaccc tcatcttttt cgacatggag gccactggct tgcccttctc ccagcccaag
 61 gtcacggagc tgtgcctgct ggctgtccac agatgtgccc tggagagccc ccccacctct
121 caggggccac ctcccacagt tcctccacca ccgcgtgtgg tagacaagct ctccctgtgt
181 gtgctccgg ggaaggcctg cagccctgca gccagcgaga tcacaggtct gagcacagct
241 gtgctggcag cgcatgggcg tcaatgtttt gatgacaacc tggccaacct gctcctagcc
301 ttcctgcggc gccagccaca gccctggtgc ctggtggcac acaatggtga ccgctacgac
361 ttcccctgc tccaagcaga gctggctatg ctgggcctca ccagtgctct ggatggtgcc
421 ttctgtgtgg atagcatcac tgcgctgaag gccctggagc gagcaagcag ccctcagaa
481 cacggcccaa ggaagagcta cagcctaggc agcatctaca ctcgcctgta tgggcagtcc
541 cctccagact cgcacacggc tgagggtgat gtcctggccc tgctcagcat ctgtcagtgg
601 agaccacagg ccctgctgcg gtgggtggat gctcacgcca ggcctttcgg caccatcagg
661 cccatgtatg gggtcacagc ctctgctagg accaagccaa gaccatctgc tgtcacaacc
721 actgcacacc tggccacaac caggaacact agtcccagcc ttcgagagag cagggtacc
781 aaggatcttc ctccagtgaa ggaccctgga gccctatcca gggaggggct gctggcccca
841 ctgggtctgc tggccatcct gaccttggca gtagccacac tgtatggact atccctggcc
901 acacctggcg attaa
```

Figure 9

SEQ ID NO: 3

TREX2 - human; open reading frame; three prime repair exonuclease 2
```
   1 caccttggtc acactccaga gctcgcttca tccccacgag cggcacctga tctccagtga
  61 cggggagact gaggcctggc aaagaggacc tgttgccttt gtgtaactgg ccccagcatg
 121 ggggaggcat tggccccagc atggggagg cattgacccc aggcctgcca ggcctggcag
 181 ccacagcctg gctaggtgga ggttactgcc ttccgcacca ctctggcttc ctcccgtgc
 241 ctgtgaagag ctcggggcct gcttcctaat ttgtaaacac ggggcgtgtg tctcagtggc
 301 tgtgagctag cgaggggtg gcgagcgagc cggctgcgca ggtcctgagg cccaggcct
 361 cattgttggc caacaggcag ctggggcgg gctgcggccg ctgattaaag gccgcctaga
 421 gcagcctgtg tggcgacagg tgcccagaag cccaggaagc cggtcagtgc ccgccccagt
 481 cctcagggtt tgtgcctctc gctcggacag tttgaggact tgctatcccc gtgggaacat
 541 caccatgtcc gaggcacccc gggccgagac ctttgtcttc ctggacctgg aagccactgg
 601 gctccccagt gtggagcccg agattgccga gctgtccctc tttgctgtcc accgctcctc
 661 cctggagaac ccggagcacg acgagtctgg tgccctagta ttgcccgggg tcctggacaa
 721 gctcacgctg tgcatgtgcc cggagcgcc cttcactgcc aaggccagcg agatcacggg
 781 cctgagcagt gagggcctgg cgcgatgccg gaaggctggc tttgatgcg ccgtggtgcg
 841 gacgctgcag gccttcctga ccgccaggc agggcccatc tgccttgtgg cccacaatgg
 901 ctttgattat gatttcccc tgctgtgtgc cgagctgcgg cgcctgggtg ccgcctgcc
 961 ccgggacact gtctgcctgg acacgctgcc ggccctgcgg ggcctggacc gcgcccacag
1021 ccacggcacc cgggcccggg gccgcaggg ttacagcctc ggcagcctct tccaccgcta
1081 cttccgggca gagccaagcg cagcccactc agccgagggc gacgtgcaca ccctgctcct
1141 gatcttcctg cacgcgccg cagagctgct cgcctggcc gatgagcagg cccgtgggtg
1201 ggcccacatc gagcccatgt acttgccgcc tgatgacccc agcctggagg cctga
```

Figure 9 Con't

SEQ ID NO: 4

SAMHD1 - human; open reading frame; SAM domain and HD domain-containing protein

```
   1 attgcgcctg cgcagggagc ccaaggcaag agccgctagg ctgccctgcc cgaagggctc
  61 aactgtcagt gagcctgcgc aggaggccaa taggctgcca atactccttg gactcccgc
 121 cagggccctg ctgtcagtgc gcctgcgcgc gggtccggcg ccgaggttct tgactgctgt
 181 gccggacgcc aggtgtagcc atgcagcgag ccgattccga gcagccctcc aagcgtcccc
 241 gttgcgatga cagcccgaga accccctcaa acaccccttc cgcagaggca gactggtccc
 301 cgggcctgga actccatccc gactacaaga catgggtcc ggagcaggtg tgctccttcc
 361 tcaggcgcgg tggcttgaa gagccggtgc tgctgaagaa catccgagaa atgaaatca
 421 caggcgcatt actgccttgt ctgatgagt ctcgttttga aaatcttgga gtaagttcct
 481 tggggggagag gaagaagctg cttagttata tccagcgatt ggttcaaatc cacgttgata
 541 caatgaaggt aattaatgat cctatccatg gccacattga gtccaccct ctcctcgtcc
 601 gaatcattga tacacctcaa tttcaacgtc ttcgatacat caaacagctg ggaggtggtt
 661 actatgtttt tccaggagct tcacacaatc gatttgagca tagtctaggg gtggggtatc
 721 tagcaggatg tctagttcac gcactgggtg aaaaacaacc agagctgcag ataagtgaac
 781 gagatgttct ctgtgttcag attgctggac tttgtcatga tctcggtcat gggccatttt
 841 ctcacatgtt tgatggacga tttattccac ttgctcgccc ggaggtgaaa tggacgcatg
 901 aacaaggctc agttatgatg tttgagcacc ttattaattc taatggaatt aagcctgtca
 961 tggaacaata tggtctcatc cctgaagaag atatttgctt tataaaggaa caaattgtag
1021 gaccacttga atcacctgtc gaagattcat tgtggccata taagggcgt cctgaaaaca
1081 aaagcttcct ttatgagata gtatctaata aaagaaatgg cattgatgtg acaaatggg
1141 attattttgc cagggactgc catcatcttg aatccaaaa taattttgat tacaagcgct
1201 ttattaagtt tgcccgtgtc tgtgaagtag acaatgagtt gcgtatttgt gctagagata
1261 aggaagttgg aaatctgtat gacatgttcc acactcgcaa ctctttacac cgtagagctt
1321 atcaacacaa agttggcaac attattgata caatgattac agatgcttc ctcaaagcag
1381 atgactacat agagattaca ggtgctggag gaaaaaagta tcgcatttct acagcaattg
1441 acgacatgga agcctatact aagctgacag ataacatttt tctggagatt ttatactcta
1501 ctgatcccaa attgaaagac gcacgagaga ttttaaaaca aattgaatac cgtaatctat
1561 tcaagtatgt gggtgagacg cagccaacag gacaaataaa gattaaaagg gaggactatg
1621 aatctcttcc aaaagaggtt gccagtgcta aacccaaagt attgctagac gtgaaactga
1681 aggctgaaga ttttatagtg gatgttatca acatggatta tggaatgcaa gaaaagaatc
1741 caattgatca tgttagcttc tattgtaaga ctgcccccaa cagagcaatc aggattacta
1801 aaaaccaggt ttcacaactt ctgccagaga aatttgcaga gcagctgatt cgagtatatt
1861 gtaagaaggt ggacagaaag agtttgtatg ccgcaagaca atatttgtt cagtggtgtg
1921 cagacagaaa tttcaccaag ccgcaggatg gcgatgttat agccccactc ataacacctc
1981 aaaaaaagga atggaacgac agtacttcag tccaaaatcc aactcgcctc cgagaagcat
2041 ccaaaagcag agtccagctt tttaagatg acccaatgtg aatgtctgta gtcagttgtt
2101 tacaaactcc ctctcctgca caattcattt agaggcttca atcatagaat tctgcaaatt
2161 aatgacaact catgctttaa ttttgtattt tgaatgtaca cgcatgctga agctaagtaa
2221 cttttaatca aagaaataag atggtattag gcaaatctta ctatactatg aaaagcatta
2281 ccttgcctat ttttaatatt attaaagcct ttctccttca gtagtctatt ttcttagaat
2341 aacaactctt ttatctattc tgaactctat ttttttttctt ttttaagaga caaggttttg
2401 ctctgttgcc cagcttggac tcgaactttc ctgggctcaa gcgacctcc tgcctcagcc
2461 ccccaagtag ctgggactaa agtcatgtgc caccacacc agcttactct gaacttttat
2521 gacagatgat tgttttttgt tttaatgta gaatgagac aagggtacaa attggaacta
2581 gaaattgaca ttgtcattga caaacatggc taaaaacaaa acatcaaatc ctgcccgt
2641 gaagagttcc ctgtcacctc aagtttgagg atagtcctct aagagtgacc taagcataag
2701 tgaaagacac ctcccctcac ccttctagcc cctacaagg tgccaggttg ggtaaagag
2761 ttggagatga tggccaggag tggcctccaa cacgctggtg agaggcctga ttaggttttg
2821 gggaagatct gagagctctg gcctcttcgt gagtggaaca taaagccgcc tcttgttggg
2881 agatcctacc ccagtgacag aggaatcccc caaactaggc tgtgccctgg ctccgtggcg
2941 gctccagacc cgggtagtgc ctttgtcccc tgaatactca ctccccggt ccagagggcc
3001 ttcccactgc ccagcctgga gaaggcctcc cctgacctgc tctctcagta tcctggagag
3061 ctggccagag gccatcacag gcatcatcct cagagctcct cagacctggg actttgtttt
3121 tgctggttca gtgcattttg tgtatttaag agcaaacact agccaggcgt ggcggcgtgt
```

SEQ ID NO: 5
MxA - human; open reading frame; influenza virus resistance 1

```
   1 cgagcagaaa tgaaaccgaa actgaattgt ccgggaaatt cgcggtgggg gcggagagcg
  61 cagggagaag taagcccagt gcaggatcct gaggcccgtg tttgcaggac cagggccggc
 121 cttccgattc cccattcatt ccagaagcac cgaaccacgc tgtgccgga tcccaagtgc
 181 agcggcaccc agcgtgggcc tggggttgcc ggttgacccg gtcctcagcc tggtagcaga
 241 ggccaggcca gtgccacaag gcacctaagt ccacctgggc ctggagcagg acaggttgca
 301 aaagaaaata tctcgggacc cccaaactcc ttatgctaag ggaaacatcg agcctgggaa
 361 ctgagccatc aacgctgcca ttcttttcc caaacagaac ctgttgtca gaggtacacc
 421 cagagcaact ccacaccggg tgcatgccac agcaactcca tcttaaatag gagctggtaa
 481 aacgaggctg ataccctactg ggctgcattc ccagacggca tagcgaggag gtgctgaaga
 541 gcgcaggttt ggagaatgat cacctggatt ggaaccatag ctctaccaat atggaaccca
 601 gctccttagg cctcggtctt ctcatggaga acatggtgtg ataatcctac tcctctggga
 661 gggtggctgt taagccttgg accgcagttg ccggccagga tcccagtgt cacggtggac
 721 acgcctccct cgcgccttg ccgcccacct gctcacccag tcagggct ttggaattct
 781 gtggccacac tgcgaggaga tcggttctgg gtcggaggct acaggaagac tcccactccc
 841 tgaaatctgg agtgaagaac gccgccatcc agccaccatt ccaaggaggt gcaggagaac
 901 agctctgtga taccatttaa cttgttgaca ttacttttat ttgaaggaac gtatattaga
 961 gcttactttg caaagaagga agatggttgt ttccgaagtg acatcgcaa agctgatcc
1021 agctgctgca tcccacccctc tattactgaa tggagatgct actgtggccc agaaaaatcc
1081 aggctcggtg gctgagaaca acctgtgcag ccagtatgag gagaaggtgc gccctgcat
1141 cgacctcatt gactccctgc gggctctagg tgtggagcag gacctggccc tgccagccat
1201 cgccgtcatc ggggaccaga gctcggcaa gagctccgtg ttggaggcac tgtcaggagt
1261 tgcccttccc agaggcagcg ggatcgtgac cagatgcccg ctggtgctga aactgaagaa
1321 acttgtgaac gaagataagt ggagaggcaa ggtcagttac caggactacg agattgagat
1381 ttcggatgct tcagaggtag aaaaggaaat taataaagcc cagaatgcca tcgccgggga
1441 aggaatggga atcagtcatg agctaatcac cctggagatc agctcccgag atgtcccgga
1501 tctgactcta atagaccttc ctggcataac cagagtggct gtgggcaatc agctgctga
1561 cattgggtat aagatcaaga cactcatcaa gaagtacatc cagaggcagg agacaatcag
1621 cctggtggtg gtccccagta atgtggacat cgccaccaca gaggctctca gcatggccca
1681 ggaggtggac ccgaggggag acaggaccat cggaatcttg acgaagcctg atctggtgga
1741 caaggaact gaagacaagg ttgtggacgt ggtgcggaac ctgtgttcc acctgaagaa
1801 gggttacatg attgtcaagt gccgggcca gcaggagatc caggaccagc tgagcctgtc
1861 cgaagccctg cagagagaga agatcttctt tgagaaccac ccatatttca gggatctgct
1921 ggaggaagga aaggccacgg ttccctgcct ggcagaaaaa cttaccagcg agctcatcac
1981 acatatctgt aaatctctgc ccctgttaga aatcaaatc aaggagactc accagagaat
2041 aacagaggag ctacaaaagt atggtgtcga cataccggaa gacgaaaatg aaaaaatgtt
2101 cttcctgata gataaagtta atgcctttaa tcaggacatc actgctctca tgcaaggaga
2161 ggaaactgta ggggaggaag acattcggct gtttaccaga ctccgacacg agttccacaa
2221 atggagtaca ataattgaaa acaattttca agaaggccat aaaattttga gtagaaaaat
2281 ccagaaattt gaaaatcagt atcgtggtag agagctgcca ggctttgtga attacaggac
2341 atttgagaca atcgtgaaac agcaaatcaa ggcactggaa gagccggctg tggatatgct
2401 acacaccgtg acggatatgg tccggcttgc tttcacagat gtttcgataa aaattttga
2461 agagtttttt aacctccaca gaaccgccaa gtccaaaatt gaagacatta gagcagaaca
2521 agagagagaa ggtgagaagc tgatccgcct ccacttccag atggaacaga ttgtctactg
2581 ccaggaccag gtatacaggg gtgcattgca gaaggtcaga gagaaggagc tggaagaaga
2641 aaagaagaag aaatcctggg attttgggc tttccagtcc agctcggcaa cagactcttc
2701 catggaggag atctttcagc cctgatggc ctatcaccag gaggccagca gcgcatctc
2761 cagccacatc cctttgatca tccagttctt catgctccag acgtacggcc agcagcttca
2821 gaaggccatg ctgcagctcc tgcaggacaa ggacacctac agctggctcc tgaaggagcg
2881 gagcgacacc agcgacaagc ggaagttcct gaaggagcgg cttgcacggc tgacgcaggc
2941 tcggcgccgg cttgccagt cccggtta ccacactct gtccagcccc gtagacgtgc
3001 acgcacactg tctgccccg ttcccggta ccactggac tgacacttg agtgctcagt
3061 agtcagactg gatagtccgt ctctgcttat ccgttagccg tggtgattta gcaggaagct
3121 gtgagagcag tttggtttct agcatgaaga cagagcccca ccctcagatg cacatgagct
3181 ggcgggattg aaggatgctg tcttcgtact gggaaaggga ttttcagccc tcagaatcgc
3241 tccaccttgc agctctcccc ttctctgtat tcctagaaac tgacacatgc tgaacatcac
```

Figure 9 Con't

SEQ ID NO: 6

MxB - human; open reading frame

```
   1 aagagatgat ttctccatcc tgaacgtgca gcgagcttgt caggaagatc ggaggtgcca
  61 agtagcagag aaagcatccc ccagctctga cagggagaca gcacatgtct aaggcccaca
 121 agccttggcc ctaccggagg agaagtcaat tttcttctcg aaaatacctg aaaaaagaaa
 181 tgaattcctt ccagcaacag ccaccgccat tcgcacagt gccaccacaa atgatgtttc
 241 ctccaaactg gcaggggca gagaaggacg ctgctttcct cgccaaggac ttcaactttc
 301 tcactttgaa caatcagcca ccaccaggaa acaggagcca accaagggca atggggcccg
 361 agaacaacct gtacagccag tacgagcaga aggtgcgccc ctgcattgac ctcatcgact
 421 ccctgcgggc tctgggtgtg agcaggacc tggccctgcc agccatcgcc gtcatcgggg
 481 accagagctc gggcaagagc tctgtgctgg aggcactgtc aggagtcgcg cttcccagag
 541 gcagcggaat cgtaaccagg tgtccgctgg tgctgaaact gaaaaagcag ccctgtgagg
 601 catgggccgg aaggatcagc taccggaaca ccgagctaga gcttcaggac cctggccagg
 661 tggagaaaga gatacacaaa gcccagaacg tcatggccgg aatggccgg ggcatcagcc
 721 atgagctcat cagcctggag atcacctccc ctgaggttcc agacctgacc atcattgacc
 781 ttcccggcat caccagggtg gctgtgaca accagccccg agacatcgga ctgcagatca
 841 aggctctcat caagaagtac atccagaggc agcagacgat caacttggtg gtggttccct
 901 gtaacgtgga cattgccacc acggaggcgc tgagcatggc ccatgaggtg gacccggaag
 961 gggacaggac catcggtatc ctgaccaaac cagatctaat ggacagggc actgagaaaa
1021 gcgtcatgaa tgtggtgcgg aacctcacgt accccctcaa gaaggctac atgattgtga
1081 agtgccgggg ccagcaggag atcacaaaca ggctgagctt ggcagaggca accaagaaag
1141 aaattacatt ctttcaaaca catccatatt tcagagttct cctggaggag ggtcagcca
1201 cggttcccg actggcagaa agacttacca ctgaactcat catgcatatc caaaaatcgc
1261 tccgttgtt agaaggacaa ataagggaga gccaccagaa ggcgaccgag gagctgcggc
1321 gttgcgggc tgacatcccc agccaggagg ccgacaagat gttctttcta attgagaaaa
1381 tcaagatgtt taatcaggac atcgaaaagt tagtagaagg agaagaagtt gtaagggaga
1441 atgagacccg tttatacaac aaaatcagag aggattttaa aaactgggta ggcatacttg
1501 caactaatac ccaaaaagtt aaaaatatta tccacgaaga agttgaaaaa tatgaaaagc
1561 agtatcgagg caaggagctt ctgggatttg tcaactacaa gacatttgag atcatcgtgc
1621 atcagtacat ccagcagctg gtggagcccg cccttagcat gtccagaaa gccatggaaa
1681 ttatccagca agctttcatt aacgtggcca aaaaacattt tggcgaattt ttcaacctta
1741 accaaactgt tcagagcacg attgaagaca taaaagtgaa acacacagca aaggcagaaa
1801 acatgatcca acttcagttc agaatggagc agatggtttt ttgtcaagat cagatttaca
1861 gtgttgttct gaagaaagtc cgagaagaga ttttaaccc tctggggacg ccttcacaga
1921 atatgaagtt gaactctcat tttcccagta atgagtcttc ggttcctcc tttactgaaa
1981 taggcatcca cctgaatgcc tacttcttgg aaaccagcaa acgtctgcc aaccagatcc
2041 catttataat tcagtatttt atgctccgag agaatggtga ctccttgcag aaagcctga
2101 tgcagatact acaggaaaaa aatcgctatt ctggctgct tcaagagcag agtgagaccg
2161 ctaccaagag aagaatcctt aaggagagaa tttaccggct cactcaggcg cgacacgcac
2221 tctgtcaatt ctccagcaaa gagatccact gaagggcggc gatgcctgtg gttgtttct
2281 tgtgcgtact cattcattct aaggggagtc ggtgcaggat gccgcttctg ctttggggcc
2341 aaactcttct gtcactatca gtgtccatct ctactgtact ccctcagcat cagagcatgc
2401 atcaggggtc cacacaggct cagctctctc caccaccag ctcttccctg accttcacga
2461 agggatggct ctccagtcct tgggtcccgt agcacacagt tacagtgtcc taagatactg
2521 ctatcattct tcgctaattt gtatttgtat tccttcccc ctacaagatt atgagacccc
2581 agaggggaa ggtctgggtc aaattcttct tttgtatgtc cagtctcctg cacagcacct
2641 gcagcattgt aactgcttaa taaatgacat ctcactgaac gaatgagtgc tgtgtaagtg
2701 atggagatac ctgaggctat tgctcaagcc caggccttgg acatttagtg actgttagcc
2761 ggtccctttc agatccagtg ccatgcccc ctgcttccca tggttcactg tcattgtgtt
2821 tcccagcctc tccactccc cgccagaaag gagcctgagt gattctcttt tcttcttgtt
2881 tccctgatta tgatgagctt ccattgttct gttaagtctt gaagaggaat ttaataaagc
2941 aagaaactt tttaaaaacg t
```

SEQ ID NO: 7

APOBEC3G - human; open reading frame; apolipoprotein B mRNA editing enzyme, catalytic polypeptide-like 3G (APOBEC3G)

```
   1 gtgctctgct ggctcagcct ggtgtggacc cacctcccgg gcgctggctg caatgacttt
  61 ctctttccct ttgcaattgc cttgggtcct gccgcacaga gcggcctgtc tttatcagag
 121 gtccctctgc caggggagg gccccagaga aaaccagaaa gagggtgaga gactgaggaa
 181 gataaagcgt cccagggcct cctacaccag cgcctgagca ggaagcggga ggggccatga
 241 ctacgaggcc ctggaggtc actttaggga gggctgtcct aaaaccagaa gcttggagca
 301 gaaagtgaaa ccctggtgct ccagacaaag atcttagtcg ggactagccg gccaaggatg
 361 aagcctcact tcagaaacac agtggagcga atgtatcgag acacattctc ctacaacttt
 421 tataatagac ccatcctttc tgtcggaat accgtctggc tgtgctacga agtaaaaca
 481 aagggtccct caaggccccc tttggacgca aagatctttc gaggccaggt gtattccgaa
 541 cttaagtacc acccagagat gagattcttc cactggttca gcaagtggag gaagctgcat
 601 cgtgaccagg agtatgaggt cacctggtac atatcctgga gccctgcac aaagtgtaca
 661 agggatatgg ccacgttcct ggccgaggac cgaaggtta ccctgaccat ctttgttgcc
 721 cgcctctact acttctggga cccagattac caggaggcgc ttcgcagcct gtgtcagaaa
 781 agagacggtc cgcgtgccac catgaagatc atgaattatg acgaatttca gcactgttgg
 841 agcaagttcg tgtacagcca aagagagcta tttgagcctt ggaataatct gcctaaatat
 901 tatatattac tgcacatcat gctgggggag attctcagac actcgatgga tccacccaca
 961 ttcactttca actttaacaa tgaaccttgg gtcagaggac ggcatgagac ttacctgtgt
1021 tatgaggtgg agcgcatgca caatgacacc tgggtcctgc tgaaccagcg cagggctttt
1081 ctatgcaacc aggctccaca taaacacggt tccttgaag gccgccatgc agagctgtgc
1141 ttcctggacg tgattccctt ttggaagctg gacctggacc aggactacag ggttacctgc
1201 ttcacctcct ggagccctg cttcagctgt gccagaaa tggctaaatt catttcaaaa
1261 aacaaacacg tgagcctgtg catcttcact gcccgcatct atgatgatca aggaagatgt
1321 caggaggggc tgcgcaccct ggccgaggct ggggccaaaa tttcaataat gacatacagt
1381 gaatttaagc actgctggga caccttgtg gaccaccagg atgtccctt ccagccctgg
1441 gatggactag atgagcacag ccaagacctg agtgggaggc tgcgggccat tctccagaat
1501 caggaaaact gaaggatggg cctcagtctc taaggaaggc agagacctgg gttgagcctc
1561 agaataaaag atcttcttcc aagaaatgca acaggctgt tcaccaccat ctccagctga
1621 tcacagacac cagcaaagca atgcactcct gaccaagtag attcttttaa aaattagagt
1681 gcattacttt gaatcaaaaa tttatttata tttcaagaat aaagtactaa gattgtgctc
1741 aatacacaga aaagtttcaa acctactaat ccagcgacaa tttgaatcgg ttttgtaggt
1801 agaggaataa aatgaaatac taaatctttc tgtaaaaaaa aaaaaaaa
```

SEQ ID NO: 8

TRIM5 alpha - human; open reading frame; tripartite motif containing 5 (TRIM5)

```
   1 agtttatctt tcactttcct gccctgagtg tgagcaagaa tttcctgcgg ttcctctagg
  61 aaaattcctt tgtgcagatc aggcccgtgg attggtgagt gaatcctaac cacgtcttcc
 121 ctggcctgtc ttcactcttc tccccagaat caccacttct gcactggtgt ctgaaggtgt
 181 attgagtgat tttgtggagg gcagaagtag gaagtctttg ggacaaaact gtatttacct
 241 tgggatctgt gaacaagagg aacctcagca gccaggacag gcaggagcag tggaatagct
 301 actatggctt ctggaatcct ggttaatgta aaggaggagg tgacctgccc catctgcctg
 361 gaactcctga cacaacccct gagcctggac tgcggccaca gcttctgcca agcatgcctc
 421 actgcaaacc acaagaagtc catgctagac aaggagaga gtagctgccc tgtgtgccgg
 481 atcagttacc agcctgagaa catacggcct aatcggcatg tagccaacat agtggagaag
 541 ctcagggagg tcaagttgag cccagagggg cagaaagttg atcattgtgc acgccatgga
 601 gagaaacttc tactcttctg tcaggaggac gggaaggtca tttgctggct tgtgagcgg
 661 tctcaggagc accgtggtca ccacacgttc ctcacagagg aggttgcccg ggagtaccaa
 721 gtgaagctcc aggcagctct ggagatgctg aggcagaagc agcaggaagc tgaagagtta
 781 gaagctgaca tcagagaaga gaaagcttcc tggaagactc aaatacagta tgacaaaacc
 841 aacgtcttgg cagattttga gcaactgaga gacatcctgg actgggagga gagcaatgag
 901 ctgcaaaacc tggagaagga ggaggaagac attctgaaaa gccttacgaa ctctgaaact
 961 gagatggtgc agcagaccca gtccctgaga gagctcatct cagatctgga gcatcggctg
1021 cagggtcag tgatggagct gcttcagggt gtggatggcg tcataaaaag gacggagaac
1081 gtgaccttga agaagccaga aactttccca aaaaatcaaa ggagagtgtt tcgagctcct
1141 gatctgaaag gaatgctaga agtgtttaga gagctgacag atgtccgacg ctactgggtt
1201 gatgtgacag tggctccaaa caacatttca tgtgctgtca tttctgaaga taagagacaa
1261 gtgagctctc cgaaaccaca gataatatat ggggcacgag ggacaagata ccagacattt
1321 gtgaatttca attattgtac tggcatcctg gctctcaaa gtatcacatc agggaaacat
1381 tactgggagg tagacgtgtc caagaaaact gcttggatcc tgggggtatg tgctggcttc
1441 caacctgatg caatgtgtaa tattgaaaaa aatgaaaatt atcaacctaa atacggctac
1501 tgggttatag gttagagga aggagttaaa tgtagtgctt tccaggatag ttccttccat
1561 actccttctg ttcctttcat tgtgccctc tctgtgatta tttgtcctga tcgtgttgga
1621 gttttcctag actatgaggc ttgcactgtc tcattcttca atatcacaaa ccatggattt
1681 ctcatctata agtttctca ctgttctttt tctcagcctg tatttccata tttaaatcct
1741 agaaaatgtg gagtcccat gactctgtgc tcaccaagct cttgaacctt cttacacact
1801 cagcccttc tgtacagcac ctcttgtcca ggtgcatctc atacacctga actcatttgc
1861 atcatttaa ccatctttc cttgctgtct cccttctttc tatttgaacg tccttcactc
1921 atcagtaaaa tgtaataatt gccttgtgcc atattgtccc caatatttta ttgacatttg
1981 atagcaattt ttttcatcat tttccgtact cctaaggaaa actgacctat acctcataaa
2041 atgagaccgc tatttaggta ttacttctgc cagatattta tcacccaatt gcctctgaca
2101 ctgactaaga agatgaagaa aagcttttca acagcctttc tatatcatcg tgtgataatt
2161 gttcaccaat gaatgagtcc ttagccctgt gtcagtttac cctcgatgcc cttatttgtg
2221 agttaaagag aaaatatcat aaatggtata ctcttaagta tagaggtttt gtatctagag
2281 gatctcagtt caactcctgt ctctccatat accagcagtg taactgtgaa taacatactt
2341 aaatggctgt gcttatttcc ttttcttttc tttttcttt tttttttttt ttgagatgaa
2401 gttttgctct tgttcccag gctggagtgc aatggcacga tctcggttca ctgcaacctc
2461 cacctctcag attcaagcaa ttctcctgcc tcagcctccc aagtagctgg gattacaggt
2521 gcccaccacc accctggct aaatttgtat tttcagtaga cgcgggtt ccccatgttg
2581 gttaggctcg tctagaacct ctgacctcag gtgatccacc cgcctcggcc tcccaaagtg
2641 ctgggattac aggcgtgagc cacggcgcc agcctgtgct tatttcttta aataatttt
2701 tgtattaaaa acttcacatt aaataagtgc taatgtttta ttgcatagta gggtgactag
2761 agttaacaat aacctattgc atatattttg aaatagctag aagagaggat tttgaaagtt
2821 ctcaacacaa agaaatgaca catatttgag gtgatggata tgctaattac cctggttcgg
2881 ttattacgca atgtatacat gtatcaaaac atcacactgt accacataaa tatgtatatt
2941 tattatttgt caattaaaag caaataaaa caaaaaacct tcatctaata ctttggatca
3001 ttgtgaaaaa ataaattcct gaagtataaa gcatctatct aagtgtcttg atctaataag
3061 tacttgttct acaaattatt gaaaaacata aactctgtta atgtctcatg gaacaggttg
3121 tgcttcagg gaaactagga ttggatttac taaattctca ttttttagat ctcagatact
3181 actgtcaaaa tgacttcaat tctgccttct atatataata cacacatata tttaggattt
```

SEQ ID NO: 9

Tetherin (BST2) - human; open reading frame

```
   1 ataaggggt ggcccgtaga agattccagc accctcccct aactccaggc cagactcctt
  61 tcagctaaag gggagatctg gatggcatct acttcgtatg actattgcag agtgcccatg
 121 gaagacgggg ataagcgctg taagcttctg ctggggatag gaattctggt gctcctgatc
 181 atcgtgattc tggggtgcc cttgattatc ttcaccatca aggccaacag cgaggcctgc
 241 cggacggcc ttcgggcagt gatggagtgt cgcaatgtca cccatctcct gcaacaagag
 301 ctgaccgagg cccagaaggg ctttcaggat gtggaggccc aggccgccac ctgcaaccac
 361 actgtgatgg ccctaatggc ttccctggat gcagagaagg cccaaggaca aaagaaagtg
 421 gaggagcttg agggagagat cactacatta aaccataagc ttcaggacgc gtctgcagag
 481 gtggagcgac tgagaagaga aaaccaggtc ttaagcgtga gaatcgcgga caagaagtac
 541 taccccagct cccaggactc cagctccgct gcggcgcccc agctgctgat tgtgctgctg
 601 ggcctcagcg ctctgctgca gtgagatccc aggaagctgg cacatcttgg aaggtccgtc
 661 ctgctcggct tttcgcttga acattccctt gatctcatca gttctgagcg ggtcatgggg
 721 caacacggtt agcggggaga gcacggggta gccggagaag ggcctctgga gcaggtctgg
 781 agggccatg gggaagtcct gggtgtgggg acacagtcgg gttgacccag ggctgtctcc
 841 ctccagagcc tccctccgga caatgagtcc ccctcttgt ctcccaccct gagattgggc
 901 atgggtgcg gtgtggggg catgtgctgc ctgttgttat gggttttttt tgcgggggg
 961 gttgcttttt tctgggtct ttgagctcca aaaataaac acttcctttg agggagagca
1021 cacctgaaaa aaaaaaaaa aaaaaaaa
```

Figure 9 Con't

HIV PRE-IMMUNIZATION AND IMMUNOTHERAPY

CROSS REFERENCE TO RELATED APPLICATION

The present application claims priority to U.S. Provisional Application No. 62/190,139, filed on Jul. 8, 2015, the disclosure of which is specifically incorporated by reference.

FIELD OF THE INVENTION

The present invention relates generally to the field of immunization and immunotherapy for the treatment and prevention of HIV. In particular, the disclosed methods of treatment and prevention relate to the administration of viral vectors and system for the delivery of genes and other therapeutic or diagnostic compositions.

BACKGROUND OF THE INVENTION

Combination antiretroviral therapy (cART) (also known as Highly Active Antiretroviral Therapy or HAART) limits HIV-1 replication and retards disease progression, but drug toxicities and the emergence of drug-resistant viruses are challenges for long-term control in HIV-infected persons. Additionally, traditional antiretroviral therapy, while successful at delaying the onset of AIDS or death, has yet to provide a functional cure. Alternative treatment strategies are clearly needed.

Intense interest in immunotherapy for HIV infection has been precipitated by emerging data indicating that the immune system has a major, albeit usually insufficient, role in limiting HIV replication. Virus-specific T-helper cells, which are critical to maintenance of cytolytic T cell (CTL) function, likely have a role. Viremia is also influenced by neutralizing antibodies, but they are generally low in magnitude in HIV infection and do not keep up with evolving viral variants in vivo.

Together these data indicate that increasing the strength and breadth of HIV-specific cellular immune responses might have a clinical benefit through so-called HIV immunotherapy. Some studies have tested vaccines against HIV, but success has been limited to date. Additionally, there has been interest in augmenting HIV immunotherapy by utilizing gene therapy techniques, but as with other immunotherapy approaches, success has been limited. One such method of implementing an HIV-specific immunotherapy or gene therapy could be via specially designed viral vectors.

Viral vectors can be used to transduce genes into target cells owing to specific virus envelope-host cell receptor interactions and viral mechanisms for gene expression. As a result, viral vectors have been used as vehicles for the transfer of genes into many different cell types including whole T cells or other immune cells as well as embryos, fertilized eggs, isolated tissue samples, tissue targets in situ and cultured cells. The ability to introduce and express foreign or altered genes in a cell is useful for therapeutic interventions such as gene therapy, somatic cell reprogramming of induced pluripotent stem cells, and various types of immunotherapy.

Gene therapy is one of the ripest areas of biomedical research with the potential to create new therapeutics that may involve the use of viral vectors. In view of the wide variety of potential genes available for therapy, an efficient means of delivering these genes is needed to fulfill the promise of gene therapy as a means of treating infectious and non-infectious diseases. Several viral systems including murine retrovirus, adenovirus, parvovirus (adeno-associated virus), vaccinia virus, and herpes virus have been developed as therapeutic gene transfer vectors.

There are many factors that must be considered when developing viral vectors, including tissue tropism, stability of virus preparations, stability and control of expression, genome packaging capacity, and construct-dependent vector stability. In addition, in vivo application of viral vectors is often limited by host immune responses against viral structural proteins and/or transduced gene products.

Thus, toxicity and safety are key hurdles that must be overcome for viral vectors to be used in vivo for the treatment of subjects. There are numerous historical examples of gene therapy applications in humans that have met with problems associated with the host immune responses against the gene delivery vehicles or the therapeutic gene products. Viral vectors (e.g., adenovirus) which co-transduce several viral genes together with one or more therapeutic gene(s) are particularly problematic.

Although lentiviral vectors do not generally induce cytotoxicity and do not elicit strong host immune responses, some lentiviral vectors such as HIV-1, which carry several immunostimulatory gene products, have the potential to cause cytotoxicity and induce strong immune responses in vivo. However, this may not be a concern for lentiviral derived transducing vectors that do not encode multiple viral genes after transduction. Of course, this may not always be the case, as sometimes the purpose of the vector is to encode a protein that will provoke a clinically useful immune response.

Another important issue related to the use of lentiviral vectors is that of possible cytopathogenicity upon exposure to some cytotoxic viral proteins. Exposure to certain HIV-1 proteins may induce cell death or functional unresponsiveness in T cells. Likewise, the possibility of generating replication-competent, virulent virus by recombination is often a concern.

Clearly, there is a need for improved treatment of HIV, and the present invention satisfies this need.

SUMMARY OF THE INVENTION

Disclosed herein are therapeutic immunization strategies and methods as well as highly effective therapeutic lentiviruses and other vectors capable of inhibiting HIV and reducing or altering expression of specific targets. The methods and compositions of the disclosed invention are useful for achieving a functional cure of HIV. More specifically, the invention includes methods for a functional cure of HIV that optimally combine therapeutic immunization of a patient, ex vivo re-stimulation of the patient's CD4 T cells, ex vivo lentivirus transduction of the enriched T cells, ex vivo culture of the cells, and reinfusion of the enriched, genetically modified cells. Additionally, the invention includes bioassays to measure treatment efficacy, sequential changes in therapeutic drug administration, monitoring intervals following withdrawal of HAART, and methods of diagnosis of a functional HIV cure.

In one aspect, the disclosed invention relates to a method of treating an HIV infection, comprising: (a) identifying a subject in need of treatment of HIV infection; (b) immunizing the subject with a therapeutically effective amount of an HIV vaccine; (c) removing lymphocytes from the subject and purifying peripheral blood mononuclear cells (PBMC); (d) contacting the PBMC ex vivo with a therapeutically effective amount of an HIV vaccine (which can be the same as or different from the HIV vaccine used in step (b)); (e) transducing the PBMC ex vivo with a viral delivery system encoding at least one genetic element; (f) culturing the transduced PBMC for about 1 to about 21 or up to about 35 days (or any time frame in between these parameters, such as about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, or about 35 days); and (g) infusing the transduced PBMC into the subject.

In some embodiments, step (b) and step (d) utilize the same HIV vaccine, while in other embodiments, step (b) and step (d) utilize different HIV vaccines. In some embodiments, a patient may not require step (b) and/or step (d). Accordingly, in some embodiments, the disclosed methods may only comprise steps (a), (c), (d), (e), (f), and (g), or some combination thereof.

In some embodiments, the subject received cART or HAART prior to infusing the transduced PBMC into the subject. In some embodiments, the subject receives a cyclophosphamide pre-treatment prior to infusing the transduced PBMC into the subject.

In some embodiments, at least one genetic element is selected from the group consisting of a small RNA capable of inhibiting the production of chemokine receptor CCR5, small RNA capable of inhibiting the production of chemokine receptor CXCR4, and small RNA molecules targeting HIV RNA sequences. In some embodiments, the small RNA molecules targeting HIV RNA sequences are directed to gag, pol, env, tat, rev, nef, vif, vpr, vpu, tev, LTR, TAR, RRE, PE, SLIP, CRS, or INS.

In some embodiments, the transduced PBMC are cultured for about 1 to about 7 or up to about 10 days (or for any time frame in between these parameters, such as about 2, about 3, about 4, about 5, about 6, about 7, about 8, about 9, or about 10 days) prior to infusing the transduced PBMC into the subject.

In another aspect, the disclosed invention relates to a viral vector for transducing HIV-specific CD4 T cells, wherein the viral vector encodes at least one genetic element selected from the group consisting of small RNA capable of inhibiting the production of chemokine receptor CCR5, small RNA capable of inhibiting the production of chemokine receptor CXCR4, and small RNA molecules targeting HIV RNA sequences.

In some embodiments, the vector is a lentivirus, but in other embodiments the vector is a DNA plasmid, adeno-associated virus, or other integrating or non-integrating vector systems for gene delivery.

In some embodiments, the small RNA molecules targeting HIV RNA sequences are directed to gag, pol, env, tat, rev, nef, vif, vpr, vpu, tev, LTR, TAR, RRE, PE, SLIP, CRS, or INS.

In another aspect, the disclosed invention relates to a bioassay for determining whether a HIV+ subject is functionally cured. Such a bioassay comprises determining the number of HIV-specific CD4 T cells bearing genetic modification from therapeutic lentivirus, wherein the subject is functionally cured if the number of HIV-specific CD4 T cells bearing genetic modification from therapeutic lentivirus is above a threshold value after a specified time following treatment according to disclosed methods.

In some embodiments, the threshold value is about $1 \times 10^8$ HIV-specific CD4 T cells bearing genetic modification from therapeutic lentivirus, but the threshold value may be determined to be higher or lower than this value.

In some embodiments, the specified time following treatment is about 30 to about 60 days (or any time frame in between these two values), while in other embodiments the specified time following treatment is about 12 to about 26 weeks (or any time frame in between these two values).

In yet another aspect, the disclosed invention relates to a method of achieving a functional cure for HIV in a HIV+ subject. The method comprises: (a) identifying a subject that is HIV+; (b) immunizing the subject with a therapeutically effective amount of an HIV vaccine; (c) removing lymphocytes from the subject and purifying peripheral blood mononuclear cells (PBMC); (d) contacting the PBMC ex vivo with a therapeutically effective amount of an HIV vaccine; (e) transducing the PBMC ex vivo with a viral delivery system encoding at least one genetic element; (f) culturing the transduced PBMC for about 1 to about 21 or up to 35 days (or any timeframe in between these values); and (g) infusing the transduced PBMC into the subject, wherein the HIV+ subject achieves a functional cure.

In some embodiments step (b) and step (d) comprise the same HIV vaccine, while in other embodiments, step (b) and step (d) comprise different HIV vaccines.

In some embodiments, the subject received cART or HAART prior to infusing the transduced PBMC into the subject. In some embodiments, the subject receives a cyclophosphamide pre-treatment or alternative conditioning therapies to improve T cell engraftment prior to infusing the transduced PBMC into the subject.

In some embodiments, at least one genetic element is selected from the group consisting of a small RNA capable of inhibiting the production of chemokine receptor CCR5, small RNA capable of inhibiting the production of chemokine receptor CXCR4, and small RNA molecules targeting HIV RNA sequences. In some embodiments, the small RNA molecules targeting HIV RNA sequences are directed to gag, pol, env, tat, rev, nef, vif, vpr, vpu, tev, LTR, TAR, RRE, PE, SLIP, CRS, or INS.

In some embodiments, the transduced PBMC are cultured for about 1 to about 7 or up to about 12 days (or any timeframe in between these two values, or other time periods described herein) prior to infusing the transduced PBMC into the subject.

The foregoing general description and following brief description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

FIG. 4 shows exemplary vector sequences. Positive (genomic) strand sequence of the promoter and miR cluster were developed for inhibiting the spread of CCR5-tropic HIV strains. Sequences that are not underlined comprise the EF-1alpha promoter of transcription that was selected as best for this miR cluster. Sequences that are underlined show the miR cluster consisting of miR30 CCR5 (a modification of the natural human miR30 that redirects to CCR5 mRNA), miR21 Vif (redirects to Vif RNA sequence) and miR185 Tat (redirects to Tat RNA sequence). The sequences that are not underlined and in smaller font are restriction endonuclease cleavage sites that were incorporated into the oligonucleotide primers for each of the miRNA constructs.

FIG. 9 shows the sequences of various exemplary cellular elements known to restrict HIV replication that may be incorporated into the disclosed vectors.

DETAILED DESCRIPTION OF THE PREFERRED EMBODIMENTS

Figure 1:
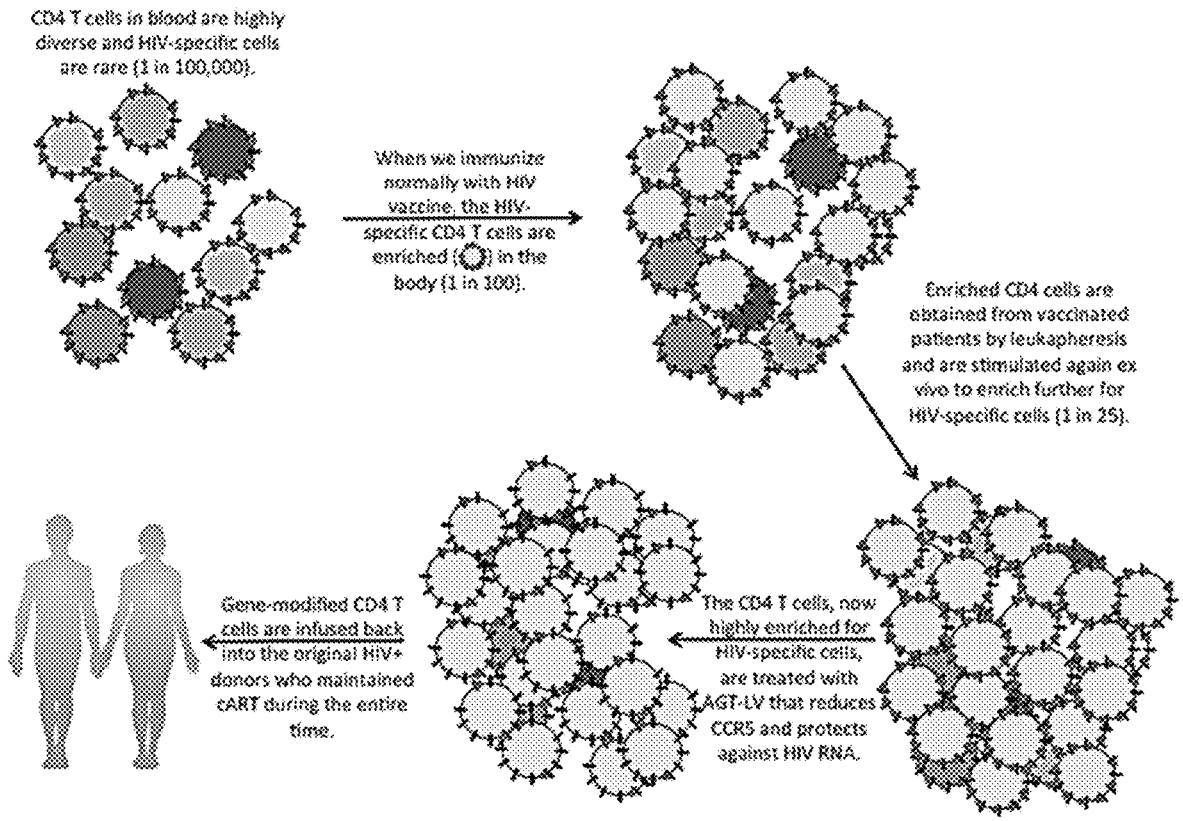
FIG. 1 shows a flow chart diagram of possible clinical therapy incorporating vaccination, cell collection to obtain PBMC and CD4 T cells, ex vivo T cell culture after stimulating with vaccine immunogens and/or CD3/CD28 stimulation and/or mitogen stimulation in the presence of supporting growth cytokines (including, but not limited to, interleukin-2, interleukin-12, interleukin-15, interleukin-6, interleukin-7, and interleukin-23), lentivirus transduction to deliver anti-HIV genetic constructs, brief culture of transduced cells, and infusion back into the original subject.
Figure 2:
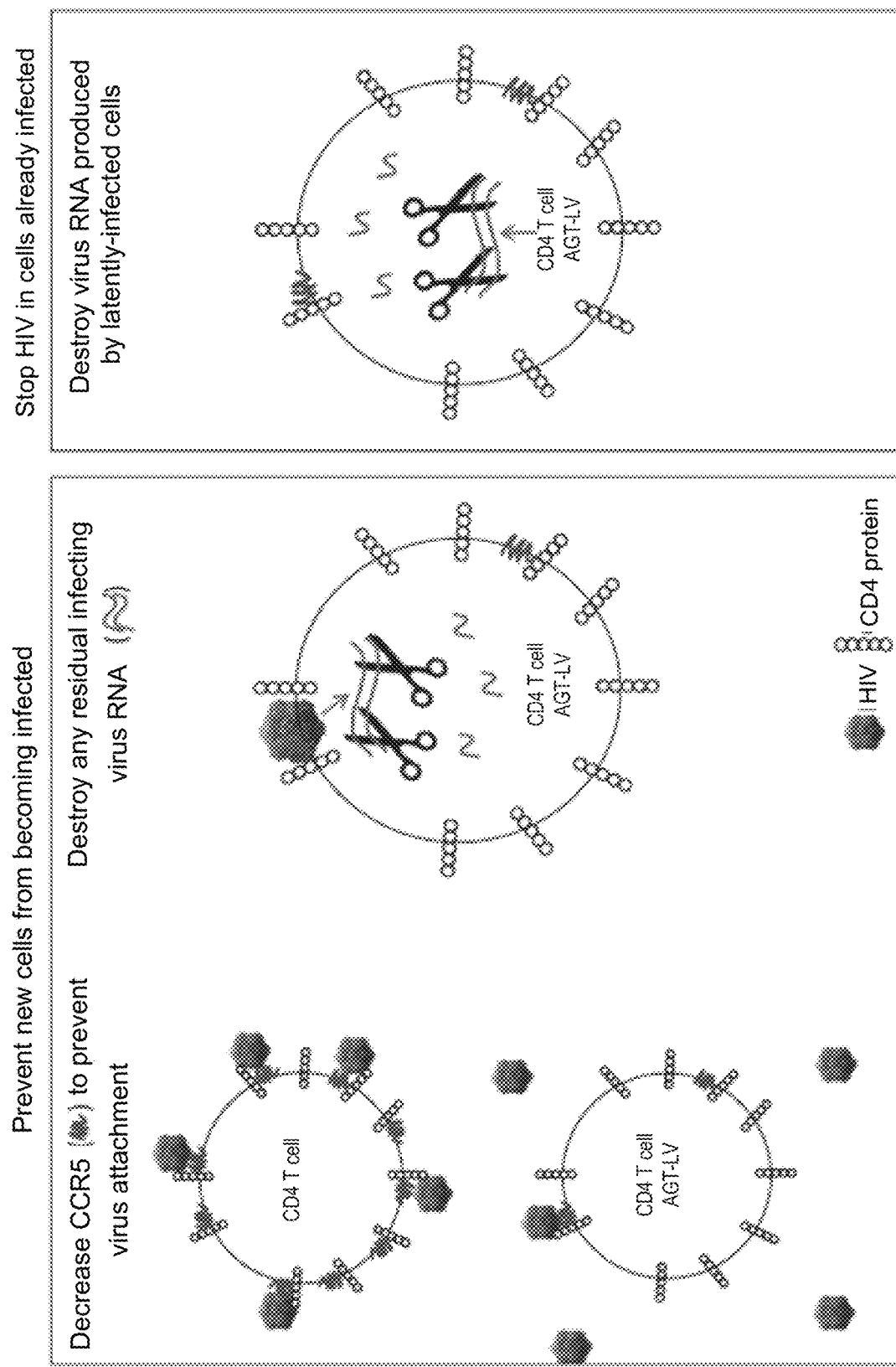
FIG. 2 shows how CD4 T cells may be altered using gene therapy to prevent other cells from becoming infected or to prevent viral replication.

Disclosed herein are methods and compositions for treating and/or preventing human immunodeficiency virus (HIV) disease to achieve a functional cure. A functional cure is defined as a condition resulting from the disclosed treatments and methods that reduces or eliminates the need for cART and may or may not require supporting adjuvant therapy. The methods of the invention include gene delivery by integrating lentivirus, non-integrating lentivirus, and related viral vector technology as described below.

Disclosed herein are therapeutic viral vectors (e.g., lentivirus vectors), immunotherapies, and methods for their use in a strategy to achieve a functional cure for HIV infection. The general strategy can include first therapeutic immunization with vaccines intended to produce strong immune responses against HIV in HIV-infected patients with stable suppression of viremia due to daily administration of HAART, for the purpose of enriching the fraction of HIV-specific CD4 T cells. This is followed by (1) isolating peripheral leukocytes by leukapheresis or purifying PBMC from venous blood, (2) re-stimulating CD4 T cells ex vivo with HIV vaccine proteins, (3) performing therapeutic lentivirus transduction, ex vivo T cell culture, and (4) reinfusion back into the original donor.

Previous efforts to achieve a cure for HIV have fallen short principally due to the failure to obtain sufficient numbers of HIV-specific CD4 T cells with protective genetic modifications. When this value is below a critical threshold, removing antiretroviral therapy allows HIV re-emergence, followed by rapid destruction of HIV-specific CD4 T cells, and also followed by return to progression of disease despite prior genetic therapy. By employing therapeutic immunization in the strategy described herein and providing highly effective therapeutic lentiviruses capable of inhibiting HIV, a new strategy for achieving a functional cure of HIV has been developed.

Also disclosed herein are novel viral vectors for enhancing HIV-specific CD4 T cells including lentiviral vectors and non-integrating, episomally replicating viral vectors and methods of using the same. Episomally replicating vectors like the present invention can comprise viral components from viruses like Papovaviridae (e.g. bovine papillomavirus or BPV) or Herpesviridae (e.g. Epstein Barr Virus or EBV) or Hepadnaviridae (e.g. Hepatitis B Virus or HBV). Episomal replicating vectors derived from these viruses may comprise a replication origin and at least one viral trans-acting factor, e.g., an initiator protein, such as E1 for BPV and EBNA-1 for EBV or HBV polymerase or terminus binding protein of Adenovirus. The process of episomal replication typically incorporates both host cell replication machinery and viral trans-acting factors.

I. Human Immunodeficiency Virus (HIV)

HIV is a retrovirus that causes acquired immunodeficiency syndrome (AIDS) in humans. AIDS is a condition in which progressive failure of the immune system allows life-threatening opportunistic infections and cancers to thrive. Without treatment, average survival time after infection with HIV is estimated to be 9 to 11 years, depending upon the HIV subtype. Infection with HIV occurs by the transfer of bodily fluids, including but not limited to blood, semen, vaginal fluid, pre-ejaculate, saliva, tears, lymph or cerebro-spinal fluid, or breast milk. HIV may be present in an infected individual as both free virus particles and within infected immune cells.

HIV infects vital cells in the human immune system such as helper T cells, although tropism can vary among HIV subtypes. Immune cells that may be specifically susceptible to HIV infection include but are not limited to CD4+ T cells, macrophages, and dendritic cells. HIV infection leads to low levels of CD4+ T cells through a number of mechanisms, including but not limited to apoptosis of uninfected bystander cells, direct viral killing of infected cells, and killing of infected CD4+ T cells by CD8 cytotoxic lymphocytes that recognize infected cells. When CD4+ T cell numbers decline below a critical level, cell-mediated immunity is lost, and the body becomes progressively more susceptible to opportunistic infections and cancer.

Structurally, HIV is distinct from many other retroviruses. The RNA genome consists of at least seven structural landmarks (LTR, TAR, RRE, PE, SLIP, CRS, and INS), and at least nine genes (gag, pol, env, tat, rev, nef, vif, vpr, vpu, and sometimes a tenth tev, which is a fusion of tat, env and rev), encoding 19 proteins. Three of these genes, gag, pol, and env, contain information needed to make the structural proteins for new virus particles.

HIV replicates primarily in CD4 T cells, and causes cellular destruction or dysregulation to reduce host immunity. Because HIV establishes infection as an integrated provirus and may enter a state of latency wherein virus expression in a particular cell decreases below the level for cytopathology affecting that cell or detection by the host immune system, HIV is difficult to treat and has not been eradicated even after prolonged intervals of highly active antiretroviral therapy (HAART). In the vast majority of cases, HIV infection causes fatal disease although survival may be prolonged by HAART.

A major goal in the fight against HIV is to develop strategies for curing disease. Prolonged HAART has not accomplished this goal, so investigators have turned to alternative procedures. Early efforts to improve host immunity by therapeutic immunization (using a vaccine after infection has occurred) had marginal or no impact. Likewise, treatment intensification had moderate or no impact.

Some progress has been made using genetic therapy, but positive results are sporadic and found only among rare human beings carrying defects in one or both alleles of the gene encoding CCR5 (chemokine receptor), which plays a critical role in viral penetration of host cells. However, many investigators are optimistic that genetic therapy holds the best promise for eventually achieving an HIV cure.

As disclosed herein, the methods and compositions of the invention are able to achieve a functional cure that may or may not include complete eradication of all HIV from the body. A functional cure is defined as a state or condition wherein HIV+ individuals who previously required HAART, may survive with low or undetectable virus replication and using lower or intermittent doses of HAART, or are potentially able to discontinue HAART altogether. As used herein, a functional cure may still possibly require adjunct therapy to maintain low level virus replication and slow or eliminate disease progression. A possible outcome of a functional cure is the eventual eradication of HIV to prevent all possibility of recurrence.

The primary obstacles to achieving a functional cure lie in the basic biology of HIV itself. Virus infection deletes CD4 T cells that are critical for all immune functions. Most importantly, HIV infection and depletion of CD4 T cells requires activation of individual cells. Activation is a specific mechanism for individual CD4 T cell clones that recognize pathogens or other molecules, using a rearranged T cell receptor.

In the case of HIV, infection activates a population of HIV-specific T cells that become infected and are consequently depleted before other T cells that are less specific for the virus, effectively crippling the immune system's defense against the virus. The capacity for HIV-specific T cell responses is rebuilt during prolonged HAART; however, when HAART is interrupted the rebounding virus infection repeats the process and again deletes the virus-specific cells, resetting the clock on disease progression.

Clearly, a functional cure is only possible if enough HIV-specific CD4 T cells are protected to allow for a host's native immunity to confront and control HIV once HAART is interrupted. In one embodiment, the present invention provides methods and compositions for improving the effectiveness of genetic therapy to provide a functional cure of HIV disease. In another embodiment, the present invention provides methods and compositions for enhancing host immunity against HIV to provide a functional cure. In yet another embodiment, the present invention provides methods and compositions for enriching HIV-specific CD4 T cells in a patient to achieve a functional cure.

In one embodiment of the invention, treatment results in enriching a subject's HIV-specific CD4 T cells by about 100%, about 200%, about 300%, about 400%, about 500%, about 600%, about 700%, about 800%, about 900%, about 1000%, about 1500%, about 2000%, about 2500%, about 3000%, about 3500%, about 4000%, about 4500%, about 5000%, about 5500%, about 6000%, about 6500%, about 7000%, about 7500%, about 8000%, about 8500%, about 9000%, about 9500%, about 10000%, about 11000%, about 12000%, about 13000%, about 14000%, about 15000%, about 16000%, about 17000%, about 18000%, about 19000%, about 20000%, about 25000%, about 30000%, about 35000%, about 40000%, about 45000%, about 50000%, about 55000%, about 60000%, about 65000%, about 70000%, about 75000%, about 80000%, about 85000%, about 90000%, about 95000%, about 100000%, or any value in between.

II. Gene Therapy

Viral vectors are used to deliver genetic constructs to host cells for the purposes of disease therapy or prevention.

Genetic constructs can include, but are not limited to, functional genes or portions of genes to correct or complement existing defects, DNA sequences encoding regulatory proteins, DNA sequences encoding regulatory RNA molecules including antisense, short homology RNA, long non-coding RNA, small interfering RNA or others, and decoy sequences encoding either RNA or proteins designed to compete for critical cellular factors to alter a disease state. Gene therapy involves delivering these therapeutic genetic constructs to target cells to provide treatment or alleviation of a particular disease.

There are multiple ongoing efforts to utilize genetic therapy in the treatment of HIV disease, but thus far, the results have been poor. A small number of treatment successes were obtained in rare HIV patients carrying a spontaneous deletion of the CCR5 gene (an allele known as CCR5delta32).

Lentivirus-delivered nucleases or other mechanisms for gene deletion/modification may be used to lower the overall expression of CCR5 and/or help to lower HIV replication. At least one study has reported having success in treating the disease when lentivirus was administered in patients with a genetic background of CCR5delta32. However, this was only one example of success, and many other patients without the CCR5delta32 genotype have not been treated as successfully. Consequently, there is a substantial need to improve the performance of viral genetic therapy against HIV, both in terms of performance for the individual viral vector construct and for improved use of the vector through a strategy for achieving functional HIV cure.

For example, some existing therapies rely on zinc finger nucleases to delete a portion of CCR5 in an attempt to render cells resistant to HIV infection. However, even after optimal treatment, only 30% of T cells had been modified by the nuclease at all, and of those that were modified, only 10% of the total CD4 T cell population had been modified in a way that would prevent HIV infection. In contrast, the disclosed methods result in virtually every cell carrying a lentivirus transgene having a reduction in CCR5 expression below the level needed to allow HIV infection.

For the purposes of the disclosed methods, gene therapy can include, but is not limited to, affinity-enhanced T cell receptors, chimeric antigen receptors on CD4 T cells (or alternatively on CD8 T cells), modification of signal transduction pathways to avoid cell death cause by viral proteins, increased expression of HIV restriction elements including TREX, SAMHD1, MxA or MxB proteins, APOBEC complexes, TRIM5-alpha complexes, tetherin (BST2), and similar proteins identified as being capable of reducing HIV replication in mammalian cells.

For example, in some embodiments the disclosed vectors may include, but are not limited to, the restriction elements found in Table 1 below. The sequences of these exemplary restriction elements are further disclosed in FIG. 9.

TABLE 1

| Gene | Accession Number |
| --- | --- |
| TREX1 | NM_016381 (human) |
|  | XM_015128506.1 (*Macaca mulatta*) |
| TREX2 | NM_080701/NM_007205 (human |
|  | XM_015128506.1 (*Macaca mulatta*) |
| SAMHD1 | NM_015474 (human) |
|  | JN936895.1 (*Macaca mulatta*) |
| MxA | NM_001144925 (human) |
|  | JX297237.1 (*Macaca mulatta*) |
| MxB | NM_002463 (human) |
| APOBEC3G | NM_021822 (human) |
|  | XM_015150306 (*Macaca mulatta*) |
| TRIM5-alpha | NM_033034 (human) |
|  | NM_001032910.1 (*Macaca mulatta*) |
| Tetherin | NM_004335 (human) |
|  | FJ943432.1 (*Macaca mulatta*) |

III. Immunotherapy

Historically, vaccines have been a go-to weapon against deadly infectious diseases, including smallpox, polio, measles, and yellow fever. Unfortunately, there is no currently approved vaccine for HIV. The HIV virus has unique ways of evading the immune system, and the human body seems incapable of mounting an effective immune response against it. As a result, scientists do not have a clear picture of what is needed to provide protection against HIV.

However, immunotherapy may provide a solution that was previously unaddressed by conventional vaccine approaches. Immunotherapy, also called biologic therapy, is a type of treatment designed to boost the body's natural defenses to fight infections or cancer. It uses materials either made by the body or in a laboratory to improve, target, or restore immune system function.

In some embodiments of the disclosed invention, immunotherapeutic approaches may be used to enrich a population of HIV-specific CD4 T cells for the purpose of increasing the host's anti-HIV immunity. In some embodiments of the disclosed invention, integrating or non-integrating lentivirus vectors may be used to transduce a host's immune cells for the purposes of increasing the host's anti-HIV immunity. In yet another embodiment of the invention, a vaccine comprising HIV proteins including but not limited to a killed particle, a virus-like particle, HIV peptides or peptide fragments, a recombinant viral vector, a recombinant bacterial vector, a purified subunit or plasmid DNA combined with a suitable vehicle and/or biological or chemical adjuvants to increase a host's immune responses may be used to enrich the population of virus-specific T cells or antibodies, and these methods may be further enhanced through the use of HIV-targeted genetic therapy using lentivirus or other viral vector.

IV. Methods According to the Invention

In one aspect, the disclosed invention provides methods for using viral vectors to achieve a functional cure for HIV disease. The methods further include immunotherapy to enrich the proportion of HIV-specific CD4 T cells, followed by lentivirus transduction to deliver inhibitors of HIV and CCR5 and CXCR4 as required.

In one embodiment, the methods include therapeutic immunization as a method for enriching the proportion of HIV-specific CD4 T cells. Therapeutic immunization can include purified proteins, inactivated viruses, virally vectored proteins, bacterially vectored proteins, peptides or peptide fragments, virus-like particles (VLPs), biological or chemical adjuvants including cytokines and/or chemokines, vehicles, and methods for immunization.

Therapeutic vaccines can include one or more HIV protein with protein sequences representing the predominant viral types of the geographic region where treatment is occurring. Therapeutic vaccines will include purified proteins, inactivated viruses, virally vectored proteins, bacterially vectored proteins, peptides or peptide fragments, virus-like particles (VLPs), biological or chemical adjuvants including cytokines and/or chemokines, vehicles, and methods for immunization. Vaccinations may be administered according to standard methods known in the art and HIV patients may continue antiretroviral therapy during the interval of immunization and subsequent ex vivo lymphocyte culture including lentivirus transduction.

In some embodiments, HIV+ patients can be immunized with an HIV vaccine, increasing the frequency of HIV-specific CD4 T cells by about 2, about 25, about 250, about 500, about 750, about 1000, about 1250, or about 1500-fold (or any amount in between these values). The vaccine may be any clinically utilized or experimental HIV vaccine, including the disclosed lentiviral, other viral vectors or other bacterial vectors used as vaccine delivery systems. For instance, the disclosed vector may comprise a recombinant Bacille Calmette Guerin (BCG) strain expressing HIV VLP. BCG is Mycobacterium Bovis attenuated for use as a human vaccine against tuberculosis. In another embodiment, the vectors can encode virus-like particles (VLPs) to induce higher titers of neutralizing antibodies. In another embodiment, the vectors can encode peptides or peptide fragments associated with HIV including but not limited to gag, pol, and env, tat, rev, nef, vif, vpr, vpu, and tev, as well as LTR, TAR, RRE, PE, SLIP, CRS, and INS. Alternatively, the HIV vaccine used in the disclosed methods may comprise purified proteins, inactivated viruses, virally vectored proteins, bacterially vectored proteins, peptides or peptide fragments, virus-like particles (VLPs), or biological or chemical adjuvants including cytokines and/or chemokines.

In one embodiment, the methods include ex vivo re-stimulation of CD4 T cells from persons or patients previously immunized by therapeutic vaccination, using purified proteins, inactivated viruses, virally vectored proteins, bacterially vectored proteins, biological or chemical adjuvants including cytokines and/or chemokines, vehicles, and methods for re-stimulation. Ex vivo re-stimulation may be performed using the same vaccine or immune stimulating compound used for in vivo immunization, or it may be performed using a different vaccine or immune stimulating compound than those used for in vivo immunization. Moreover, in some embodiments, the patient may not require prior therapeutic vaccination or re-stimulation of CD4 T cells if the individual has sufficiently high antigen-specific CD4 T cell responses to HIV proteins. In these embodiments, such a patient may only require administration of the disclosed viral vectors to achieve a functional cure.

For example, peripheral blood mononuclear cells (PBMCs) can be obtained by leukapheresis and treated ex vivo to obtain about $1\times10^{10}$ CD4 T cells of which about 0.1%, about 1%, about 5% or about 10% or about 30% are both HIV-specific in terms of antigen responses, and HIV-resistant by virtue of carrying the therapeutic transgene delivered by the disclosed lentivirus vector. Alternatively, about $1\times10^7$, about $1\times10^8$, about $1\times10^9$, about $1\times10^{10}$, about $1\times10^{11}$, or about $1\times10^{12}$ CD4 T cells may be isolated for re-stimulation. Any suitable amount of CD4 T cells can be isolated for ex vivo re-stimulation.

The isolated CD4 T cells can be cultured in appropriate medium throughout re-stimulation with HIV vaccine antigens, which may include antigens present in the prior therapeutic vaccination. Antiretroviral therapeutic drugs including inhibitors of reverse transcriptase, protease or integrase may be added to prevent virus re-emergence during prolonged ex vivo culture. CD4 T cell re-stimulation is used to enrich the proportion of HIV-specific CD4 T cells in culture. The same procedure may also be used for analytical objectives wherein smaller blood volumes with peripheral blood mononuclear cells obtained by purification, are used to identify HIV-specific T cells and measure the frequency of this sub-population.

The PBMC fraction may be enriched for HIV-specific CD4 T cells by contacting the cells with HIV proteins matching or complementary to the components of the vaccine previously used for in vivo immunization. Ex vivo re-stimulation can increase the relative frequency of HIV-specific CD4 T cells by about 25, about 50, about 75, about 100, about 125, about 150, about 175, or about 200-fold.

The methods additionally include combining in vivo therapeutic immunization and ex vivo re-stimulation of CD4 T cells with ex vivo lentiviral transduction and culturing.

Thus, in one embodiment, the re-stimulated PBMC fraction that has been enriched for HIV-specific CD4 T cells can be transduced with therapeutic anti-HIV lentivirus or other vectors and maintained in culture about 1 to about 21 days or up to about 35 days. Alternatively, the cells may be cultured for about 1-about 18 days, about 1-about 15 days, about 1-about 12 days, about 1-about 9 days, or about 3-about 7 days. Thus, the transduced cells may be cultured for about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, or about 35 days.

Once the transduced cells have been sufficiently cultured, transduced CD4 T cells are infused back into the original patient. Infusion can be performed using various machines and methods known in the art. In some embodiments, infusion may be accompanied by pre-treatment with cyclophosphamide or similar compounds to increase the efficiency of re-engraftment.

In some embodiments, a CCR5-targeted therapy may be added to a subject's antiretroviral therapy regimen, which was continued throughout the treatment process. Examples of CCR5-targeted therapies include but are not limited to Maraviroc (a CCR5 antagonist) or Rapamycin (immunosuppressive agent that lowers CCR5). In some embodiments, the antiretroviral therapy may be ceased and the subject can be tested for virus rebound. If no rebound occurs, adjuvant therapy can also be removed and the subject can be tested again for virus rebound.

Continued virus suppression with reduced or no antiretroviral therapy include cART or HAART, and reduced or no adjuvant therapy for about 26 weeks can be considered a functional cure for HIV. Other definitions of a functional cure are described herein.

The lentiviral and other vectors used in the disclosed methods may encode at least one, at least two, at least three, at least four, or at least five genes of interest. Given the versatility and therapeutic potential of HIV-targeted gene therapy, a viral vector of the invention may encode genes or nucleic acid sequences that include but are not limited to (i) an antibody directed to an antigen associated with an infectious disease or a toxin produced by the infectious pathogen, (ii) cytokines including interleukins that are required for immune cell growth or function and may be therapeutic for immune dysregulation encountered in HIV and other chronic or acute human viral or bacterial pathogens, (iii) factors that suppress the growth of HIV in vivo including CD8 suppressor factors, (iv) mutations or deletions of chemokine receptor CCR5, mutations or deletions of chemokine receptor CXCR4, or mutations or deletions of chemokine receptor CXCR5, (v) antisense DNA or RNA against specific receptors or peptides associated with HIV or host protein associated with HIV, (vi) small interfering RNA against specific receptors or peptides associated with HIV or host protein associated with HIV, or (vii) a variety of other therapeutically useful sequences that may be used to treat HIV or AIDS.

Additional examples of HIV-targeted gene therapy that can be used in the disclosed methods include, but are not limited to, affinity-enhanced T cell receptors, chimeric antigen receptors on CD4 T cells (or alternatively on CD8 T cells), modification of signal transduction pathways to avoid cell death cause by viral proteins, increased expression of HIV restriction elements including TREX, SAMHD1, MxA or MxB proteins, APOBEC complexes, TRIM5-alpha complexes, tetherin (BST2), and similar proteins identified as being capable of reducing HIV replication in mammalian cells.

In some embodiment, a patient may be undergoing cART or HAART concurrently while being treated according to the methods of the invention. In other embodiments, a patient may undergo cART or HAART before or after being treated according to the methods of the invention. In some embodiments, cART or HAART is maintained throughout treatment according to the methods of the invention and the patient may be monitored for HIV viral burden in blood and frequency of lentivirus-transduced CD4 T cells in blood. Preferably, a patient receiving cART or HAART prior to being treated according to the methods of the invention is able to discontinue or reduce cART or HAART following treatment according to the methods of the invention.

For efficacy purposes, the frequency of transduced, HIV-specific CD4 T cells, which is a novel surrogate marker for gene therapy effects, may be determined, as discussed in more detail in Section VI.

V. Compositions According to the Invention

In one aspect, the disclosed invention provides lentiviral vectors capable of delivering genetic constructs to inhibit HIV penetration of susceptible cells. For instance, one mechanism of action is to reduce mRNA levels for CCR5 and/or CXCR4 chemokine receptors and thus reduce the rates for viral entry into susceptible cells.

Alternatively, the disclosed lentiviral vectors may be capable of inhibiting the formation of DNA and HIV-infected cells by reducing the stability of incoming HIV genomic RNA. And in yet another embodiment, the disclosed lentivirus vectors are capable of preventing HIV production from a latently infected cell, wherein the mechanism of action is to cause instability of viral RNA sequences through the action of inhibitory RNA including short-homology, small-interfering or other regulatory RNA species.

The therapeutic lentiviruses disclosed in this application generally comprise at least one of two types of genetic cargo. First, the lentiviruses may encode genetic elements that direct expression of small RNA capable of inhibiting the production of chemokine receptors CCR5 and/or CXCR4 that are important for HIV penetration of susceptible cells. The second type of genetic cargo includes constructs capable of expressing small RNA molecules targeting HIV RNA sequences for the purpose of preventing reverse transcription, RNA splicing, RNA translation to produce proteins, or packaging of viral genomic RNA for particle production and spreading infection. An exemplary structure is diagrammed in FIG. 3.

Figure 3:
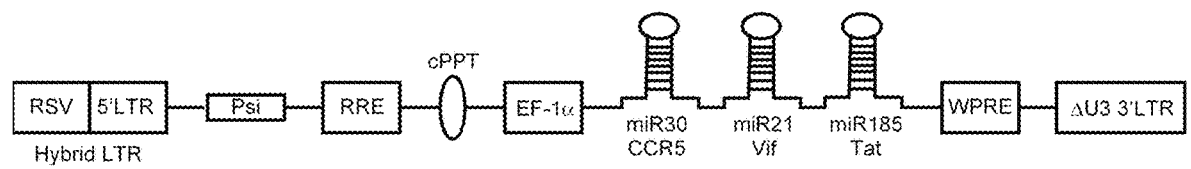
FIG. 3 shows a schematic of an exemplary therapeutic lentiviral construct. Therapeutic lentivirus constructs may substitute alternate sequences for the promoter region, targeting of regulatory RNA, and types of regulatory RNA. Further, the plasmids used for packaging the lentivirus particles can be altered according to production needs.

As shown in FIG. 3, an exemplary construct may comprise numerous sections or components. For example, in one embodiment, an exemplary LV construct may comprise the following sections or components:
  RSV—a Rous Sarcoma virus long terminal repeat;
  5'LTR—a portion of an HIV long terminal repeat that can be truncated to prevent replication of the vector after chromosomal integration;
  Psi—a packaging signal that allows for incorporation of the vector RNA genome into viral particles during packaging;
  RRE—a Rev Responsive element can be added to improve expression from the transgene by mobilizing RNA out of the nucleus and into the cytoplasm of cells;
  c PPT—a Poly purine tract that facilitates second strand DNA synthesis prior to integration of the transgene into the host cell chromosome;
  Promoter—a promoter initiates RNA transcription from the integrated transgene to express micro-RNA clusters (or other genetic elements of the construct), and in some embodiments, the vectors may use an EF-1 promoter;
  Anti-CCR5—a micro RNA targeting messenger RNA for the host cell factor CCR5 to reduce its expression on the cell surface;
  Anti-Rev/Tat—a micro RNA targeting HIV genomic or messenger RNA at the junction between HIV Rev and Tat coding regions, which is sometimes designated miRNA Tat or a\given a similar description in this application;
  Anti-Vif—a micro RNA targeting HIV genomic or messenger RNA within the Vif coding region;
  WPRE—a woodchuck hepatitis virus post-transcriptional regulatory element is an additional vector component that can be used to facilitate RNA transport of the nucleus; and
  deltaU3 3'LTR—a modified version of a HIV 3-prime long terminal repeat where a portion of the U3 region has been deleted to improve safety of the vector.

One of skill in the art will recognize that the above components are merely examples, and that such components may be reorganized, substituted with other elements, or otherwise changed, so long as the construct is able to prevent expression of HIV genes and decrease the spread of infection.

Vectors of the invention may include either or both of the types of genetic cargo discussed above (i.e. genetic elements that direct expression of a gene or small RNAs, such as siRNA, shRNA, or miRNA that can prevent translation or transcription), and the vectors of the invention may also encode additionally useful products for the purpose of treatment or diagnosis of HIV. For instance, in some embodiments, these vectors may also encode green fluorescent protein (GFP) for the purpose of tracking the vectors or antibiotic resistance genes for the purposes of selectively maintaining genetically-modified cells in vivo.

The combination of genetic elements incorporated into the disclosed vectors is not particularly limited. For example, a vector may encode a single small RNA, two small RNAs, three small RNA, four small RNAs, five small RNAs, six small RNAs, seven small RNAs, eight small RNAs, nine small RNAs, or ten small RNAs. Such vectors may additionally encode other genetic elements to function in concert with the small RNAs to prevent expression and infection of HIV.

Those of skill in the art will understand that the therapeutic lentivirus may substitute alternate sequences for the promoter region, targeting of regulatory RNA, and types of regulatory RNA. Further, the therapeutic lentivirus of the invention may comprise changes in the plasmids used for packaging the lentivirus particles; these changes are required to increase levels of production in vitro.

In some embodiments, the vector used in the disclosed methods may be a DNA plasmid, adeno-associated virus, or other integrating or non-integrating vector systems for gene delivery.

VI. Bioassays

In one aspect, the present invention includes bioassays for determining the success of HIV treatment for achieving a functional cure. These assays will provide a method for measuring the efficacy of the disclosed methods of immunization and treatment by measuring the frequency of transduced, HIV specific CD4 T cells in a patient. HIV-specific CD4 T cells are recognizable because they proliferate, change the composition of cell surface markers, induce signaling pathways including phosphorylation, or express specific marker proteins that may be cytokines, chemokines, caspases, phosphorylated signaling molecules or other cytoplasmic and/or nuclear components. Specific responding CD4 T cells are recognized for example, using labeled monoclonal antibodies or specific in situ amplification of mRNA sequences, that allow sorting of HIV-specific cells using flow cytometry sorting, magnetic bead separation or other recognized methods for antigen-specific CD4 T cell isolation. The isolated CD4 T cells are tested to determine the frequency of cells carrying integrated therapeutic lentivirus. Single cell testing methods may also be used including microfluidic separation of individual cells, that are coupled with mass spectrometry, PCR, ELISA or antibody staining to confirm responsiveness to HIV and presence of integrated therapeutic lentivirus.

Thus, in one embodiment, following application of a treatment according to the invention (e.g., (a) immunization, (b) ex vivo lymphocyte culture; (c) re-stimulation with purified proteins, inactivated viruses, virally vectored proteins, bacterially vectored proteins, biological or chemical adjuvants including cytokines and/or chemokines, vehicles; and (d) infusion of the enriched, transduced T cells), a patient may be subsequently assayed to determine the efficacy of the treatment. A threshold value of target T cells in the body may be established to measure a functional cure at, for instance, about $1 \times 10^8$ HIV-specific CD4 T cells bearing genetic modification from therapeutic lentivirus. The value threshold value of cells refers to the total body content. It may not be measured directly, but instead may be extrapolated from blood CD4 T cell counts using a standard correction. For example, it is common in the art to assume that 90% of CD4 T cells are present in tissues and only 10% are found in blood.

Alternatively, the threshold value may be about $1 \times 10^5$, about $1 \times 10^6$, about $1 \times 10^7$, about $1 \times 10^9$, or about $1 \times 10^{10}$ CD4 T cells in the body of the patient.

HIV-specific CD4 T cells bearing genetic modification from therapeutic lentivirus can be determined using any suitable method, such as but not limited to flow cytometry, cell sorting, FACS analysis, DNA cloning, PCR, RT-PCR or Q-PCR, ELISA, FISH, western blotting, southern blotting, high throughput sequencing, RNA sequencing, oligonucleotide primer extension, or other methods known in the art.

Methods for defining antigen specific T cells with genetic modifications are known in the art. However, utilizing such methods to combine identifying HIV-specific T cells with integrated or non-integrated gene therapy constructs as a standard measure for efficacy is a new concept in the field of HIV treatment.

VII. Doses and Dosage Forms

The disclosed methods and compositions can be used for treating HIV+ patients during various stages of their disease. Accordingly, dosing regimens may vary based upon the condition of the patient and the method of administration.

In one embodiment, HIV-specific vaccines for the initial in vivo immunization may be administered to a subject in need in varying doses. In general, vaccines delivered by intramuscular injection include about 10 µg to about 300 µg, about 25 µg to about 275 µg, about 50 µg to about 250 µg, about 75 µg to about 225, or about 100 µg to about 200 µg of HIV protein, either total virus protein prepared from inactivated virus particles, virus-like particles or purified virus protein from recombinant systems or purified from virus preparations. Recombinant viral or bacterial vectors may be administered by any and all of the routes described. Intramuscular vaccines will include about 1 µg to about 100 µg, about 10 µg to about 90 µg, about 20 µg to about 80 µg, about 30 µg to about 70 µg, about 40 µg to about 60 µg, or about 50 µg of suitable adjuvant molecules and be suspended in oil, saline, buffer or water in volumes of 0.1 to 5 ml per injection dose, and may be soluble or emulsion preparations. Vaccines delivered orally, rectally, bucally, at genital mucosal or intranasally, including some virally-vectored or bacterially-vectored vaccines, fusion proteins, liposome formulations or similar preparations, may contain higher amounts of virus protein and adjuvant. Dermal, sub-dermal or subcutaneous vaccines utilize protein and adjuvant amounts more similar to oral, rectal or intranasal-delivered vaccines. Depending on responses to the initial immunization, vaccination may be repeated 1-5 times using the same or alternate routes for delivery. Intervals may be of 2-24 weeks between immunizations. Immune responses to vaccination are measured by testing HIV-specific antibodies in serum, plasma, vaginal secretions, rectal secretions, saliva or bronchoalveolar lavage fluids, using ELISA or similar methodology. Cellular immune responses are tested by in vitro stimulation with vaccine antigens followed by staining for intracellular cytokine accumulation followed by flow cytometry or similar methods including lymphoproliferation, expression of phosphorylated signaling proteins or changes in cell surface activation markers. Upper limits of dosing may be determined based on the individual patient and will depend on toxicity/safety profiles for each individual product or product lot.

Immunization may occur once, twice, three times, or repeatedly. For instance, an agent for HIV immunization may be administered to a subject in need once a week, once every other week, once every three weeks, once a month, every other month, every three months, every six months, every nine months, once a year, every eighteen months, every two years, every 36 months, or every three years.

Immunization will occur at least once before ex vivo expansion and enrichment of CD4 T cells, and immunization may occur once, twice, three times, or more after ex vivo lymphocyte culture/re-stimulation and infusion.

In one embodiment, HIV-vaccines for immunization are administered as a pharmaceutical composition. In one embodiment, the pharmaceutical composition comprising an HIV vaccine can be formulated in a wide variety of nasal, pulmonary, oral, topical, or parenteral dosage forms for clinical application. Each of the dosage forms can comprise various disintegrating agents, surfactants, fillers, thickeners, binders, diluents such as wetting agents or other pharmaceutically acceptable excipients. The pharmaceutical composition comprising an HIV vaccine can also be formulated for injection.

HIV vaccine compositions for the purpose of immunization can be administered using any pharmaceutically acceptable method, such as intranasal, buccal, sublingual, oral, rectal, ocular, parenteral (intravenously, intradermally, intramuscularly, subcutaneously, intracisternally, intraperitoneally), pulmonary, intravaginal, locally administered, topically administered, topically administered after scarification, mucosally administered, via an aerosol, or via a buccal or nasal spray formulation.

Further, the HIV vaccine compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, and a suspension. Further, the composition may be a controlled release formulation, sustained release formulation, immediate release formulation, or any combination thereof. Further, the composition may be a transdermal delivery system.

In another embodiment, the pharmaceutical composition comprising an HIV vaccine can be formulated in a solid dosage form for oral administration, and the solid dosage form can be powders, granules, capsules, tablets or pills. In yet another embodiment, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release or a modified release form. Modified release dosage forms include controlled or extended release, enteric release, and the like. The excipients used in the modified release dosage forms are commonly known to a person of ordinary skill in the art.

In a further embodiment, the pharmaceutical composition comprising a HIV vaccine can be formulated as a sublingual or buccal dosage form. Such dosage forms comprise sublingual tablets or solution compositions that are administered under the tongue and buccal tablets that are placed between the cheek and gum.

In yet a further embodiment, the pharmaceutical composition comprising an HIV vaccine can be formulated as a nasal dosage form. Such dosage forms of the present invention comprise solution, suspension, and gel compositions for nasal delivery.

In one embodiment, the pharmaceutical composition can be formulated in a liquid dosage form for oral administration, such as suspensions, emulsions or syrups. In other embodiments, the liquid dosage form can include, in addition to commonly used simple diluents such as water and liquid paraffin, various excipients such as humectants, sweeteners, aromatics or preservatives. In particular embodiments, the composition comprising HIV vaccine or a pharmaceutically acceptable salt thereof can be formulated to be suitable for administration to a pediatric patient.

In one embodiment, the pharmaceutical composition can be formulated in a dosage form for parenteral administration, such as sterile aqueous solutions, suspensions, emulsions, non-aqueous solutions or suppositories. In other embodiments, the non-aqueous solutions or suspensions can include propyleneglycol, polyethyleneglycol, vegetable oils such as olive oil or injectable esters such as ethyl oleate. As a base for suppositories, witepsol, macrogol, tween 61, cacao oil, laurin oil or glycerinated gelatin can be used.

The dosage of the pharmaceutical composition can vary depending on the patient's weight, age, gender, administration time and mode, excretion rate, and the severity of disease.

For the purposes of re-stimulation, lymphocytes, PBMCs, and/or CD4 T cells are removed from a patient and isolated for re-stimulation and culturing. The isolated cells may be contacted with the same HIV vaccine or activating agent used for immunization or a different HIV vaccine or activating agent. In one embodiment, the isolated cells are contacted with about 10 ng to 5 μg of an HIV vaccine or activating agent per about $10^6$ cells in culture (or any other suitable amount). More specifically, the isolated cells may be contacted with about 50 ng, about 100 ng, about 200 ng, about 300 ng, about 400 ng, about 500 ng, about 600 ng, about 700 ng, about 800 ng, about 900 ng, about 1 μg, about 1.5 μg, about 2 μg, about 2.5 μg, about 3 μg, about 3.5 μg, about 4 μg, about 4.5 μg, or about 5 μg of an HIV vaccine or activating agent per about $10^6$ cells in culture.

Activating agents or vaccines are generally used once for each in vitro cell culture but may be repeated after intervals of about 15 to about 35 days. For example, a repeat dosing could occur at about 15, about 16, about 17, about 18, about 19, about 20, about 21, about 22, about 23, about 24, about 25, about 26, about 27, about 28, about 29, about 30, about 31, about 32, about 33, about 34, or about 35 days.

For transduction of the enriched, re-stimulated cells, the cells may be transduced with lentiviral vectors or with other known vector systems as disclosed in Section V and FIG. 3. The cells being transduced may be contacted with about 1-1,000 viral genomes (measured by RT-PCR assay of culture fluids containing lentivirus vector) per target cell in culture (or any other suitable amount). Lentivirus transduction may be repeated 1-5 times using the same range of 1-1,000 viral genomes per target cell in culture.

VIII. Definitions

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

"A treatment" is intended to target the disease state and combat it, i.e., ameliorate or prevent the disease state. The particular treatment thus will depend on the disease state to be targeted and the current or future state of medicinal therapies and therapeutic approaches. A treatment may have associated toxicities.

The terms "administration of" or "administering" an active agent should be understood to mean providing an active agent of the invention to the subject in need of treatment in a form that can be introduced into that individual's body in a therapeutically useful form and therapeutically effective amount.

The term "therapeutically effective amount" refers to a sufficient quantity of the active agents of the present invention, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

The term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

The term "functional cure" refers to a state or condition wherein HIV+ individuals who previously required cART or HAART, may survive with low or undetectable virus replication using lower doses, intermittent doses, or discontinued dosing of cART or HAART. An individual may be said to have been "functionally cured" while still requiring adjunct therapy to maintain low level virus replication and slow or eliminate disease progression. A possible outcome of a functional cure is the eventual eradication of HIV to prevent all possibility of recurrence.

The term "HIV vaccine" encompasses immunogens plus vehicle plus adjuvant intended to elicit HIV-specific immune responses. Vaccine may include purified or whole inactivated virus particles that may be HIV or a recombinant virus vectors capable of expressing HIV proteins, protein fragments or peptides, glycoprotein fragments or glycopeptides, in addition to recombinant bacterial vectors, plasmid DNA or RNA capable of directing cells to producing HIV proteins, glycoproteins or protein fragments able to elicit specific immunity. Alternately, specific methods for immune stimulation including anti-CD3/CD28 beads, T cell receptor-specific antibodies, mitogens, superantigens and other chemical or biological stimuli may be used to activate dendritic, T or B cells for the purposes of enriching HIV-specific CD4 T cells prior to transduction or for in vitro assay of lentivirus-transduced CD4 T cells. Activating substances may be soluble, polymeric assemblies, liposome or endosome-based or linked to beads. Cytokines including interleukin-2, 6, 7, 12, 15, 23 or others may be added to improve cellular responses to stimuli and/or improve the survival of CD4 T cells throughout the culture and transduction intervals.

The terms "individual," "host," "subject," and "patient" are used interchangeably herein.

As used herein, "expression," "expressed," or "encodes" refers to the process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

As used herein, "small RNA" refers to non-coding RNA that are generally less than about 200 nucleotides or less in length and possess a silencing or interference function. In other embodiments, the small RNA is about 175 nucleotides or less, about 150 nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). "Small RNA" of the disclosure should be capable of inhibiting or knocking-down gene expression of a target gene, generally through pathways that result in the destruction of the target gene mRNA.

The following examples are given to illustrate the present invention. It should be understood, however, that the invention is not to be limited to the specific conditions or details described in these examples. All printed publications referenced herein are specifically incorporated by reference.

EXAMPLES

Example 1—Clinical Study for Treatment of HIV

Screening and Informed Consent.

Select HIV+ participants receiving combination antiretroviral therapy (cART) with stable suppression of virus burden are chosen to participate.

Immunization with a Therapeutic HIV Vaccine.

A vaccine that already has IND status and has been used in a clinical trial involving HIV+ participants is administered to participants. This step will increase the relative frequency of HIV-specific CD4 T cells by approximately 1,000-fold.

Next, blood lymphocytes are removed by leukapheresis and further purified to the peripheral blood mononuclear cell (PBMC) fraction. Alternately, cells may be purified from venous blood by column or density gradient methods.

Cultured PBMC are stimulated with HIV proteins or peptides matching or complementing the components in the therapeutic vaccine (perhaps using the same vaccine depending on its composition). This step will increase the relative frequency of HIV-specific CD4 T cells by approximately 100-fold.

Cultured PBMC cells are infected with therapeutic lentivirus or other disclosed vectors, for instance, one that encodes small RNA to interfere with the translation of CCR5 and viral replication proteins. After transduction, the cells are maintained in culture 3-7 days.

Transduced CD4 T cells are infused back into the original participant. Infusion can be performed according to methods known in the art. This may require pre-treatment with cyclophosphamide to increase the efficiency of re-engraftment.

For participants receiving cART, cART will be maintained throughout. Following infusion, monitor HIV viral burden in blood and frequency of lentivirus-transduced CD4 T cells in blood.

If participants meet qualifying criteria (including having $>10^6$, $>10^7$, $>10^8$ Lentivirus-transduced, HIV-specific CD4 T cells in the total of blood and tissue compartments), they may move to an efficacy study. If participants miss the qualifying criterion they may be eligible to receive a second dose of therapeutic lentivirus using the same protocol.

Further Study and Bioassay.

For qualified participants at 30-60 days after transduced T cell infusion, begin testing the efficacy of gene therapy. First, add a CCR5-targeted treatment to their existing cART regimen. This may be the CCR5-blocking drug Maraviroc or the immune suppressing drug Rapamycin that lowers CCR5 receptor density on T cells. The therapeutic lentivirus also targets CCR5 and the combined effects of lentivirus plus Maraviroc or Rapamycin should decrease CCR5 below levels needed to sustain HIV replication.

Two weeks after adding Maraviroc or Rapamycin, the cART therapy is stopped and participants are monitored closely for HIV virus rebound. If they rebound, cART is reintroduced and managed by their regular physician.

If HIV virus does not rebound, step-down of the Maraviroc or Rapamycin is started in 2 week intervals until treatment is stopped.

If viremia does not return within 12-26 weeks, the participant has achieved a functional cure of HIV.

A database of values relating the number of HIV-specific, lentivirus-transduced CD4 T cells to treatment efficacy (including the frequency of cells with latent HIV infection or other markers) will establish a Gold Standard by which other gene therapy protocols could be judged.

Example 2—Developing an Anti-HIV Lentivirus Vector

The purpose of this example was to develop an anti-HIV lentivirus vector.

Inhibitory RNA Designs:

The sequence of Homo sapiens chemokine C-C motif receptor 5 (CCR5) (GC03P046377) mRNA was used to search for potential siRNA or shRNA candidates to knock-down CCR5 levels in human cells. Potential RNA interference sequences were chosen from candidates selected by siRNA or shRNA design programs such as from the Broad Institute or the BLOCK-iT RNAi Designer from Thermo Scientific. Individual selected shRNA sequences were inserted into lentiviral vectors immediately 3' to a RNA polymerase III promoter such as H1, U6, or 7SK to regulate shRNA expression. These lentivirus-shRNA constructs were used to transduce cells and measure the change in specific mRNA levels. The shRNA most potent for reducing mRNA levels were embedded individually within a microRNA backbone to allow for expression by either the CMV or EF-1alpha RNA polymerase II promoters. The microRNA backbone was selected from mirbase.org/. RNA sequences were also synthesized as synthetic siRNA oligonucleotides and introduced directly into cells without using a lentiviral vector.

The genomic sequence of Bal strain of human immunodeficiency virus type 1 (HIV-1 85US_BaL, accession number AY713409) was used to search for potential siRNA or shRNA candidates to knockdown HIV replication levels in human cells. Based on sequence homology and experience, the search focused on regions of the Tat and Vif genes of HIV although an individual of skill in the art will understand that use of these regions is non-limiting and other potential targets might be selected. Highly conserved regions of Gag or Polymerase genes could not be targeted by shRNA because these same sequences were present in the packaging system complementation plasmids needed for vector manufacturing. As with the CCR5 (NM 000579.3, NM 001100168.1-specific RNAs, potential HIV-specific RNA interference sequences were chosen from candidates selected by siRNA or shRNA design programs such as from the Gene-E Software Suite hosted by the Broad Institute (broadinstitute.org/mai/public) or the BLOCK-iT RNAi Designer from Thermo Scientific (rnadesigner.thermofisher.com/rnaiexpress/setOption.do?designOption=shrna&pid=671262736070606180 1). Individual selected shRNA sequences were inserted into lentiviral vectors immediately 3' to a RNA polymerase III promoter such as H1, U6, or 7SK to regulate shRNA expression. These lentivirus-shRNA constructs were used to transduce cells and measure the change in specific mRNA levels. The shRNA most potent for reducing mRNA levels were embedded individually within a microRNA backbone to allow for expression by either the CMV or EF-1alpha RNA polymerase II promoters Vector Constructions:

For CCR5, Tat or Vif shRNA, oligonucleotide sequences containing BamHI and EcoRI restriction sites were synthesized by Eurofins MWG Operon, LLC. Overlapping sense and antisense oligonucleotide sequences were mixed and annealed during cooling from 70 degrees Celsius to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Invitrogen. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered, purified and expanded in LB broth. To check for insertion of the oligo sequences, plasmid DNA were extracted from harvested bacteria cultures with the Invitrogen DNA mini prep kit. Insertion of the shRNA sequence in the lentiviral vector was verified by DNA sequencing using a specific primer for the promoter used to regulate shRNA expression. Exemplary vector sequences and cellular elements known to restrict HIV replication can be found in FIGS. 4 and 9, respectively.

For example, the shRNA sequences with the highest activity against CCR5, Tat or Vif gene expression were then assembled into a microRNA (miR) cluster under control of the EF-1alpha promoter. The promoter and miR sequences are depicted in FIG. 4.

Functional Assays:

Individual lentivirus vectors containing CCR5, Tat or Vif shRNA sequences and, for experimental purposes, expressing green fluorescent protein (GFP) under control of the CMV Immediate Early Promoter, and designated AGT103/CMV-GFP were tested for their ability to knockdown CCR5, Tat or Vif expression. Mammalian cells were transduced with lentiviral particles either in the presence or absence of polybrene. Cells were collected after 2-4 days; protein and RNA were analyzed for CCR5, Tat or Vif expression. Protein levels were tested by Western blot assay or by labeling cells with specific fluorescent antibodies (CCR5 assay), followed by analytical flow cytometry comparing modified and unmodified cell fluorescence using either the CCR5-specific or isotype control antibodies.

Starting Testing of Lentivirus:

T cell culture medium was made using RPMI 1640 supplemented with 10% FBS and 1% penicillin-streptomycin. Cytokine stocks of IL2 10000 units/ml, IL12 1 µg/ml, IL7 1 µg/ml, IL15 1 µg/ml were also prepared in advance.

Prior to transduction with the lentivirus, an infectious viral titer was determined and used to calculate the amount of virus to add for the proper multiplicity of infection (MOI).

Day 0-12: Antigen-Specific Enrichment:

On day 0, cryopreserved PBMC were thawed, washed with 10 ml 37° C. medium at 1200 rpm for 10 minutes and resuspended at a concentration of $2 \times 10^6$/ml in 37° C. medium. The cells were cultured at 0.5 ml/well in a 24-well plate at 37° C. in 5% $CO_2$. To define the optimal stimulation conditions, cells were stimulated with combinations of reagents as listed in Table 2 below:

TABLE 2

| 1 | 2 | 3 | 4 | 5 | 6 |
|---|---|---|---|---|---|
| IL2 + IL12 | IL7 + IL15 | Peptides + IL2 + IL12 | Peptides + IL7 + IL15 | MVA + IL2 + IL12 | MVA + IL7 + IL15 |

Final concentrations: IL2=20 units/ml, IL12=10 ng/ml, IL7=10 ng/ml, IL15=10 ng/ml, peptides=5 µg/ml individual peptide, MVA MOI=1.

On days 4 and 8, 0.5 ml fresh medium and cytokine at listed concentrations (all concentrations indicate the final concentration in the culture) were added to the stimulated cells.

Day 12-24: Non-Specific Expansion and Lentivirus Transduction:

On day 12, the stimulated cells were removed from the plate by pipetting and resuspended in fresh T cell culture medium at a concentration of $1 \times 10^6$/ml. The resuspended cells were transferred to T25 culture flasks and stimulated with DYNABEADS® Human T-Activator CD3/CD28 following the manufacturer's instruction plus cytokine as listed above; flasks were incubated in the vertical position.

On day 14, AGT103/CMV-GFP was added at MOI 20 and cultures were returned to the incubator for 2 days. At this time, cells were recovered by pipetting, collected by centrifugation at 1300 rpm for 10 minutes, resuspended in the same volume of fresh medium, and centrifuged again to form a loose cell pellet. That cell pellet was resuspended in fresh medium with the same cytokines used in previous steps, with cells at $0.5 \times 10^6$ viable cells per ml.

From days 14 to 23, the number of the cells was evaluated every 2 days and the cells were diluted to $0.5 \times 10^6$/ml with fresh media. Cytokines were added every time.

On day 24, the cells were collected and the beads were removed from the cells. To remove the beads, cells were transferred to a suitable tube that was placed in the sorting magnet for 2 minutes. Supernatant containing the cells was transferred to a new tube. Cells were then cultured for 1 day in fresh medium at $1 \times 10^6$/ml. Assays were performed to determine the frequencies of antigen-specific T cells and lentivirus transduced cells.

To prevent possible viral outgrowth, amprenavir (0.5 ng/ml) was added to the cultures on the first day of stimulation and every other day during the culture.

Examine Antigen-Specific T Cells by Intracellular Cytokine Staining for IFN-Gamma:

Cultured cells after peptide stimulation or after lentivirus transduction at $1 \times 10^6$ cells/ml were stimulated with medium alone (negative control), Gag peptides (5 µg/ml individual peptide), or PHA (5 µg/ml, positive control). After 4 hours, BD GOLGIPLUG™ (1:1000, BD Biosciences) was added to block Golgi transport. After 8 hours, cells were washed and stained with extracellular (CD3, CD4 or CD8; BD Biosciences) and intracellular (IFN-_gamma; BD Biosciences) antibodies with BD CYTOFIX/CYTOPERM™ kit following the manufacturer's instruction. Samples were analyzed on a BD FACSCALIBUR™ Flow Cytometer. Control samples labeled with appropriate isotype-matched antibodies were included in each experiment. Data were analyzed using Flowjo software.

Lentivirus transduction rate was determined by the frequency of GFP+ cells. The transduced antigen-specific T cells are determined by the frequency of CD3+CD4+GFP+ IFN gamma+ cells; tests for CD3+CD8+GFP+IFN gamma+ cells are included as a control.

These results indicate that CD4 T cells, the target T cell population, can be transduced with lentiviruses that are designed to specifically knock down the expression of HIV-specific proteins, thus producing an expandable population of T cells that are immune to the virus. This example serves as a proof of concept indicating that the disclosed lentiviral constructs can be used in combination with vaccination to produce a functional cure in HIV patients.

Example 3—CCR5 Knockdown with Experimental Vectors

AGTc120 is a Hela cell line that stably expresses large amounts of CD4 and CCR5. AGTc120 was transduced with or without LV-CMV-mCherry (the red fluorescent protein mCherry expressed under control of the CMV Immediate Early Promoter) or AGT103/CMV-mCherry. Gene expression of the mCherry fluorescent protein was controlled by a CMV (cytomegalovirus immediate early promoter) expression cassette. The LV-CMV-mCherry vector lacked a microRNA cluster, while AGT103/CMV-mCherry expressed therapeutic miRNA against CCR5, Vif, and Tat.

Figure 5A:
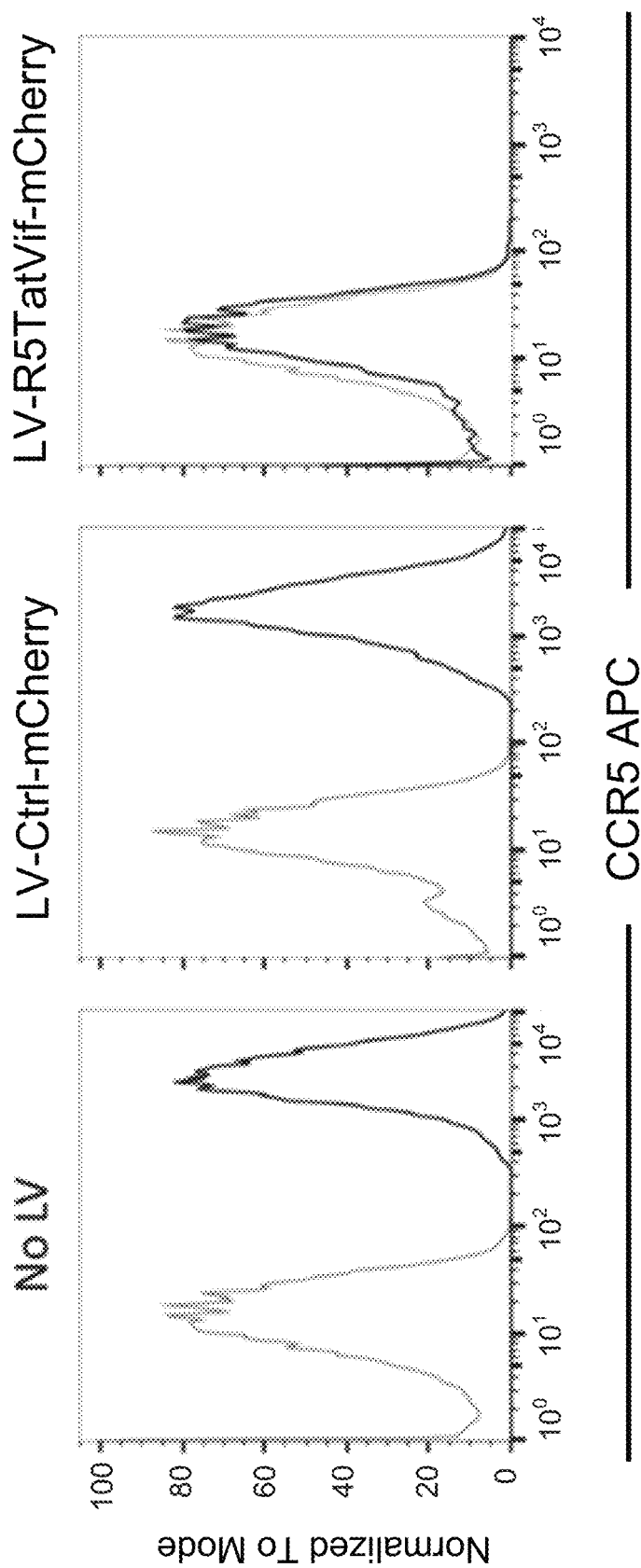
FIG. 5 shows that knockdown of CCR5 by an experimental vector prevents R5-tropic HIV infection in AGTc120 cells. Panel (A) shows CCR5 expression in AGTc120 cells with or without AGT103 lentivirus vector. Panel (B) shows the sensitivity of transduced AGTc120 cells to infection with a HIV BaL virus stock that was expressing green fluorescent protein (GFP) fused to the Nef gene of HIV.

As shown in FIG. 5A, transduction efficiency was >90%. After 7 days, cells were collected and stained with fluorescent monoclonal antibody against CCR5 and subjected to analytical flow cytometry. Isotype controls are shown in gray on these histograms plotting Mean Fluorescence Intensity of CCR5 APC (x axis) versus cell number normalized to mode (y axis). After staining for cell surface CCR5, cells treated with no lentivirus or control lentivirus (expressing only the mCherry marker) showed no changes in CCR5 density while AGT103 (right section) reduced CCR5 staining intensity to nearly the levels of isotype control. After 7 days, cells were infected with or without R5-tropic HIV reporter virus Bal-GFP. 3 days later, cells were collected and analyzed by flow cytometry. More than 90% of cells were transduced. AGT103-CMV/CMVmCherry reduced CCR5 expression in transduced AGTc120 cells and blocked R5-tropic HIV infection compared with cells treated with the Control vector.

Figure 5B:
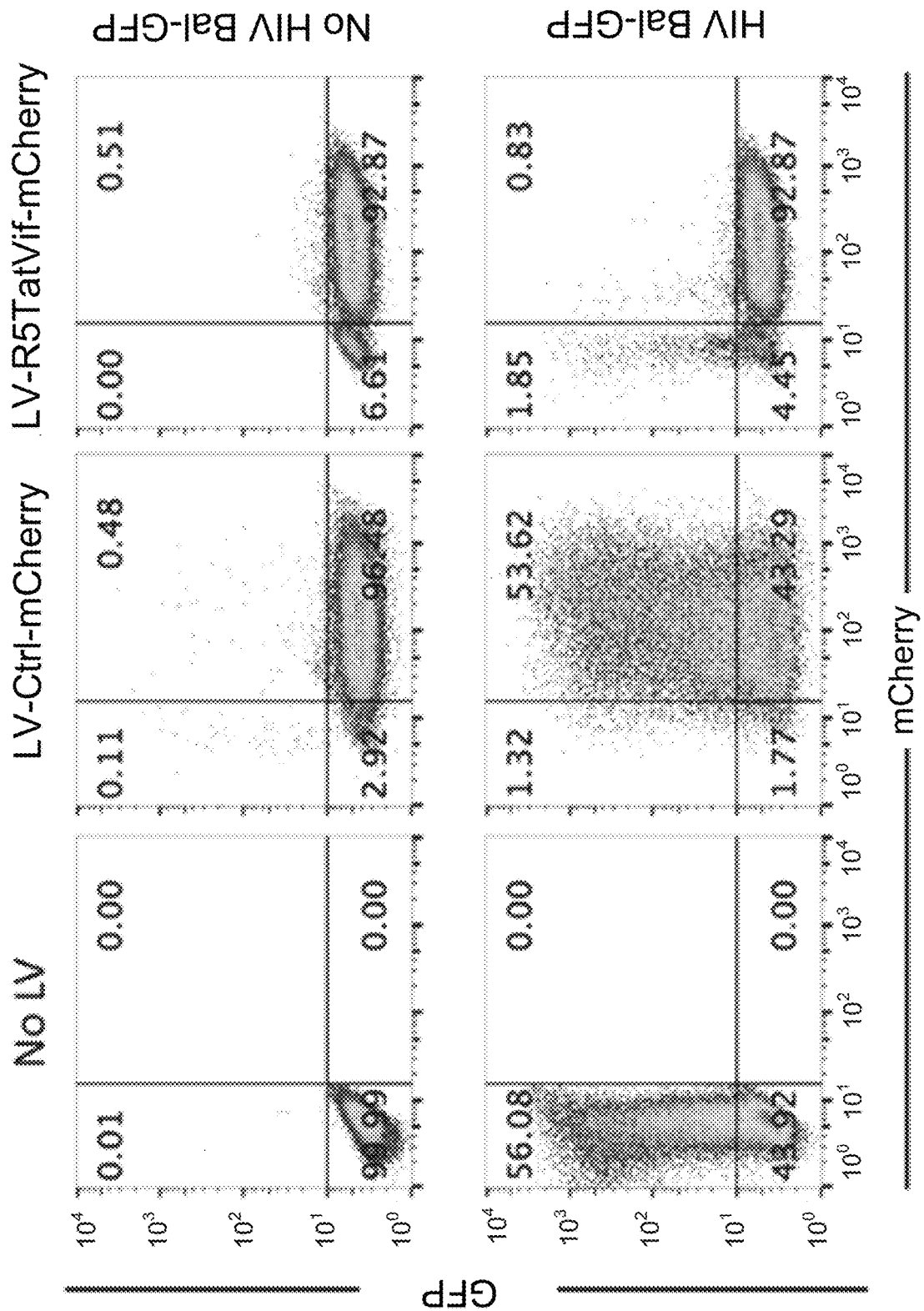

FIG. 5B shows the relative insensitivity of transfected AGTc120 cells to infection with HIV. As above, the lentivirus vectors express mCherry protein and a transduced cell that was also infected with HIV (expressing GFP) would appear as a double positive cell in the upper right quadrant of the false color flow cytometry dot plots. In the absence of HIV (upper panels), there were no GFP+ cells under any condition. After HIV infection (lower panels), 56% of cells were infected in the absence of lentivirus transduction and 53.6% of cells became infected in AGTc120 cells transduced with the LV-CMV-mCherry. When cells were transduced with the therapeutic AGT103/CMV-mCherry vector, only 0.83% of cells appeared in the double positive quadrant indicating they were transduced and infected.

Dividing 53.62 (proportion of double positive cells with control vector) by 0.83 (the proportion of double positive cells with the therapeutic vector) shows that AGT103 provided greater than 65-fold protection against HIV in this experimental system.

Example 4—AGT103 Decreases Expression of Tat and Vif

Cells were transfected with exemplary vector AGT103/CMV-GFP. AGT103 and other exemplary vectors are defined in Table 3 below.

TABLE 3

| Vector Designation | Composition |
|---|---|
| AGT103 | EF1-miR30CCR5-miR21Vif-miR185-Tat-WPRE |
| Control-mCherry | CMV-mCherry |
| AGT103/CMV-mCherry | CMV-mCherry-EF1-miR30CCR5-miR21Vif-miR185-Tat-WPRE- |
| Control-GFP | CMV-mCherry |
| AGT103/CMV-GFP | CMV-GFP-EF1-miR30CCR5-miR21Vif-miR185-Tat-WPRE- |

Figure 6:
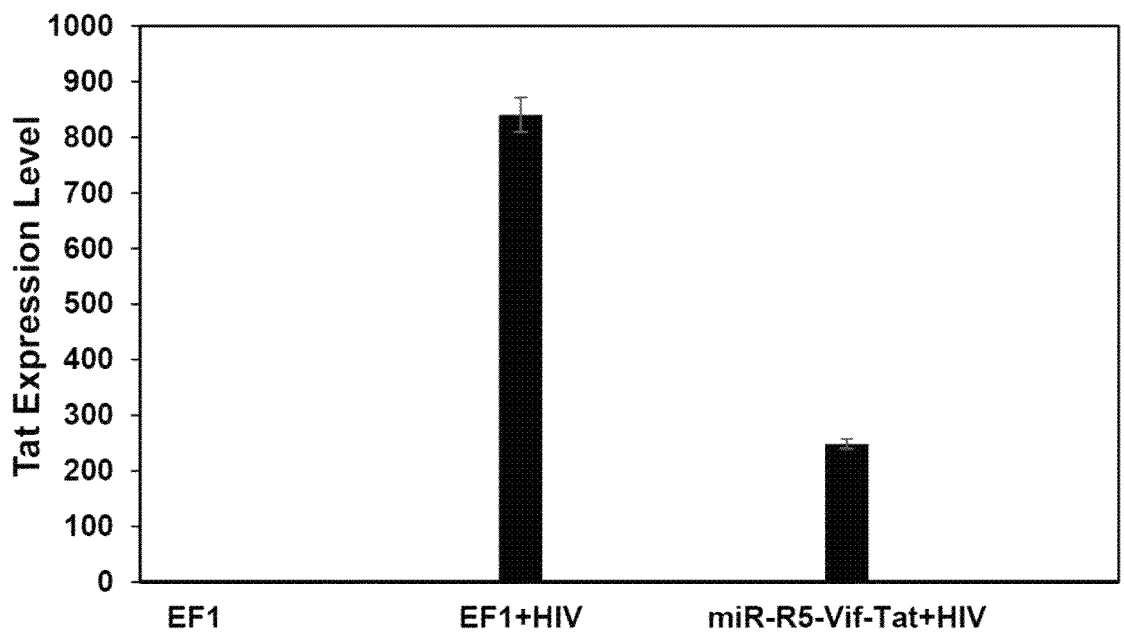
FIG. 6 shows AGT103 reduces expression of Tat protein expression in cells transfected with HIV expression plasmid.

Abbreviations:
EF-1: elongation factor 1 transcriptional promoter
miR30CCR5—synthetic microRNA capable of reducing CCR5 protein on cell surfaces
miR21Vif—synthetic microRNA capable of reducing levels of HIV RNA and Vif protein expression
miR185Tat—synthetic micro RNA capable of reducing levels of HIV RNA and Tat protein expression
CMV—Immediate early transcriptional promoter from human cytomegalovirus
mCherry—coding region for the mCherry red fluorescent protein
GFP—coding region for the green fluorescent protein
WPRE—Woodchuck hepatitis virus post transcriptional regulatory element A T lymphoblastoid cell line (CEM; CCRF-CEM; American Type Culture Collection Catalogue number CCL119) was transduced with AGT103/CMV-GFP. 48 hours later the cells were transfected with an HIV expression plasmid encoding the entire viral sequence. After 24 hours, RNA was extracted from cells and tested for levels of intact Tat sequences using reverse transcriptase polymerase chain reaction. Relative expression levels for intact Tat RNA were reduced from approximately 850 in the presence of control lentivirus vector, to approximately 200 in the presence of AGT103/CMV-GFP for a total reduction of >4 fold, as shown in FIG. 6.

Figure 7:
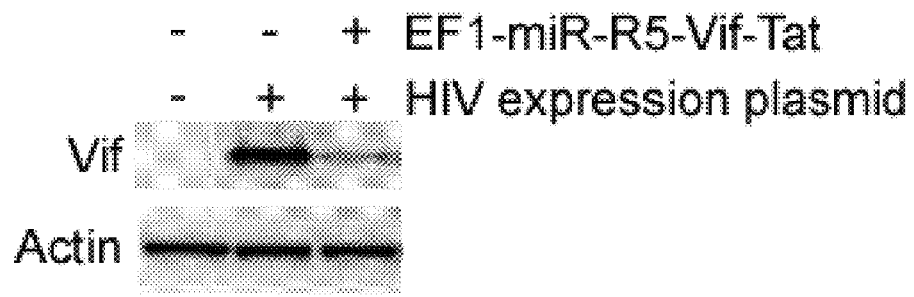
FIG. 7 shows AGT103 reduces levels of Vif protein expression in cells transfected with a full-length HIV expression plasmid. Cells were untreated (left lane and center lane) or transduced with AGT103 (left lane).

In a similar experiment, HEK 293T cells (Human Embryonic Kidney 293T; American Type Culture Collection Catalogue number CRL-3216) cells were transduced with AGT103/CMV-GFP and then an HIV expression plasmid was transfected into cells 7 days after transduction (control was not transfected with HIV). 24 hours after transfection cells were lysed and analyzed by Western blot using antibodies specific for Actin (cellular loading control) or HIV Vif protein. The presence of AGT103/CMV-GFP (right lane) caused a dramatic reduction in Vif protein expression levels as shown in FIG. 7.

Figure 8A:
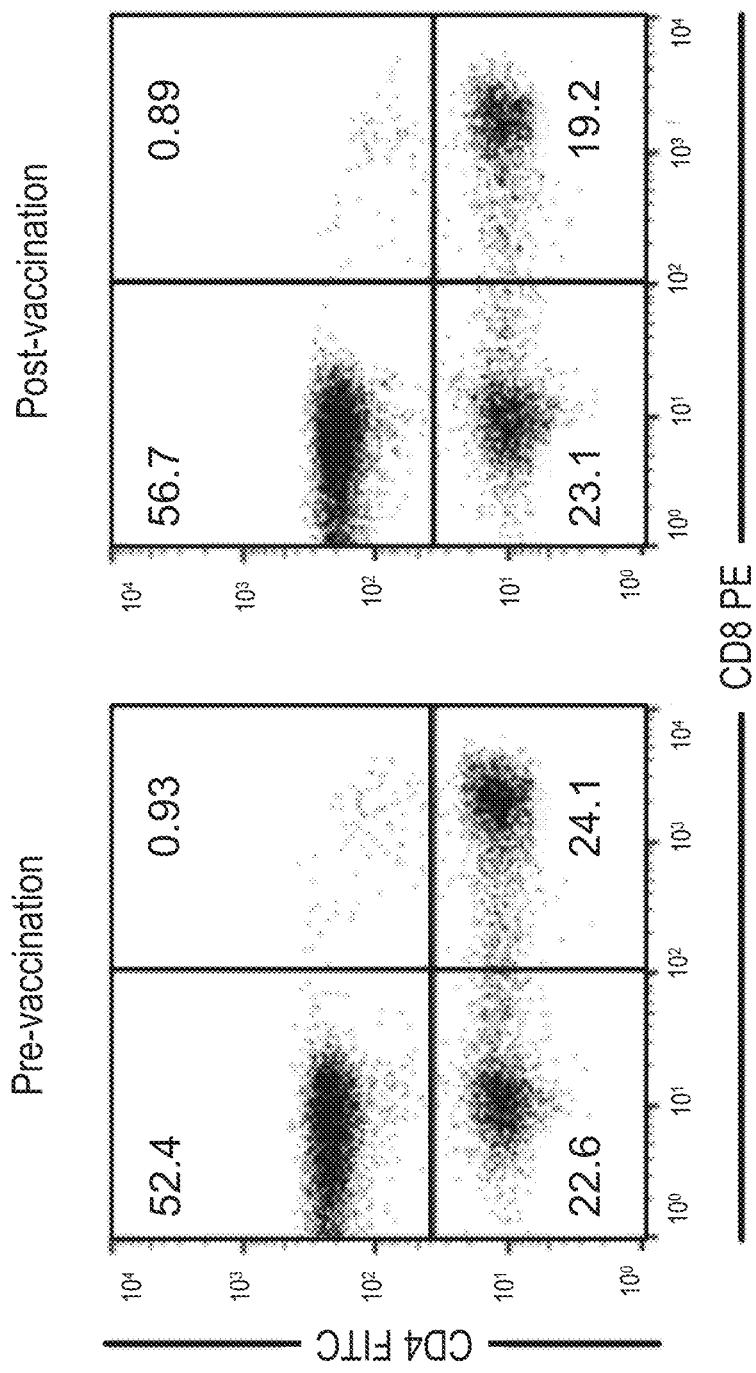
FIG. 8 shows generating a CD4+ T cell population that is highly enriched for HIV-specific, AGT103-transduced CD4 T cells. Panel (A) shows that therapeutic vaccination against HIV has minimal effect on the distribution of CD4+, CD8+ and CD4+/CD8+ T cells. An important CD4 T cell population is shown in the upper left quadrant of these analytical flow cytometry dot plots, and changes from 52% to 57% of total T cells after the vaccination series. These are representative data. Panel (B) shows the expression of CD4 and CD8 in a CD3+ population of peripheral blood mononuclear cells from a participant in an HIV therapeutic vaccine trial that were cultured for 12 days in medium+/−interleukin-2/ interleukin-12 or +/−interleukin-7/interleukin-15. Some cultures were stimulated with overlapping peptides representing the entire p55 Gag protein of HIV-1 (JPT PepMix) as a source of epitope peptides for T cell stimulation. Panel (C) shows that a combination of PepMix and interleukin-2/ interleukin-12 provides for optimal expansion of antigen-specific CD4 T cells. The upper panels show the increase in cytokine (interferon-gamma) secreting cells in post-vaccination specimens exposed to PepMix. Panel (D) shows AGT103 transduction of antigen-expanded CD4 T cells can produce HIV-specific and HIV-resistant helper CD4 T cells for infusion into patients as part of a functional cure for HIV. The upper panels contain the results of analyzing the CD4+ T cell population in culture. The x axis is Green Fluorescent Protein (GFP) emission indicating that individual cells were transduced with the AGT103.

Example 5—Generating a Population of CD4+ T Cells Enriched for HIV-Specificity and Transduced with AGT103/CMV-GFP Therapeutic vaccination against HIV had minimal effect on the distribution of CD4+, CD8+ and CD4+/CD8+ T cells. As shown in FIG. 8A, the CD4 T cell population is shown in the upper left quadrant of the analytical flow cytometry dot plots, and changes from 52% to 57% of total T cells after the vaccination series. These are representative data.

Figure 8B:
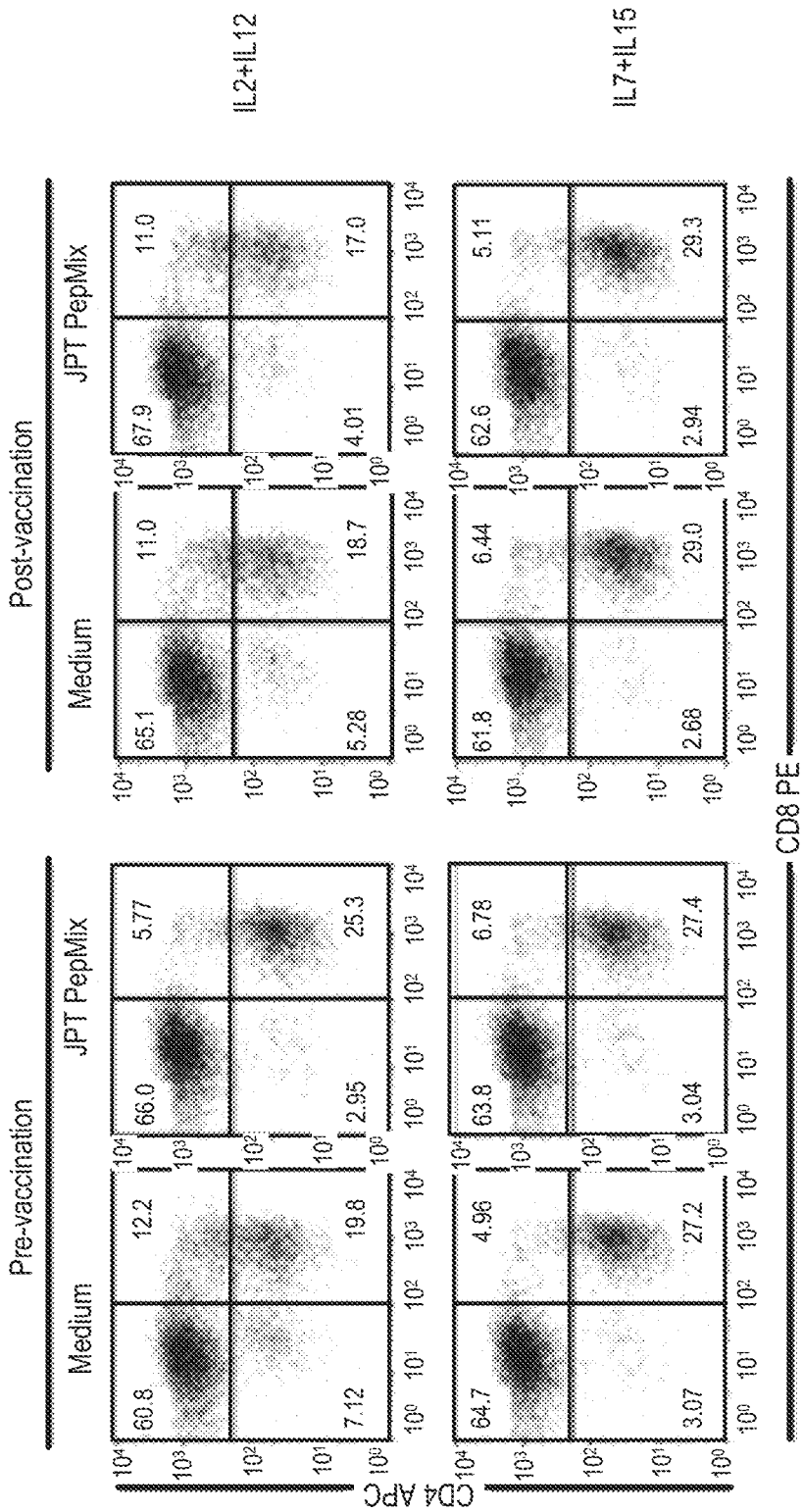

Peripheral blood mononuclear cells from a participant in an HIV therapeutic vaccine trial were cultured for 12 days in medium+/−interleukin-2/interleukin-12 or +/−interleukin-7/interleukin-15. Some cultures were stimulated with overlapping peptides representing the entire p55 Gag protein of HIV-1 (JPT PepMix) as a source of epitope peptides for T cell stimulation. These peptides are 10-20 amino acids in length and overlap by 20-50% of their length to represent the entire Gag precursor protein (p55) from HIV-1 BaL strain. The composition and sequence of individual peptides can be adjusted to compensate for regional variations in the predominant circulating HIV sequences or when detailed sequence information is available for an individual patient receiving this therapy. At culture end, cells were recovered and stained with anti-CD4 or anti-CD8 monoclonal antibodies and the CD3+ population was gated and displayed here. The PepMix stimulation for either pre- or post-vaccination samples was similar to the medium control indicating that PepMix was not toxic to cells and was not acting as a polyclonal mitogen. The results of this analysis can be found in FIG. 8B.

Figure 8C:
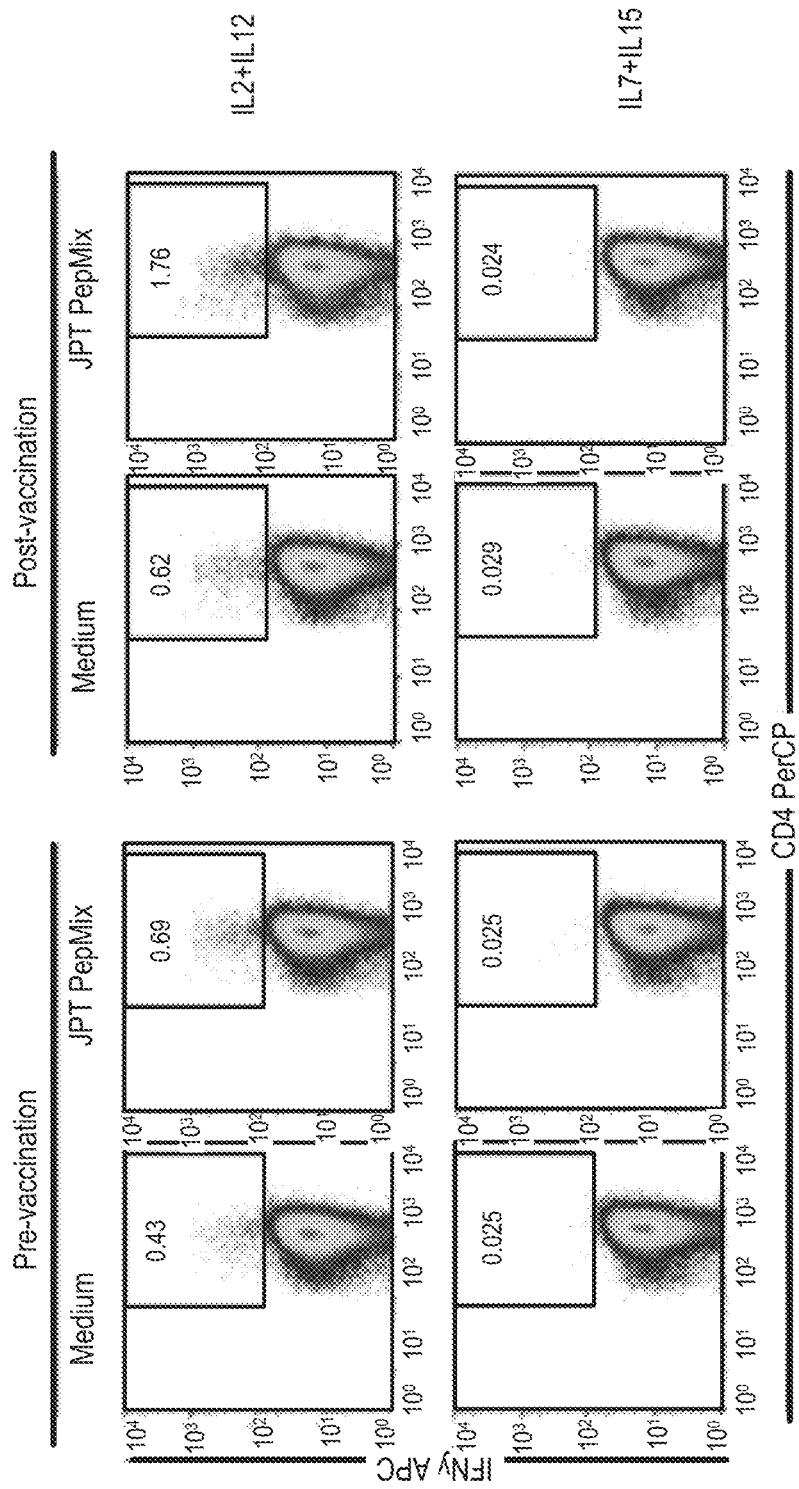

PepMix and interleukin-2/interleukin-12 provided for optimal expansion of antigen-specific CD4 T cells. As shown in the upper panels of FIG. 8C, there was an increase in cytokine (interferon-gamma) secreting cells in post-vaccination specimens exposed to PepMix. In the pre-vaccination sample, cytokine secreting cells increased from 0.43 to 0.69% as a result of exposure to antigenic peptides. In contrast, the post-vaccination samples showed an increase of cytokine secreting cells from 0.62 to 1.76% of total CD4 T cells as a result of peptide stimulation. These data demonstrate the strong impact of vaccination on the CD4 T cell responses to HIV antigen.

Figure 8D:
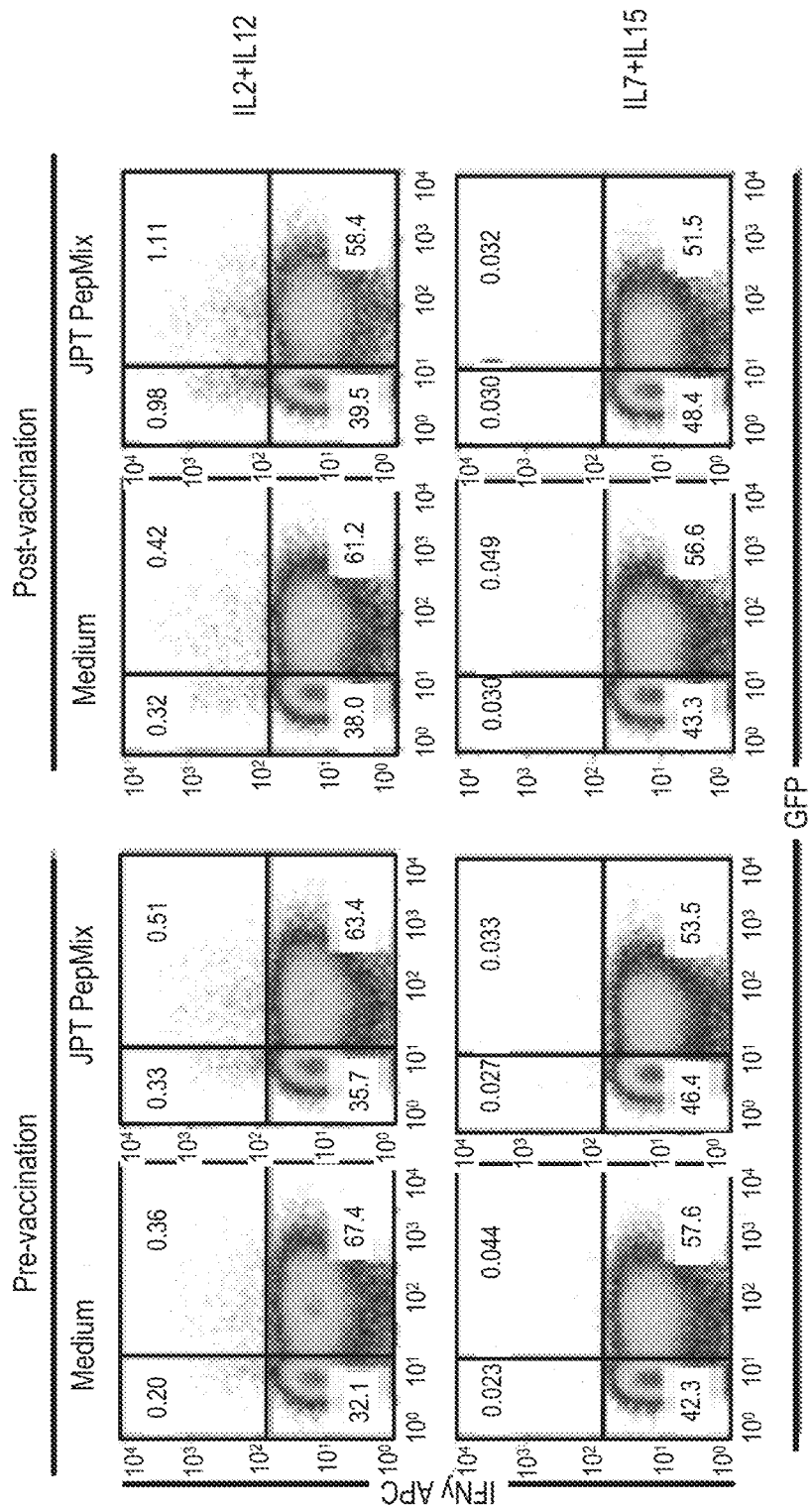

Finally, AGT103/CMV-GFP transduction of antigen-expanded CD4 T cells produced HIV-specific and HIV-resistant helper CD4 T cells that are needed for infusion into patients as part of a functional cure for HIV (in accordance with other various aspects and embodiments, AGT103 may be used alone or without further additional elements; for example, clinical embodiments may not include the CMV-GFP segment). The upper panels of FIG. 8D show the results of analyzing the CD4+ T cell population in culture. The x axis of FIG. 8D shows Green Fluorescent Protein (GFP) emission indicating that individual cells were transduced with the AGT103/CMV-GFP. In the post-vaccination samples 1.11% of total CD4 T cells that were both cytokine secreting was recovered, indicating that the cells are responding specifically to HIV antigen, and transduced with AGT103/CMV-GFP. This is the target cell population and the clinical product intended for infusion and functional cure of HIV. With the efficiency of cell expansion during the antigen stimulation and subsequent polyclonal expansion phases of ex vivo culture, $4\times10^8$ antigen-specific, lentivirus transduced CD4 T cells can be produced. This exceeds the target for cell production by 4-fold and will allow achievement of a count of antigen-specific and HIV-resistant CD4 T cells of approximately 40 cells/microliter of blood or around 5.7% of total circulating CD4 T cells.

Table 4 below shows the results of the ex vivo production of HIV-specific and HIV-resistant CD4 T cells using the disclosed vectors and methods.

TABLE 4

| Material/manipulation | Total CD4 T cells | Percentage HIV-specific | Percentage HIV-specific and HIV-resistant |
|---|---|---|---|
| Leukapheresis pack from HIV+ patient | ~7 × $10^8$ | ~0.12 | N/A |
| Peptide expansion ex vivo | ~8 × $10^8$ | ~2.4 | N/A |
| Mitogen expansion | ~1.5 × $10^{10}$ | ~2.4 | N/A |
| Lentivirus transduction | ~1.5 × $10^{10}$ | ~2.4 | ~1.6 |

While certain of the preferred embodiments of the present invention have been described and specifically exemplified above, it is not intended that the invention be limited to such embodiments. Various modifications may be made thereto without departing from the scope and spirit of the present invention.

What is claimed is:

1. A method of treating HIV infection, comprising:
    (a) immunizing a subject with a therapeutically effective amount of an HIV vaccine;
    (b) purifying peripheral blood mononuclear cells (PBMC) obtained from the subject;
    (c) contacting the PBMC ex vivo with a therapeutically effective amount of an HIV vaccine;
    (d) transducing the PBMC ex vivo with a viral delivery system that comprises a microRNA cluster encoding:
        (i) at least one microRNA capable of inhibiting the production of chemokine receptor CCR5 and at least one microRNA capable of inhibiting the production of HIV tat gene,
        (ii) at least one microRNA capable of inhibiting the production of HIV tat gene and at least one microRNA capable of inhibiting the production of HIV vif gene or
        (iii) at least one microRNA capable of inhibiting the production of chemokine receptor CCR5, at least one microRNA capable of inhibiting the production of HIV tat gene and at least one microRNA capable of inhibiting the production of HIV vif gene;
    (e) culturing the transduced PBMC for about 1 to about 35 days; and
    (f) infusing the transduced PBMC into the subject,
    wherein the subject receives a cyclophosphamide pretreatment prior to infusing the transduced PBMC.

2. The method of claim 1, wherein step (a) and step (b) comprise the same HIV vaccine.

3. The method of claim 1, wherein step (a) and step (c) comprise different HIV vaccines.

4. The method of claim 1, wherein the subject was receiving cART or HAART prior to infusing the transduced PBMC into the subject.

5. The method of claim 1, wherein the viral delivery system further comprises at least one microRNA capable of inhibiting the production of chemokine receptor CXCR4.

6. The method of claim 1, wherein the microRNA cluster further encodes a microRNA capable of inhibiting an HIV gene selected from the group consisting of gag, pol, env, rev, nef, vpr, and vpu.

7. The method of claim 1, wherein the transduced PBMC are cultured for about 1 to about 10 days prior to infusing the transduced PBMC into the subject.

8. A method of treating HIV in a HIV+subject, comprising:
    (a) immunizing a subject with a therapeutically effective amount of an HIV vaccine;
    (b) purifying peripheral blood mononuclear cells (PBMC) obtained from the subject;
    (c) contacting the PBMC ex vivo with a therapeutically effective amount of an HIV vaccine;
    (d) transducing the PBMC ex vivo with a viral delivery system that comprises a microRNA cluster encoding:

(i) at least one microRNA capable of inhibiting the production of chemokine receptor CCR5 and at least one microRNA capable of inhibiting the production of HIV tat gene,
(ii) at least one microRNA capable of inhibiting the production of HIV tat gene and at least one microRNA capable of inhibiting the production of HIV vif gene or
(iii) at least one microRNA capable of inhibiting the production of chemokine receptor CCR5, at least one microRNA capable of inhibiting the production of HIV tat gene and at least one microRNA capable of inhibiting the production of HIV vif gene;
(e) culturing the transduced PBMC for about 1 to about 35 days; and
(f) infusing the transduced PBMC into the subject,
wherein the subject receives a cyclophosphamide pretreatment prior to infusing the transduced PBMC.

9. The method of claim 8, wherein step (a) and step (12) comprise the same HIV vaccine.

10. The method of claim 8, wherein step (a) and step (c) comprise different HIV vaccines.

11. The method of claim 8, wherein the viral delivery system further comprises at least one microRNA capable of inhibiting the production of chemokine receptor CXCR4.

12. The method of claim 8, wherein the microRNA cluster further encodes a microRNA capable of inhibiting an HIV gene selected from the group consisting of gag, pol, env, rev, nef, vpr, and vpu.

13. The method of claim 1, wherein the microRNA comprises miR30 CCR5 encoded by the sequence comprising SEQ ID NO. 10.

14. The method of claim 8, wherein the microRNA comprises miR30 CCR5 encoded by the sequence comprising SEQ ID NO. 10.

15. The method of claim 13, wherein the microRNA comprises miR21 vif encoded by the sequence comprising SEQ ID NO. 11.

16. The method of claim 14, wherein the microRNA comprises miR21 vif encoded by the sequence comprising SEQ ID NO. 11.

17. The method of claim 15, wherein the microRNA comprises miR185 tat encoded by the sequence comprising SEQ ID NO. 12.

18. The method of claim 16, wherein the microRNA comprises miR185 tat encoded by the sequence comprising SEQ ID NO. 12.

* * * * *

SEQUENCE LISTING

<160> NUMBER OF SEQ ID NOS: 12

<210> SEQ ID NO 1
<211> LENGTH: 1527
<212> TYPE: DNA
<213> ORGANISM: Artificial Sequence
<220> FEATURE:
<223> OTHER INFORMATION: Exemplary vector

<400> SEQUENCE: 1

| | |
|---|---:|
| accggtgcct agagaaggtg gcgcggggta aactgggaaa gtgatgtcgt gtactggctc | 60 |
| cgccttttte ccgagggtgg gggagaaccg tatataagtg cagtagtcgc cgtgaacgtt | 120 |
| cttttcgca acgggtttgc cgccagaaca caggtaagtg ccgtgtgtgg ttcccgcggg | 180 |
| cctggcctct ttacgggtta tggcccttgc gtgccttgaa ttacttccac gccccctggct | 240 |
| gcagtacgtg attcttgatc ccgagcttcg ggttggaagt gggtgggaga gttcgaggcc | 300 |
| ttgcgcttaa ggagccccctt cgcctcgtgc ttgagttgag gcctggcctg gcgctgggg | 360 |
| ccgccgcgtg cgaatctggt ggcaccttcg cgcctgtctc gctgctttcg ataagtctct | 420 |
| agccatttaa aattttttgat gacctgctgc gacgcttttt ttctggcaag atagtcttgt | 480 |
| aaatgcgggc caagatcgat ctgcacactg gtatttcggt ttttgggggcc gcgggcggcg | 540 |
| acggggcccg tgcgtcccag cgcacatgtt cggcgaggcg gggcctgcga gcgcggccac | 600 |
| cgagaatcgg acggggtag tctcaagctg gccggcctgc tctggtgcct ggcctcgcgc | 660 |
| cgccgtgtat cgccccgccc tgggcggcaa ggctggcccg tcggcacca gttgcgtgag | 720 |
| cggaaagatg gccgcttccc ggccctgctg cagggagctc aaaatggagg acgcggcgct | 780 |
| cgggagagcg ggcgggtgag tcacccacac aaaggaaaag ggcctttccg tcctcagccg | 840 |
| tcgcttcatg tgactccacg gagtaccggg cgccgtccag gcacctcgat tagttctcga | 900 |
| gcttttggag tacgtcgtct ttaggttggg gggaggggtt ttatgcgatg gagttttcccc | 960 |
| acactgagtg ggtggagact gaagttaggc cagcttgggc acttgatgta attctccttg | 1020 |
| gaatttgccc ttttttgagtt tggatcttgg ttcattctca agcctcagac agtggttcaa | 1080 |
| agtttttttc ttccatttca ggtgtcgtga ggaattggcg aagctaattc tgcagattcg | 1140 |
| actgtacaag gtatattgct gttgacagtg agcgactgta aactgagctt gctctactgt | 1200 |
| gaagccacag atgggtagag caagcacagt ttaccgctgc ctactgcctc ggacttcaag | 1260 |
| gggcttcccg ggcatctcca tggctgtacc accttgtcgg gggatgtgta cttctgaact | 1320 |
| tgtgttgaat ctcatggagt tcagaagaac acatccgcac tgacattttg gtatctttca | 1380 |
| tctgaccagc tagcgggcct ggctcgagca gggggcgagg gattccgctt cttcctgcca | 1440 |
| tagcgtggtc ccctccccta tggcaggcag aagcggcacc ttccctccca atgaccgcgt | 1500 |
| cttcgtcgcg gccgctcgag catgcat | 1527 |

<210> SEQ ID NO 2
<211> LENGTH: 915
<212> TYPE: DNA
<213> ORGANISM: Homo sapiens

<400> SEQUENCE: 2

| | |
|---|---:|
| atgcagaccc tcatcttttt cgacatggag gccactggct tgcccttctc ccagcccaag | 60 |
| gtcacggagc tgtgcctgct ggctgtccac agatgtgccc tggagagccc cccacctct | 120 |
| caggggccac ctcccacagt tcctccacca ccgcgtgtgg tagacaagct ctccctgtgt | 180 |
| gtggctccgg ggaaggcctg cagccctgca gccagcgaga tcacaggtct gagcacagct | 240 |
| gtgctggcag cgcatgggcg tcaatgtttt gatgacaacc tggccaacct gctcctagcc | 300 |
| ttcctgcggc gccagccaca gcctggtgc ctggtggcac acaatggtga ccgctacgac | 360 |
| ttcccccctgc tccaagcaga gctggctatg ctgggcctca ccagtgctct ggatggtgcc | 420 |
| ttctgtgtgg atagcatcac tgcgctgaag gccctggagc gagcaagcag ccccctcagaa | 480 |
| cacgccccaa ggaagagcta cagcctaggc agcatctaca ctcgcctgta tgggcagtcc | 540 |
| cctccagact cgcacacggc tgagggtgat gtcctggccc tgctcagcat ctgtcagtgg | 600 |

| | | |
|---|---|---|
| agaccacagg | ccctgctgcg gtgggtggat gctcacgcca ggcctttcgg caccatcagg | 660 |
| cccatgtatg | gggtcacagc ctctgctagg accaagccaa gaccatctgc tgtcacaacc | 720 |
| actgcacacc | tggccacaac caggaacact agtcccagcc ttcgagagag caggggtacc | 780 |
| aaggatcttc | ctccagtgaa ggaccctgga gccctatcca gggaggggct gctggcccca | 840 |
| ctgggtctgc | tggccatcct gaccttggca gtagccacac tgtatggact atccctggcc | 900 |
| acacctggcg | attaa | 915 |

<210> SEQ ID NO 3
<211> LENGTH: 1255
<212> TYPE: DNA
<213> ORGANISM: Homo sapiens

<400> SEQUENCE: 3

| | | |
|---|---|---|
| caccttggtc | acactccaga gctcgcttca tccccacgag cggcacctga tctccagtga | 60 |
| cggggagact | gaggcctggc aaagaggacc tgttgccttt tgtaactgg ccccagcatg | 120 |
| ggggaggcat | tggccccagc atggggggagg cattgacccc aggcctgcca ggcctggcag | 180 |
| ccacagcctg | gctaggtgga ggttactgcc ttccgcacca ctctggcttc ctccccgtgc | 240 |
| ctgtgaagag | ctcggggcct gcttcctaat ttgtaaacac ggggcgtgtg tctcagtggc | 300 |
| tgtgagctag | cgaggggtg gcgagcgagc cggctgcgca ggtcctgagg ccccaggcct | 360 |
| cattgttggc | caacaggcag ctgggggcgg gctgcggccg ctgattaaag gccgcctaga | 420 |
| gcagcctgtg | tggcgacagg tgcccagaag cccaggaagc cggtcagtgc ccgcccagt | 480 |
| cctcagggtt | tgtgcctctc gctcggacag tttgaggact tgctatcccc gtgggaacat | 540 |
| caccatgtcc | gaggcacccc gggccgagac ctttgtcttc ctggacctgg aagccactgg | 600 |
| gctccccagt | gtggagcccg agattgccga gctgtccctc tttgctgtcc accgctcctc | 660 |
| cctggagaac | ccggagcacg acgagtctgg tgccctagta ttgccccggg tcctggacaa | 720 |
| gctcacgctg | tgcatgtgcc cggagcgccc cttcactgcc aaggccagcg agatcaccgg | 780 |
| cctgagcagt | gagggcctgg cgcgatgccg gaaggctggc tttgatggcg ccgtggtgcg | 840 |
| gacgctgcag | gccttcctga ccgccaggc agggcccatc tgccttgtgg cccacaatgg | 900 |
| ctttgattat | gatttccccc tgctgtgtgc cgagctgcgg cgcctgggtg cccgcctgcc | 960 |
| ccgggacact | gtctgcctgg acacgctgcc ggccctgcgg ggcctggacc gcgcccacag | 1020 |
| ccacggcacc | cgggcccggg gccgccaggg ttacagcctc ggcagcctct tccaccgcta | 1080 |
| cttccgggca | gagccaagcg cagcccactc agccgagggc gacgtgcaca ccctgttcct | 1140 |
| gatcttcctg | caccgcgccg cagagctgct cgcctgggcc gatgagcagg cccgtgggtg | 1200 |
| ggcccacatc | gagcccatgt acttgccgcc tgatgacccc agcctggagg cctga | 1255 |

<210> SEQ ID NO 4
<211> LENGTH: 3180
<212> TYPE: DNA
<213> ORGANISM: Homo sapiens

<400> SEQUENCE: 4

| | | |
|---|---|---|
| attgcgcctg | cgcagggagc ccaaggcaag agccgctagg ctgccctgcc cgaagggctc | 60 |
| aactgtcagt | gagcctgcgc aggaggccaa taggctgcca atactccttg gactccccgc | 120 |
| cagggccctg | ctgtcagtgc gcctgcgcg gggtccggcg ccgaggttct tgactgctgt | 180 |
| gccggacgcc | aggtgtagcc atgcagcgag ccgattccga gcagccctcc aagcgtcccc | 240 |

```
gttgcgatga cagcccgaga accccctcaa acaccccttc cgcagaggca gactggtccc    300
cgggcctgga actccatccc gactacaaga catggggtcc ggagcaggtg tgctccttcc    360
tcaggcgcgg tggctttgaa gagccggtgc tgctgaagaa catccgagaa aatgaaatca    420
caggcgcatt actgccttgt cttgatgagt ctcgttttga aaatcttgga gtaagttcct    480
tgggggagag gaagaagctg cttagttata ccagcgatt  ggttcaaatc cacgttgata    540
caatgaaggt aattaatgat cctatccatg ccacattga  gctccaccct ctcctcgtcc    600
gaatcattga tacacctcaa tttcaacgtc ttcgatacat caaacagctg ggaggtggtt    660
actatgtttt tccaggagct tcacacaatc gatttgagca tagtctaggg gtggggtatc    720
tagcaggatg tctagttcac gcactgggtg aaaaacaacc agagctgcag ataagtgaac    780
gagatgttct ctgtgttcag attgctggac tttgtcatga tctcggtcat gggccatttt    840
ctcacatgtt tgatggacga tttattccac ttgctcgccc ggaggtgaaa tggacgcatg    900
aacaaggctc agttatgatg tttgagcacc ttattaattc taatggaatt aagcctgtca    960
tggaacaata tggtctcatc cctgaagaag atatttgctt tataaaggaa caaattgtag   1020
gaccacttga atcacctgtc gaagattcat tgtggccata taagggcgt  cctgaaaaca   1080 aaagcttcct ttatgagata gtatctaata aagaaatgg  cattgatgtg gacaaatggg   1140
attattttgc cagggactgc catcatcttg gaatccaaaa taattttgat tacaagcgct   1200
ttattaagtt tgcccgtgtc tgtgaagtag acaatgagtt gcgtatttgt gctagagata   1260
aggaagttgg aaatctgtat gacatgttcc acactcgcaa ctctttacac cgtagagctt   1320
atcaacacaa agttggcaac attattgata caatgattac agatgctttc ctcaaagcag   1380
atgactacat agagattaca ggtgctggag gaaaaaagta tcgcatttct acagcaattg   1440
acgacatgga agcctatact aagctgcag  ataacatttt tctggagatt ttatactcta   1500
ctgatcccaa attgaaagac gcacgagaga ttttaaaaca aattgaatac cgtaatctat   1560
tcaagtatgt gggtgagacg cagccaacag gacaaataaa gattaaaagg gaggactatg   1620
aatctcttcc aaaagaggtt gccagtgcta aacccaaagt attgctagac gtgaaactga   1680
aggctgaaga ttttatagtg gatgttatca acatggatta tggaatgcaa gaaaagaatc   1740
caattgatca tgttagcttc tattgtaaga ctgcccccaa cagagcaatc aggattacta   1800
aaaaccaggt ttcacaactt ctgccagaga aatttgcaga gcagctgatt cgagtatatt   1860
gtaagaaggt ggacagaaag agtttgtatg ccgcaagaca atattttgtt cagtggtgtg   1920
cagacagaaa tttcaccaag ccgcaggatg gcgatgttat agccccactc ataacacctc   1980
aaaaaaagga atggaacgac agtacttcag tccaaaatcc aactcgcctc cgagaagcat   2040
ccaaaagcag agtccagctt tttaaagatg acccaatgtg aatgtctgta gtcagttgtt   2100
tacaaactcc ctctcctgca caattcattt agaggcttca atcatagaat tctgcaaatt   2160
aatgacaact catgctttaa ttttgtattt tgaatgtaca cgcatgctga agctaagtaa   2220
cttttaatca aagaaataag atggtattag gcaaatctta ctatactatg aaagcatta    2280 ccttgcctat ttttaatatt attaaagcct ttctccttca gtagtctatt ttcttagaat   2340
aacaactctt ttatctattc tgaactctat ttttttcttt ttttaagaga caaggttttg   2400
ctctgttgcc cagcttggac tcgaactttc ctgggctcaa gcgaccctcc tgcctcagcc   2460
ccccaagtag ctgggactaa agtcatgtgc caccacaccc agcttactct gaacttttat   2520
gacagatgat tgttttttgt ttttaatgta gaaatgagac aagggtacaa attggaacta   2580
gaaattgaca ttgtcattga caaacatggc taaaaacaaa acatcaaatc ctgcccccgt   2640
```

```
gaagagttcc ctgtcacctc aagtttgagg atagtcctct aagagtgacc taagcataag    2700
tgaaagacac ctcccctcac ccttctagcc ccctacaagg tgccaggttg gggtaaagag    2760
ttggagatga tggccaggag tggcctccaa cacgctggtg agaggcctga ttaggttttg    2820
gggaagatct gagagctctg gcctcttcgt gagtggaaca taaagccgcc tcttgttggg    2880
agatcctacc ccagtgacag aggaatcccc caaactaggc tgtgccctgg ctccgtggcg    2940
gctccagacc cgggtagtgc ctttgtcccc tgaatactca ctcccccggt ccagagggcc    3000
ttcccactgc ccagcctgga aaggcctcc cctgacctgc tctctcagta tcctggagag      3060
ctggccagag gccatcacag gcatcatcct cagagctcct cagacctggg actttgtttt    3120
tgctggttca gtgcattttg tgtatttaag agcaaacact agccaggcgt ggcggcgtgt    3180
```

<210> SEQ ID NO 5
<211> LENGTH: 3300
<212> TYPE: DNA
<213> ORGANISM: Homo sapiens

<400> SEQUENCE: 5

```
cgagcagaaa tgaaaccgaa actgaattgt ccgggaaatt cgcggtgggg gcggagagcg      60
cagggagaag taagcccagt gcaggatcct gaggcccgtg tttgcaggac cagggccggc    120
cttccgattc cccattcatt ccagaagcac cgaaccacgc tgtgcccgga tcccaagtgc    180
agcggcaccc agcgtgggcc tggggttgcc ggttgacccg gtcctcagcc tggtagcaga    240
ggccaggcca gtgccacaag gcacctaagt ccacctgggc ctggagcagg acaggttgca    300
aaagaaaata tctcgggacc cccaaactcc ttatgctaag ggaaacatcg agcctgggaa    360
ctgagccatc aacgctgcca ttcttttttcc caaacagaac cctgttgtca gaggtacacc    420
cagagcaact ccacaccggg tgcatgccac agcaactcca tcttaaatag gagctggtaa    480
aacgaggctg ataccactg ggctgcattc ccagacggca tagcgaggag gtgctgaaga     540
gcgcaggttt ggagaatgat cacctggatt ggaaccatag ctctaccaat atggaaccca    600
gctccttagg cctcggtctt ctcatggaga acatggtgtg ataatcctac tcctctggga    660
gggtggctgt taagccttgg accgcagttg ccggccagga atcccagtgt cacggtggac    720
acgcctccct cgcgcccttg ccgcccacct gctcacccag ctcagggct ttggaattct      780 gtggccacac tgccgaggag atcggttctg gtcggaggct acaggaagac tcccactccc    840
tgaaatctgg agtgaagaac gccgccatcc agccaccatt ccaggaggt gcaggagaac      900 agctctgtga taccatttaa cttgttgaca ttacttttat ttgaaggaac gtatattaga    960
gcttactttg caaagaagga agatggttgt ttccgaagtg acatcgcaa aagctgatcc     1020 agctgctgca tcccacccTc tattactgaa tggagatgct actgtggccc agaaaaatcc    1080
aggctcggtg gctgagaaca acctgtgcag ccagtatgag gagaaggtgc gccctgcat     1140 cgacctcatt gactccctgc gggctctagg tgtggagcag gacctggccc tgccagccat    1200
cgccgtcatc ggggaccaga gctcgggcaa gagctccgtg ttggaggcac tgtcaggagt    1260
tgcccttccc agaggcagcg ggatcgtgac cagatgcccg ctggtgctga aactgaagaa    1320
acttgtgaac gaagataagt ggagaggcaa ggtcagttac caggactacg agattgagat    1380
ttcggatgct tcagaggtag aaaaggaaat taataaagcc cagaatgcca tcgccgggga    1440
aggaatggga atcagtcatg agctaatcac cctggagatc agctcccgag atgtcccgga    1500
tctgactcta atagaccttc ctggcataac cagagtggct gtgggcaatc agcctgctga    1560
```

-continued

```
cattgggtat aagatcaaga cactcatcaa gaagtacatc cagaggcagg agacaatcag    1620
cctggtggtg gtccccagta atgtggacat cgccaccaca gaggctctca gcatggccca    1680
ggaggtggac cccgagggag acaggaccat cggaatcttg acgaagcctg atctggtgga    1740
caaaggaact gaagacaagg ttgtggacgt ggtgcggaac ctcgtgttcc acctgaagaa    1800
gggttacatg attgtcaagt gccggggcca gcaggagatc caggaccagc tgagcctgtc    1860
cgaagccctg cagagagaga agatcttctt tgagaaccac ccatatttca gggatctgct    1920
ggaggaagga aaggccacgg ttccctgcct ggcagaaaaa cttaccagcg agctcatcac    1980
acatatctgt aaatctctgc ccctgttaga aaatcaaatc aaggagactc accagagaat    2040
aacagaggag ctacaaaagt atggtgtcga cataccggaa gacgaaaatg aaaaaatgtt    2100
cttcctgata gataaagtta atgcctttaa tcaggacatc actgctctca tgcaaggaga    2160
ggaaactgta ggggaggaag acattcggct gtttaccaga ctccgacacg agttccacaa    2220
atggagtaca ataattgaaa acaattttca agaaggccat aaaattttga gtagaaaaat    2280
ccagaaattt gaaaatcagt atcgtggtag agagctgcca ggctttgtga attacaggac    2340
atttgagaca atcgtgaaac agcaaatcaa ggcactggaa gagccggctg tggatatgct    2400
acacaccgtg acgatatgg tccggcttgc ttttcacagat gtttcgataa aaaattttga    2460
agagtttttt aacctccaca gaaccgccaa gtccaaaatt gaagacatta gagcagaaca    2520
agagagagaa ggtgagaagc tgatccgcct ccacttccag atggaacaga ttgtctactg    2580
ccaggaccag gtatacaggg gtgcattgca gaaggtcaga gagaaggagc tggaagaaga    2640
aaagaagaag aaatcctggg attttggggc tttccagtcc agctcggcaa cagactcttc    2700
catggaggag atctttcagc acctgatggc ctatcaccag gaggccagca gcgcatctc    2760 cagccacatc cctttgatca tccagttctt catgctccag acgtacggcc agcagcttca    2820
gaaggccatg ctgcagctcc tgcaggacaa ggacacctac agctggctcc tgaaggagcg    2880
gagcgacacc agcgacaagc ggaagttcct gaaggagcgg cttgcacggc tgacgcaggc    2940
tcggcgccgg cttgcccagt tccccggtta accacactct gtccagcccc gtagacgtgc    3000
acgcacactg tctgccccg ttcccgggta gccactggac tgacgacttg agtgctcagt    3060
agtcagactg gatagtccgt ctctgcttat ccgttagccg tggtgattta gcaggaagct    3120
gtgagagcag tttggtttct agcatgaaga cagagcccca ccctcagatg cacatgagct    3180
ggcgggattg aaggatgctg tcttcgtact gggaaaggga ttttcagccc tcagaatcgc    3240
tccaccttgc agctctcccc ttctctgtat tcctagaaac tgacacatgc tgaacatcac    3300
```

<210> SEQ ID NO 6
<211> LENGTH: 2961
<212> TYPE: DNA
<213> ORGANISM: Homo sapiens

<400> SEQUENCE: 6

```
aagagatgat ttctccatcc tgaacgtgca gcgagcttgt caggaagatc ggaggtgcca     60
agtagcagag aaagcatccc ccagctctga cagggagaca gcacatgtct aaggcccaca    120
agccttggcc ctaccggagg agaagtcaat tttcttctcg aaaatacctg aaaaagaaa    180 tgaattcctt ccagcaacag ccaccgccat tcggcacagt gccaccacaa atgatgtttc    240
ctccaaactg gcaggggca gagaaggacg ctgctttcct cgccaaggac ttcaactttc    300
tcactttgaa caatcagcca ccaccaggaa acaggagcca accaagggca atggggcccg    360
agaacaacct gtacagccag tacgagcaga aggtgcgccc ctgcattgac ctcatcgact    420
```

```
ccctgcgggc tctgggtgtg gagcaggacc tggccctgcc agccatcgcc gtcatcgggg    480
accagagctc gggcaagagc tctgtgctgg aggcactgtc aggagtcgcg cttcccagag    540
gcagcggaat cgtaaccagg tgtccgctgg tgctgaaact gaaaaagcag ccctgtgagg    600
catgggccgg aaggatcagc taccggaaca ccgagctaga gcttcaggac cctggccagg    660
tggagaaaga gatacacaaa gcccagaacg tcatggccgg gaatggccgg ggcatcagcc    720
atgagctcat cagcctggag atcacctccc ctgaggttcc agacctgacc atcattgacc    780
ttcccggcat caccagggtg gctgtggaca accagccccg agacatcgga ctgcagatca    840
aggctctcat caagaagtac atccagaggc agcagacgat caacttggtg gtggttccct    900
gtaacgtgga cattgccacc acggaggcgc tgagcatggc ccatgaggtg acccggaag     960
gggacaggac catcggtatc ctgaccaaac cagatctaat ggacaggggc actgagaaaa   1020
gcgtcatgaa tgtggtgcgg aacctcacgt accccctcaa gaagggctac atgattgtga   1080
agtgccgggg ccagcaggag atcacaaaca ggctgagctt ggcagaggca accaagaaag   1140
aaattacatt ctttcaaaca catccatatt tcagagttct cctggaggag gggtcagcca   1200
cggttccccg actggcagaa agacttacca ctgaactcat catgcatatc caaaaatcgc   1260
tcccgttgtt agaaggacaa ataagggaga gccaccagaa ggcgaccgag gagctgcggc   1320
gttgcggggc tgacatcccc agccaggagg ccgacaagtg ttctttcta attgagaaaa    1380
tcaagatgtt taatcaggac atcgaaaagt tagtagaagg agaagaagtt gtaagggaga   1440
atgagacccg tttatacaac aaaatcgag aggattttaa aaactgggta ggcatacttg    1500
caactaatac ccaaaaagtt aaaaatatta tccacgaaga agttgaaaaa tatgaaaagc   1560
agtatcgagg caaggagctt ctgggatttg tcaactacaa gacatttgag atcatcgtgc   1620
atcagtacat ccagcagctg gtggagcccg cccttagcat gctccagaaa gccatggaaa   1680
ttatccagca agcttttcat taacgtggcca aaaaacattt tggcgaattt ttcaaccta    1740
accaaactgt tcagagcacg attgaagaca taaaagtgaa acacacagca aaggcagaaa   1800
acatgatcca acttcagttc agaatggagc agatggtttt ttgtcaagat cagatttaca   1860
gtgttgttct gaagaaagtc cgagaagaga ttttaaccc tctggggacg ccttcacaga    1920
atatgaagtt gaactctcat tttcccagta atgagtcttc ggtttcctcc tttactgaaa   1980
taggcatcca cctgaatgcc tacttcttgg aaaccagcaa acgtctcgcc aaccagatcc   2040
catttataat tcagtatttt atgctccgag agaatggtga ctccttgcag aaagccatga   2100
tgcagatact acaggaaaaa atcgctatt cctggctgct tcaagagcag agtgagaccg    2160
ctaccaagag aagaatcctt aaggagagaa tttaccggct cactcaggcg cgacacgcac   2220
tctgtcaatt ctccagcaaa gagatccact gaagggcggc gatgcctgtg gttgttttct   2280
tgtgcgtact cattcattct aaggggagtc ggtgcaggat gccgcttctg ctttggggcc   2340
aaactcttct gtcactatca gtgtccatct ctactgtact ccctcagcat cagagcatgc   2400
atcagggggtc cacacaggct cagctctctc caccacccag ctcttccctg accttcacga   2460
agggatggct ctccagtcct tgggtcccgt agcacacagt tacagtgtcc taagatactg   2520
ctatcattct tcgctaattt gtatttgtat tcccttcccc ctacaagatt atgagacccc   2580
agaggggaa ggtctgggtc aaattcttct tttgtatgtc cagtctcctg cacagcacct    2640
gcagcattgt aactgcttaa taatgacat ctcactgaac gaatgagtgc tgtgtaagtg    2700
atggagatac ctgaggctat tgctcaagcc caggccttgg acatttagtg actgttagcc   2760
```

```
ggtcccttttc agatccagtg ccatgcccc ctgcttccca tggttcactg tcattgtgtt    2820
tcccagcctc tccactcccc cgccagaaag gagcctgagt gattctcttt tcttcttgtt    2880
tccctgatta tgatgagctt ccattgttct gttaagtctt gaagaggaat ttaataaagc    2940
aaagaaactt tttaaaaacg t                                              2961

<210> SEQ ID NO 7
<211> LENGTH: 1848
<212> TYPE: DNA
<213> ORGANISM: Homo sapiens

<400> SEQUENCE: 7
gtgctctgct ggctcagcct ggtgtggacc cacctcccgg gcgctggctg caatgacttt      60
ctctttccct ttgcaattgc cttgggtcct gccgcacaga gcggcctgtc tttatcagag     120
gtccctctgc caggggagg gccccagaga aaccagaaa gagggtgaga gactgaggaa       180
gataaagcgt cccagggcct cctacaccag cgcctgagca ggaagcggga ggggccatga     240
ctacgaggcc ctgggaggtc actttaggga gggctgtcct aaaaccagaa gcttggagca     300
gaaagtgaaa ccctggtgct ccagacaaag atcttagtcg ggactagccg gccaaggatg     360
aagcctcact tcagaaacac agtggagcga atgtatcgag acacattctc ctacaacttt     420
tataatagac ccatcctttc tcgtcggaat accgtctggc tgtgctacga agtgaaaaca     480
aagggtccct caaggccccc tttggacgca agatctttc gaggccaggt gtattccgaa      540
cttaagtacc acccagagat gagattcttc cactggttca gcaagtggag gaagctgcat    600
cgtgaccagg agtatgaggt cacctggtac atatcctgga gccctgcac aaagtgtaca    660 agggatatgg ccacgttcct ggccgaggac ccgaaggtta ccctgaccat ctttgttgcc    720
cgcctctact acttctggga cccagattac caggaggcgc ttcgcagcct gtgtcagaaa    780
agagacggtc cgcgtgccac catgaagatc atgaattatg acgaatttca gcactgttgg    840
agcaagttcg tgtacagcca aagagagcta tttgagcctt ggaataatct gcctaaaatat   900 tatatattac tgcacatcat gctgggggag attctcagac actcgatgga tccacccaca    960 ttcacttttca actttaacaa tgaaccttgg gtcagaggac ggcatgagac ttacctgtgt   1020
tatgaggtgg agcgcatgca caatgacacc tgggtcctgc tgaaccagcg caggggcttt   1080
ctatgcaacc aggctccaca taaacacggt tccttgaag ccgccatgc agagctgtgc    1140 ttcctggacg tgattccctt tggaagctg acctggacc aggactacag ggttacctgc     1200
ttcacctcct ggagccctg cttcagctgt gcccaggaaa tggctaaatt catttcaaaa    1260
aacaaacacg tgagcctgtg catcttcact gcccgcatct atgatgatca aggaagatgt    1320 caggagggc tgcgcaccct ggccgaggct ggggccaaaa tttcaataat gacatacagt     1380
gaatttaagc actgctggga cacctttgtg gaccaccagg atgtcccctt ccagccctgg    1440
gatggactag atgagcacag ccaagacctg agtgggaggc tgcgggccat tctccagaat    1500
caggaaaact gaaggatggg cctcagtctc taaggaaggc agagacctgg gttgagcctc    1560
agaataaaag atcttcttcc aagaaatgca acaggctgt tcaccaccat ctccagctga    1620
tcacagacac cagcaaagca atgcactcct gaccaagtag attcttttaa aaattagagt    1680
gcattacttt gaatcaaaaa tttatttata tttcaagaat aaagtactaa gattgtgctc    1740
aatacacaga aaagtttcaa acctactaat ccagcgacaa tttgaatcgg ttttgtaggt    1800
agaggaataa aatgaaatac taaatctttc tgtaaaaaaa aaaaaaaa                1848
```

```
<210> SEQ ID NO 8
<211> LENGTH: 3240
<212> TYPE: DNA
<213> ORGANISM: Homo sapiens

<400> SEQUENCE: 8
agtttatctt tcactttcct gccctgagtg tgagcaagaa tttcctgcgg ttcctctagg      60
aaaattcctt tgtgcagatc aggcccgtgg attggtgagt gaatcctaac cacgtcttcc     120
ctggcctgtc ttcactcttc tccccagaat caccacttct gcactggtgt ctgaaggtgt     180
attgagtgat tttgtggagg gcagaagtag gaagtctttg gacaaaaact gtatttacct     240
tgggatctgt gaacaagagg aacctcagca gccaggacag gcaggagcag tggaatagct     300
actatggctt ctggaatcct ggttaatgta aggaggagg tgacctgccc catctgcctg      360
gaactcctga cacaacccct gagcctggac tgcggccaca gcttctgcca agcatgcctc     420
actgcaaacc acaagaagtc catgctagac aaaggagaga gtagctgccc tgtgtgccgg     480
atcagttacc agcctgagaa catacggcct aatcggcatg tagccaacat agtggagaag     540
ctcagggagg tcaagttgag cccagagggg cagaaagttg atcattgtgc acgccatgga     600
gagaaacttc tactcttctg tcaggaggac gggaaggtca tttgctggct ttgtgagcgg     660
tctcaggagc accgtggtca ccacacgttc ctcacagagg aggttgcccg ggagtaccaa     720
gtgaagctcc aggcagctct ggagatgctg aggcagaagc agcaggaagc tgaagagtta     780
gaagctgaca tcagagaaga gaaagcttcc tggaagactc aaatacagta tgacaaaacc     840
aacgtcttgg cagattttga gcaactgaga gacatcctgg actgggagga gagcaatgag     900
ctgcaaaacc tggagaagga ggaggaagac attctgaaaa gccttacgaa ctctgaaact     960
gagatggtgc agcagaccca gtccctgaga gagctcatct cagatctgga gcatcggctg    1020
caggggtcag tgatggagct gcttcagggt gtggatggcg tcataaaaag gacggagaac    1080
gtgaccttga agaagccaga aactttttcca aaaaatcaaa ggagagtgtt tcgagctcct    1140
gatctgaaag gaatgctaga agtgtttaga gagctgacag atgtccgacg ctactgggtt    1200
gatgtgacag tggctccaaa caacatttca tgtgctgtca tttctgaaga taagagacaa    1260
gtgagctctc cgaaaccaca gataatatat ggggcacgag ggacaagata ccagacattt    1320
gtgaatttca attattgtac tggcatcctg gctctcaaa gtatcacatc agggaaacat     1380
tactgggagg tagacgtgtc caagaaaact gcttggatcc tgggggtatg tgctggcttc    1440
caacctgatg caatgtgtaa tattgaaaaa aatgaaaatt atcaacctaa atacggctac    1500
tgggttatag ggttagagga aggagttaaa tgtagtgctt tccaggatag ttccttccat    1560
actccttctg ttcctttcat tgtgccctct tctgtgatta tttgtcctga tcgtgttgga    1620
gttttcctag actatgaggc ttgcactgtc tcattcttca atatcacaaa ccatggattt    1680
ctcatctata gtttttctca ctgttctttt tctcagcctg tatttccata tttaaatcct    1740
agaaaatgtg gagtccccat gactctgtgc tcaccaagct cttgaacctt cttacacact    1800
cagccccttc tgtacagcac ctcttgtcca ggtgcatctc atacacctga actcatttgc    1860
atcattttaa ccatcttttc cttgctgtct cccttctttc tatttgaacg tccttcactc    1920
atcagtaaaa tgtaataatt gccttgtgcc atattgtccc caatatttta ttgacatttg    1980
atagcaattt ttttcatcat tttccgtact cctaaggaaa actgacctat acctcataaa    2040
atgagaccgc tatttaggta ttacttctgc cagatattta tcacccaatt gcctctgaca    2100
ctgactaaga agatgaagaa aagcttttca acagcctttc tatatcatcg tgtgataatt    2160
```

| | |
|---|---|
| gttcaccaat gaatgagtcc ttagccctgt gtcagtttac cctcgatgcc cttatttgtg | 2220 |
| agttaaagag aaaatatcat aaatggtata ctcttaagta tagaggtttt gtatctagag | 2280 |
| gatctcagtt caactcctgt ctctccatat accagcagtg taactgtgaa taacatactt | 2340 |
| aaatggctgt gcttatttcc ttttcttttc ttttttcttt ttttttttt ttgagatgaa | 2400 |
| gttttgctct tgttccccag gctggagtgc aatggcacga tctcggttca ctgcaacctc | 2460 |
| cacctctcag attcaagcaa ttctcctgcc tcagcctccc aagtagctgg gattacaggt | 2520 |
| gcccaccacc acccctggct aaatttgtat tttcagtaga cacggggttt ccccatgttg | 2580 |
| gttaggctcg tctagaacct ctgacctcag gtgatccacc cgcctcggcc tcccaaagtg | 2640 |
| ctgggattac aggcgtgagc cacggcgccc agcctgtgct tattttctta aaataatttt | 2700 |
| tgtattaaaa acttcacatt aaataagtgc taatgtttta ttgcatagta gggtgactag | 2760 |
| agttaacaat aacctattgc atatattttg aaatagctag aagagaggat tttgaaagtt | 2820 |
| ctcaacacaa agaaatgaca catatttgag gtgatggata tgctaattac cctggttcgg | 2880 |
| ttattacgca atgtatacat gtatcaaaac atcacactgt accacataaa tatgtatatt | 2940 |
| tattatttgt caattaaaag caaaataaaa caaaaaacct tcatctaata ctttggatca | 3000 |
| ttgtgaaaaa ataaattcct gaagtataaa gcatctatct aagtgtcttg atctaataag | 3060 |
| tacttgttct acaaattatt gaaaaacata aactctgtta atgtctcatg aacaggttg | 3120 |
| tgccttcagg gaaactagga ttggatttac taaattctca tttttagat ctcagatact | 3180 |
| actgtcaaaa tgacttcaat tctgccttct atatataata cacacatata tttaggattt | 3240 |

<210> SEQ ID NO 9
<211> LENGTH: 1048
<212> TYPE: DNA
<213> ORGANISM: Homo sapiens

<400> SEQUENCE: 9

| | |
|---|---|
| ataaaggggt ggcccgtaga agattccagc accctcccct aactccaggc cagactcctt | 60 |
| tcagctaaag gggagatctg gatggcatct acttcgtatg actattgcag agtgcccatg | 120 |
| gaagacgggg ataagcgctg taagcttctg ctggggatag gaattctggt gctcctgatc | 180 |
| atcgtgattc tggggggtgcc cttgattatc ttcaccatca aggccaacag cgaggcctgc | 240 |
| cgggacggcc ttcgggcagt gatggagtgt cgcaatgtca cccatctcct gcaacaagag | 300 |
| ctgaccgagg cccagaaggg cttttcagga tgtggaggccc aggccgccac tgcaaccac | 360 |
| actgtgatgg ccctaatggc ttccctggat gcagagaagg cccaaggaca aagaaagtg | 420 |
| gaggagcttg agggagagat cactacatta aaccataagc ttcaggacgc gtctgcagag | 480 |
| gtggagcgac tgagaagaga aaaccaggtc ttaagcgtga aatcgcggga caagaagtac | 540 |
| taccccagct cccaggactc cagctccgct gcggcgcccc agctgctgat tgtgctgctg | 600 |
| ggcctcagcg ctctgctgca gtgagatccc aggaagctgg cacatcttgg aaggtccgtc | 660 |
| ctgctcggct tttcgcttga acattccctt gatctcatca gttctgagcg ggtcatgggg | 720 |
| caacacggtt agcggggaga gcacggggta gccggagaag ggcctctgga gcaggtctgg | 780 |
| aggggccatg gggaagtcct gggtgtgggg acacagtcgg gttgacccag ggctgtctcc | 840 |
| ctccagagcc tccctccgga caatgagtcc cccctcttgt ctcccaccct gagattgggc | 900 |
| atggggtgcg gtgtggggg catgtgctgc ctgttgttat gggttttttt tgcgggggg | 960 |
| gttgcttttt tctggggtct ttgagctcca aaaaataaac acttcctttg agggagagca | 1020 |
| cacctgaaaa aaaaaaaaaa aaaaaaa | 1048 |

```
<210> SEQ ID NO 10
<211> LENGTH: 118
<212> TYPE: DNA
<213> ORGANISM: Artificial Sequence
<220> FEATURE:
<223> OTHER INFORMATION: CCR5 subsequence of SEQ ID NO: 1

<400> SEQUENCE: 10
aggtatattg ctgttgacag tgagcgactg taaactgagc ttgctctact gtgaagccac      60
agatgggtag agcaagcaca gtttaccgct gcctactgcc tcggacttca aggggctt      118

<210> SEQ ID NO 11
<211> LENGTH: 116
<212> TYPE: DNA
<213> ORGANISM: Artificial Sequence
<220> FEATURE:
<223> OTHER INFORMATION: Vif subsequence of SEQ ID NO: 1

<400> SEQUENCE: 11
catctccatg gctgtaccac cttgtcgggg gatgtgtact tctgaacttg tgttgaatct      60
catggagttc agaagaacac atccgcactg acattttggt atctttcatc tgacca        116

<210> SEQ ID NO 12
<211> LENGTH: 115
<212> TYPE: DNA
<213> ORGANISM: Artificial Sequence
<220> FEATURE:
<223> OTHER INFORMATION: Tat subsequence of SEQ ID NO: 1

<400> SEQUENCE: 12
gcgggcctgg ctcgagcagg gggcgaggga ttccgcttct tcctgccata gcgtggtccc      60
ctcccctatg gcaggcagaa gcggcacctt ccctcccaat gaccgcgtct tcgtc         115
```